United States Patent
Noble et al.

(10) Patent No.: US 10,973,842 B2
(45) Date of Patent: Apr. 13, 2021

(54) METHOD EFFECTIVE TO MODULATE EXPRESSION OF T-BOX PROTEIN 4 (TBX4) FOR REDUCING PROGRESSION OF LUNG FIBROSIS AFTER A LUNG INJURY

(71) Applicant: CEDARS-SINAI MEDICAL CENTER, Los Angeles, CA (US)

(72) Inventors: Paul W. Noble, Beverly Hills, CA (US); Dianhua Jiang, Encino, CA (US); Ting Xie, Los Angeles, CA (US); Carol Jiurong Liang, Encino, CA (US)

(73) Assignee: CEDARS-SINAI MEDICAL CENTER, Los Angeles, CA (US)

( * ) Notice: Subject to any disclaimer, the term of this patent is extended or adjusted under 35 U.S.C. 154(b) by 0 days.

(21) Appl. No.: 15/761,403

(22) PCT Filed: Nov. 1, 2016

(86) PCT No.: PCT/IB2016/056575
§ 371 (c)(1),
(2) Date: Mar. 19, 2018

(87) PCT Pub. No.: WO2017/051402
PCT Pub. Date: Mar. 30, 2017

(65) Prior Publication Data
US 2018/0264141 A1    Sep. 20, 2018

Related U.S. Application Data

(60) Provisional application No. 62/232,854, filed on Sep. 25, 2015.

(51) Int. Cl.
| | | |
|---|---|---|
| *A61K 31/713* | (2006.01) | |
| *C12N 15/113* | (2010.01) | |
| *A61K 48/00* | (2006.01) | |
| *A61P 11/00* | (2006.01) | |

(52) U.S. Cl.
CPC .......... *A61K 31/713* (2013.01); *A61K 48/005* (2013.01); *A61K 48/0016* (2013.01); *A61P 11/00* (2018.01); *C12N 15/113* (2013.01); *A61K 48/0058* (2013.01); *A61K 48/0066* (2013.01); *C12N 2310/14* (2013.01)

(58) Field of Classification Search
CPC ................ A61K 31/713; A61K 48/005; A61K 48/0016; A61K 48/0058; A61K 48/0066; C12N 15/113; C12N 2310/14; A61P 11/00
USPC ........................................ 514/44 A; 536/24.5
See application file for complete search history.

(56) References Cited

U.S. PATENT DOCUMENTS

| | | | |
|---|---|---|---|
| 2007/0238692 A1 | 10/2007 | Evans et al. | |
| 2010/0184113 A1 | 7/2010 | Zhao et al. | |
| 2012/0159661 A1* | 6/2012 | Glimcher | ........... C07K 14/4705 800/18 |

FOREIGN PATENT DOCUMENTS

WO    2015/013508 A2    1/2015

OTHER PUBLICATIONS

Papaioannou (2014) Development, vol. 141, 3819-3833.*
Fujita et al. (2013) Pharmaceuticals, vol. 6, 223-250.*
Sun, S. et al. The T-box transcription factor Brachyury promotes renal interstitial fibrosis by repressing E-cadherin expression. Cell Communication and Signaling. 2014. vol. 12:76. http://www.biosignaling.com/content/12/1/76.
Hoffman, A.M., et al. Lung-Derived Mesenchymal Stromal Cell Post-Transplantation Survival, Persistence, Paracrine Expression, and Repair of Elastase-Injured Lung. Stem Cells Del. 2011; 20: 1779-92.
Horowitz, J.C., et al. Activation of the Pro-survival Phosphatidylinositol 3-Kinase/AKT Pathway by Transforming Growth Factor-beta1 in Mesenchymal Cells Is Mediated by p38 MAPK-dependent Induction of an Autocrine Growth Factor*. J Biol Chem. Jan. 9, 2004; 279(2): 1359-67.
Horowitz, J.C., et al. Combinatorial activation of FAK and AKT by transforming growth factor-?1 confers an anoikis-resistant phenotype to myofibroblasts. Cell Signal. Apr. 2007; 19(4): 761-71.
Hoyles, R.K., et al. An Essential Role for Resident Fibroblasts in Experimental Lung Fibrosis Is Defined by Lineage-Specific Deletion of High-Affinity Type II Transforming Growth Factor b Receptor. Am J Respir Crit Care Med. Jan. 15, 2011; 183(2): 249-6.
Hu, B., et al. Gut-Enriched Kruppel-Like Factor Interaction with Smad3 Inhibits Myofibroblast Differentiation. Am J Respir Cell Mol Biol. Jan. 2007; 36(1): 78-84.
Huang, et al; Parallelization of a local similarity algorithm:; Computer Applications in the Biosciences, 8:155-65 (1992).
Huang, X., et al. Matrix Stiffness-Induced Myofibroblast Differentiation Is Mediated by Intrinsic Mechanotransduction. Am J Respir Cell Mol Biol. Sep. 2012; 47(3): 340-8.
Humbles, A.A., et al. A Critical Role for Eosinophils in Allergic Airways Remodeling. Science. Sep. 17, 2004; 305 (5691): 1776-9.
Humphreys BD, et al. Fate tracing reveals the pericyte and not epithelial origin of myofibroblasts in kidney fibrosis. Am J Pathol. 2010;176(1):85-97.
Hung, C., et al. Role of Lung Pericytes and Resident Fibroblasts in the Pathogenesis of Pulmonary Fibrosis. Am J Respir Crit Care Med. Oct. 1, 2013; 188(7): 820-30.

(Continued)

*Primary Examiner* — Anne Marie S Wehbe
(74) *Attorney, Agent, or Firm* — McCarter & English, LLP; Beverly W. Lubit

(57) ABSTRACT

The described invention provides a method for reducing progression of lung fibrosis after a lung injury comprising administering a therapeutic amount of a therapeutic agent, wherein the therapeutic amount is effective: (a) to modulate expression of a T-box transcription factor in a population of cells in lung; and (b) to reduce proliferation of the population of cells in lung expressing the T-box transcription factor. According to some embodiments the T-box transcription factor is Tbx4.

12 Claims, 28 Drawing Sheets
(19 of 28 Drawing Sheet(s) Filed in Color)
Specification includes a Sequence Listing.

(56) References Cited

OTHER PUBLICATIONS

Hutyrova, B., et al. Interleukin-1 Gene Cluster Polymorphisms in Sarcoidosis and Idiopathic Pulmonary Fibrosis. Am J Respir Crit Care Med. Jan. 15, 2002; 165(2): 148-51.
International Preliminary Report on Patentability PCT/IB2016/056575, dated Mar. 27, 2018, 8 pages.
International Search Report and Written Opinion PCT/IB2016/05675, dated Jun. 16, 2017, 13 pages.
Ishikawa, N., et al. Utility of KL-6/MUC1 in the clinical management of interstitial lung diseases. Respir Investig. Mar. 2012; 50(1): 3-13.
Iwaisako, K., et al. Origin of myofibroblasts in the fibrotic liver in mice. Proc Natl Acad Sci USA. Aug. 12, 2014; 111 (32): E3297-305.
Iwano M, et al. Evidence that fibroblasts derive from epithelium during tissue fibrosis. J Clin Invest. 2002;110 (3):341-350.
Izbicki G. et al., Time course of bleomycin-induced lung fibrosis. Int J Exp Pathol., 83(3):111-9, 2002.
Jakubzick, C. et al Impact of Interleukin-13 Responsiveness on the Synthetic and Proliferative Properties of Th1- and Th2-Type Pulmonary Granuloma Fibroblasts. Am J Pathol. May 2003; 162(5): 1475-86.
Janick-Buckner, D. et al., Alteration of bronchoalveolar lavage cell populations following bleomycin treatment in mice. Toxicol Appl Pharmacol., 100(3):465-73, 1989.
Jensen, P., et al. Essentials of Recombinase-Based Genetic Fate Mapping in Mice. Methods Mol Biol. 2014; 1092: 437-54.
Jiang, D., et al. Hyaluronan as an Immune Regulator in Human Diseases. Physiol Rev. Jan. 2011; 91(1): 221-64.
Jiang, D., et al. Regulation of lung injury and repair by Toll-like receptors and hyaluronan. Nat Med. Nov. 2005; 11 (11): 1173-9.
Jiang, F., et al. Gene expression profile of quiescent and activated rat hepatic stellate cells implicates Wnt signaling pathway in activation. J Hepatol. Sep. 2006; 45(3): 401-9.
Jones, L. K., et al. IL-1RI deficiency ameliorates early experimental renal interstitial fibrosis. Nephrol Dail Transplant. 2009; 24: 3024-32.
Jordana, M., et al. Heterogeneous Proliferative Characteristics of Human Adult Lung Fibroblast Lines and Clonally Derived Fibroblasts from Control and Fibrotic Tissue. Am Rev Respir Dis. Mar. 1988; 137(3): 579-84.
Jozefczuk J., et al. Preparation of mouse embryonic fibroblast cells suitable for culturing human embryonic and induced pluripotent stem cells. J Vis Exp. 2012;(64):3854.
Kalluri, R & Weinberg, R.A.. The basics of epithelial-mesenchymal transition. J Clin Invest. Jun. 1, 2009; 119(6): 1420-28.
Kalluri, R., et al. Epithelial-mesenchymal transition and its implications for fibrosis. J Clin Invest. Dec. 2003; 112(12): 1776-84.
Kamari, Y., et al. Lack of Interleukin-1alpha or Interleukin-1beta Inhibits Transformation of Steatosis to Steatohepatitis and Liver Fibrosis in Hypercholesterolemic Mice. J Hepatol. Nov. 2011; 55(5): 1086-94.
Karlin & Altschul; "Applications and statistics for multiple high-scoring segments in molecular sequences"; Proc. Natl. Acad. Sci. USA, vol. 90, pp. 5873-5877, Jun. 1993.
Katzenstein, A-L., et al. Erratum to "Diagnosis of usual interstitial pneumonia and distinction from other fibrosing interstitial lung diseases". Hum Pathol. Sep. 2008; 39(9): 1275-94.
Katzenstein, A., et al. Idiopathic Pulmonary Fibrosis Clinical Relevance of Pathologic Classification. Am J Respir Crit Care Med. Apr. 2008; 157: 1301-15.
Kaviratne, M., et al. IL-13 activates a mechanism of tissue fibrosis that is completely TGF-beta independent. J Immunol. Sep. 15, 2004; 173(6): 4020-9.
Keane, MP. et al. The importance of balanced pro-inflammatory and antiinflammatory mechanisms in diffuse lung disease. Am J Physiol Lung Cell Mol Physiol. Jul. 2001; 281(1): L92-7.

Kim, K.K., et al. Alveolar epithelial cell mesenchymal transition develops in vivo during pulmonary fibrosis and is regulated by the extracellular matrix. Proc Natl Acad Sci USA. Aug. 29, 2006; 103(35): 13180-5.
Kim, V.N. MicroRNA biogenesis: coordinated cropping and dicing. Nature Reviews, Molecular Cell Biology 6 (5)376-385 (2005).
Kinder, B.W., et al. Baseline BAL Neutrophilia Predicts Early Mortality in Idiopathic Pulmonary Fibrosis. Chest. Jan. 2008; 133(1): 226-32.
Kinder, B.W. et al. Serum Surfactant Protein-A Is a Strong Predictor of Early Mortality in Idiopathic Pulmonary Fibrosis. Chest Jun. 2009; 135(6): 1557-63.
King, J. et al.Structural and functional characteristics of lung macro- and microvascular endothelial cell phenotypes. Microvasc Res. 2004; 67: 139-51.
King, T.E. et al. Effect of interferon gamma-1b on survival in patients with idiopathic pulmonary fibrosis (INSPIRE): a multicentre, randomised, placebo-controlled trial. Lancet. 2009; 374(9685): 222-8.
Kisseleva, T., et al. Myofibroblasts revert to an inactive phenotype during regression of liver fibrosis. Proc Natl Acad Sci USA. Jun. 12, 2012; 109(24): 9448-53.
Kitani, A., et al. Transforming growth factor (TGF)-beta1-producing regulatory T cells induce Smad-mediated interleukin 10 secretion that facilitates coordinated immunoregulatory activity and amelioration of TGF-beta1-mediated fibrosis. J Exp Med. Oct. 20, 2003; 198(8): 1179-88.
Kolb, M., et al. Transient expression of IL-1? induces acute lung injury and chronic repair leading to pulmonary fibrosis. J Clin Invest. Jun. 2001; 107(12): 1529-36.
Kolodsick, J.E. et al. Protection from Fluorescein Isothiocyanate-Induced Fibrosis in IL-13-Deficient, but Not IL-4-Deficient, Mice Results from Impaired Collagen Synthesis by Fibroblasts1. J Immunol. Apr. 1, 2004; 172(7): 4068-76.
Komiya, Y, et al. Wnt signal transduction pathways. Organogenesis. Apr.-Jun. 2008; 4(2): 68-75.
Konigshoff, M., et al. WNT1-inducible signaling protein-1 mediates pulmonary fibrosis in mice and is upregulated in humans with idiopathic pulmonary fibrosis. J Clin Invest. Apr. 2009; 119(4): 772-87.
Konishi, K., et al. Gene Expression Profiles of Acute Exacerbations of Idiopathic Pulmonary Fibrosis. Am J Respir Crit Care med. Jul. 15, 2009; 180(2): 167-75.
Korthagen, N.M. et al. Serum and BALF YKL-40 levels are predictors of survival in idiopathic pulmonary fibrosis. Respir Med. Jan. 2011; 105(1): 106-13.
Kramann, R., et al. Perivascular Gli1+ Progenitors Are Key Contributors to Injury-Induced Organ Fibrosis. Cell Stem Cell. Jan. 8, 2015; 16(1): 51-66.
Krenning, G., et al. The origin of fibroblasts and mechanism of cardiac fibrosis. J Cell Physiol. Nov. 2010; 225(3): 631-7.
Viukherjee, A.B., et al. Uteroglobin: A Steroid-Inducible Immunomodulatory Protein That Founded the Secretoglobin Superfamily. Endocr Rev. Dec. 2007; 28(7): 707-25.
Viurray, L.A., et al. Hyper-responsiveness of IPF/UIP fibroblasts: interplay between TGFbeta1, IL-13 and CCL2. Int J Biochem Cell Biol. 2008; 40(10): 2174-82.
Mus Musculus T-box 4 (Tbx4), Transcript Variant 2, mRNA; Accession No. NM_172798, Publication [online]. Feb. 15, 2015 [retrieved from internet Oct. 4, 2018].
Mushiroda, T., et al. A genome-wide association study identifies an association of a common variant in TERT with susceptibility to idiopathic pulmonary fibrosis. J Med Genet. Oct. 2008; 45(10): 654-6.
Myers, J.L., et al. Epithelial Necrosis and Alveolar Collapse in the Pathogenesis of Usual Interstitial Pneumonia. Chest. Dec. 1988; 94(6): 1309-11.
Naiche, L.A., et al. Identity and Fate of Tbx4-Expressing Cells Reveal Developmental Cell Fate Decisions in the Allantois, Limb, and External Genitalia. Dev Dyn. Oct. 2011; 240(10): 2290-300.
Needleman, S. B. and Wunsch, C. D.; "A general method applicable to the search for similarities in the amino acid sequence of two proteins"; J. Mol. Biol. 48:443 (1970).

(56) References Cited

OTHER PUBLICATIONS

Nobel, P. W., et al. Hyaluronate Activation of CD44 Induces Insulin-like Growth Factor-1 Expression by a Tumor Necrosis Factor-a-dependent Mechanism in Murine Macrophages. J Clin Invest. Jun. 1993; 91(6): 2368-77.

Noble, P.W., et al. Pulmonary fibrosis: patterns and perpetrators J Clin Invest. Aug. 2012; 122(8): 2756-62.

Ogawa, T., et al. Suppression of type I collagen production by microRNA-29b in cultured human stellate cells. Biochem Biophys Res Commun. Jan. 1, 2010; 391(1): 316-21.

Osterreicher, C.H., et al. Fibroblast-specific protein 1 identifies an inflammatory subpopulation of macrophages in the liver. Proc Natl Acad Sci USA. Nov. 23, 2010; 108(1): 308-13.

Ozerdem, U., et al. NG2 Proteoglycan is Expressed Exclusively by Mural Cells During Vascular Morphogenesis. Dev Dyn. Oct. 2001; 222(2): 218-27.

Paddison, P.J. et al. (2002) Stable suppression of gene expression by RNAi in mammalian cells. PNAS 99 (3):1443-1448.

Papaioannou, V.E. The T-box gene family: emerging roles in development, stem cells and cancer. Development. Oct. 2014; 141(20): 3819-33.

Pardo, A.,et al. Up-Regulation and Profibrotic Role of Osteopontin in Human Idiopathic Pulmonary Fibrosis. PLoS Med. Sep. 2005; 2(9): e251.

Paul, C.P. et al. (2002) Effective expression of small interfering RNA in human cells. Nature Biotechnology 20 (5):505-508.

Paulin, D., et al. Desmin: a major intermediate filament protein essential for the structural integrity and function of muscle.Exp Cell Res. Nov. 15, 2004; 301(1): 1-7.

Pearson, W.R., et al; "Using the FASTA Program to Search Protein and Dna Sequence Databases"; Methods in Molecular Biology, 26:307-331 (1994).

Pearson, WR and Lipman, DJ; "Improved tools for biological sequence comparison"; Proc. Natl. Acad. Sci. 85:2444 (1988).

Peterson, M.W., et al. Prognostic Role of Eosinophils in Pulmonary Fibrosis. Chest. Jul. 1987; 92(1): 51-6.

Phan, S. et al., A Comparative Study of Pulmonary Fibrosis Induced by Bleomycin and an O2 Metabolite Producing Enzyme System. Chest., 83(5 Suppl):44S-45S, 1983.

Phan, S. et al., Bleomycin-induced Pulmonary Fibrosis in Rats: Biochemical Demonstration of Increased Rate of Collagen Synthesis. Am Rev Respir Dis 121: 501-506, 1980.

Phillips, R.J., et al. Circulating fibrocytes traffic to the lungs in response to CXCL12 and mediate fibrosis. J Clin Invest. Aug. 2004; 114(3): 438-46.

Piguet, P.F., et al. Expression and Localization of Tumor Necrosis Factor-alpha and Its mRNA in Idiopathic Pulmonary Fibrosis. Am J Pathol. Sep. 1993; 143(3): 651-655.

Piguet, P.F., et al. Tumor necrosis factoricachectin plays a key role in bleomycin-induced pneumopathy and fibrosis. J Exp Med. Sep. 1, 1989; 170(3): 655-63.

Piguet. P.F., et al. Requirement of tumour necrosis factor for development of silica induced pulmonary fibrosis. Nature. Mar. 15, 1990; 344(6263): 245-7.

Prasse, A. et al. Serum CC-Chemokine Ligand 18 Concentration Predicts Outcome in Idiopathic Pulmonary Fibrosis. Am J Respir Crit Care Med. Apr. 15, 2009; 179(8): 717-23.

Rafii, R., et al. A review of current and novel therapies for idiopathic pulmonar fibrosis. J Thorac Dis. 2013; 5(1): 48-73.

Raghu, G., et al. Incidence and Prevalence of Idiopathic Pulmonary Fibrosis. Am J Respir Crit Care Med. Oct. 1, 2006; 174(7): 810-6.

Ramalingam, T.R., et al. Unique functions of the type II interleukin 4 receptor identified in mice lacking the interleukin 13 receptor ?1 chain. Nat Immunol. Jan. 2008; 9(1): 25-33.

Ramasamy, S. K., et al. Fgf10 dosage is critical for the amplification of epithelial cell progenitors and for the formation of multiple mesenchymal lineages during lung development. Dev Biol. Jul. 15, 2007; 307(2): 237-47.

Ramirez, A.M., et al. Myofibroblast Transdifferentiation in Obliterative Bronchiolitis: TGF-beta Signaling Through Smad3-Dependent and -Independent Pathways. Am J Transplant. Sep. 2006; 6(9): 2080-8.

Ramos, C. et al. Fibroblasts from Idiopathic Pulmonary Fibrosis and Normal Lungs Differ in Growth Rate, Apoptosis, and Tissue Inhibitor of Metalloproteinases Expression. Am J Respir Cell Mol Biol. May 2001; 24(5): 591-8.

Rehan, V.K., et al. PPAR? SignalingMediates the Evolution, Development, Homeostasis, and Repair of the Lung. PPAR Res. vol. 2012; Article ID 289867, 8 pages 2012.

Reiman, R.M., et al. Interleukin-5 (IL-5) Augments the Progression of Liver Fibrosis by Regulating IL-13 Activity. Infect Immun. Mar. 2006; 74(3): 1471-9.

Richards,T.J., et al. Peripheral Blood Proteins Predict Mortality in Idiopathic Pulmonary Fibrosis.Am J Respir Crit Care Med. Jan. 1, 2012; 185(1): 67-76.

Rinkevich Y, et al. Identification and isolation of a dermal lineage with intrinsic fibrogenic potential. Science. 2015;348(6232): aaa2151.

Roberts, S.N. et al. A novel model for human interstitial lung disease: Hapten-driven lung fibrosis in rodents. J Pathol. Jul. 1995; 176(3): 309-18.

Rock, J.R., et al. Multiple stromal populations contribute to pulmonary fibrosis without evidence for epithelial to mesenchymal transition. Proc Natl Acad Sci USA. Dec. 27, 2011; 108(52): E1475-83.

Rodriguez-Esteban C, et al. The T-box genes Tbx4 and Tbx5 regulate limb outgrowth and identity. Nature. 1999;398(6730):814-818.

Rosas, I.O., et al. MMPI and MMP7 as Potential Peripheral Blood Biomarkers in Idiopathic Pulmonary Fibrosis. PLoS Med. Apr. 29, 2008; 5(4): e93.

Ross, J.S. et al. miRNA the New Gene Silencer, Am J Clin Pathol. 2007; 128(5): 830-36.

Rothman, B.L., et al. Cytokine regulation of C3 and C5 production by the human type II pneumocyte cell line, A549. J. Immunol. 1990; 145: 592-598.

Sakiyama J, et al. Tbx4-Fgf10 system controls lung bud formation during chicken embryonic development. Development. 2003;130(7):1225-1234.

Satelli, A., et al. Vimentin as a potential molecular target in cancer therapy Or Vimentin, an overview and its potential as a molecular target for cancer therapy. Cell Mol Life Sci. Sep. 2011; 68(18): 3033-46.

Satoh, H., et al. Increased levels of KL-6 and subsequent mortality in patients with interstitial lung diseases.J Intern Med. Nov. 2006; 260(5): 429-34.

Sauer, B. & Henderson, N.. Site-specific DNA recombination in mammalian cells by the Cre recombinase of bacteriophage P1. PNAS 1988; 85: 5166-70.

Sausville, E., et al. A role for ferrous ion and oxygen in the degradation of DNA by bleomycin. Biochem Biophys Res Commun. Dec. 6, 1976; 73(3): 814-22.

Schniedermann, J., et al. Mouse lung contains endothelial progenitors with high capacity to form blood and lymphatic vessels BMC Cell Biol. 2010; 11:50.

Schrier D. et al., The Role of Strain Variation in Murine Bleomycin-Induced Pulmonary Fibrosis. Am Rev Respir Dis., 127(1):63-6,1983.

Kretzschmar, K.,et al. Lineage Tracing. Cell. Jan. 20, 2012; 148(1-2): 33-45.

Krizhanovsky, V., et al. Senescence of Activated Stellate Cells Limits Liver Fibrosis. Cell. Aug. 22, 2008; 134(4): 657-67.

Kuan, CT et al, Glycoprotein Nonmetastatic Melanoma Protein B, a Potential Molecular Therapeutic Target in Patients with Glioblastoma Multiforme. Clin. Cancer Res. 12:(7) 1970-82 (2006).

Kumar, M. E, et al. Defining a mesenchymal progenitor niche at single cell resolution. Science. Nov. 14, 2014; 346 (6211): 1258810.

Kuperman, D.A., et al. Direct effects of interleukin-13 on epithelial cells cause airway hyperreactivity and mucus overproduction in asthma. Nat Med. Aug. 2002; 8(8): 885-9.

(56) References Cited

OTHER PUBLICATIONS

Laan, M., et al. Neutrophil Recruitment by Human IL-17 Via C-X-C Chemokine Release in the Airways. J Immunol. Feb. 15, 1999; 162(4): 2347-52.
Larsson, O., et al. Fibrotic Myofibroblasts Manifest Genome-Wide Derangements of Translational Control. PLoS One. Sep. 16, 2008; 3(9): e3220.
Latsi, P.I., et al. Fibrotic Idiopathic Interstitial Pneumonia the Prognostic Value of Longitudinal Functional Trends. Am J Respir Crit Care Med. Sep. 1, 2003; 168(5): 531-537.
Latsi,. P., et al. Analysis of IL-12 p40 subunit gene and IFN-? G5644A polymorphisms in Idiopathic Pulmonary Fibrosis. Respir Res. 2003. 4:6.
Lawson W. et al., Increased and prolonged pulmonary fibrosis in surfactant protein C-deficient mice following intratracheal bleomycin. Am J Pathol. 2005;167(5):1267-1277.
Lawson, W.E, et al. Genetic mutations in surfactant protein C are a rare cause of sporadic cases of IPF. Thorax. Nov. 2004; 59(11): 977-80.
Lebleu, V.S., et al. Origin and Function of Myofibroblasts in Kidney Fibrosis. Nat Med. Aug. 2013; 19(8): 1047-53.
Lee, C.G. et al. Interleukin-13 induces tissue fibrosis by selectively stimulating and activating transforming growth factor beta(1). J Exp Med. Sep. 17, 2001; 194(6): 809-821.
Lee, J.H. et al. Interleukin-13 Induces Dramatically Different Transcriptional Programs in Three Human Airway Cell Types. Am J Respir Cell Mol Biol. Oct. 2001; 25(4): 474-85.
Lesley, J., et al. CD44 and Its Interaction with Extracellular Matrix. Adv Immunol. 1993; 54: 271-335.
Levick, S. P., et al. Cardiac Mast Cells Mediate Left Ventricular Fibrosis in the Hypertensive Rat Heart. Hypertension. Jun. 2009; 53(6): 1041-1047.
Li, Y., et al. Severe lung fibrosis requires an invasive fibroblast phenotype regulated by hyaluronan and CD44. J Exp Med. Jul. 4, 2011; 208(7): 1459-1471.
Li, Z., et al. Protein Kinase C d and c-Abl Kinase Are Required for Transforming Growth Factor beta Induction of Endothelial-Mesenchymal Transition In Vitro. Arthritis Rheum. Aug. 2011; 63(8): 2473-83.
Liu, G., et al. miR-21 mediates fibrogenic activation of pulmonary fibroblasts and lung fibrosis. J Exp Med. Aug. 2, 2010; 207(8): 1589-97.
Liu, J., et al. Sonic hedgehog signaling directly targets Hyaluronic Acid Synthase 2, an essential regulator of phalangeal joint patterning. Dev Biol. Mar. 15, 2013; 375(2): 160-71.
Liu, L. et al. Association of ENA-78, IP-10 and VEGF gene polymorphism with idiopathic pulmonary fibrosis. Zhonghua yi xue za zhi. Oct. 20, 2009; 89(38): 2690-4 (Abstract).
Liu, Y., et al. IL-13 Induces Connective Tissue Growth Factor in Rat Hepatic Stellate Cells via TGF-beta-Independent Smad Signaling. J Immunol. Sep. 1, 2011; 187(5): 2814-2823.
Livet, J., et al. Transgenic strategies for combinatorial expression of fluorescent proteins in the nervous system. Nature. Nov. 1, 2007; 450: 56-62.
Lok, S.S. et al.Murine gammaherpes virus as a cofactor in the development of pulmonary fibrosis in bleomycin resistant mice. Eur Respir J. Nov. 2002; 20(5): 1228-32.
Lovgren, A.K. et al. beta-arrestin Deficiency Protects Against Pulmonary Fibrosis in Mice and Prevents Fibroblast Invasion of Extracellular Matrix. SC. Sci Transl Med. Mar. 16, 2011; 3(74):74ra23. doi:10.1126/scitranslmed.3001564.
Lown, J.W. et al. The mechanism of the bleomycin-induced cleavage of DNA1. Biochem Biophys Res Commun. Aug. 22, 1977; 77(4): 1150-7.
Madisen, L, et al. A robust and high-throughput Cre reporting and characterization system for the whole mouse brain. Nat Neurosci. Jan. 2010; 13(1): 133-40.

Mailleuix, A. A., et al. Fgf10 expression identifies parabronchial smooth muscle cell progenitors and is required for their entry into the smooth muscle cell lineage. Development. May 2005; 132(9): 2157-66.
Martinelli, M., et al. A role for epidermal growth factor receptor in idiopathic pulmonary fibrosis onset. Mol Biol Rep. Oct. 2011; 38(7): 4613-7.
Martinez, F.O., et al. The M1 and M2 paradigm of macrophage activation: time for reassessment. F1000Prime Rep. 2014; 6:13.
Mason, R.J. Biology of alveolar type II cells. Respirology. Jan. 2006; 11 Suppl: S12-5.
McDonald, S. et al. Combined betaseron R (recombinant human interferon beta) and radiation for inoperable non-small cell lung cancer. Radiother Oncol. Mar. 1993; 26(3): 212-8.
McQualter, J.L., et al Concise Review: Deconstructing the Lung to Reveal Its Regenerative Potential. Stem Cells. May 2012; 30(5): 811-6.
McQualter, J.L., et al. Endogenous Fibroblastic Progenitor Cells in the Adult Mouse Lung Are Highly Enriched in the Sca-1 Positive Cell Fraction. Stem Cells. 2009; 27: 612-22.
McQualter, J.L., et al. Evidence of an epithelial stem/progenitor cell hierarchy in the adult mouse lung. Proc Natl Acad Sci USA 2010; 107: 1414-19.
Meltzer, E.B., et al. Bayesian probit regression model for the diagnosis of pulmonary fibrosis: proof-of-principle. BMC Med Genomics. Oct. 5, 2011; 4:70.
Meltzer, E.B., et al., Idiopathic pulmonary fibrosis. Orphanet J Rare Dis. Mar. 26, 2008; 3: 8. doi:10.1186/1750-1172-3-8.
Mentink-Kane, M.M., et al. Accelerated and Progressive and Lethal Liver Fibrosis in Mice that Lack Interleukin (IL)-10, IL-12p40, and IL-13R ?2.Gastroenterology. Dec. 2011; 141(6): 2200-9.
Mentink-Kane, M.M., et al. Opposing roles for IL-13 and IL-13 receptor a2 in health and disease. Immunol Rev. Dec. 2004; 202: 191-202.
Meyers and Miller. Optimal alignments in linear space. Computer Applic. Biol. Sci., 4:11-17 (1988).
Mikecz, K, et al. Anti-CD44 treatment abrogates tissue oedema and leukocyte infiltration in murine arthritis . . . Nat Med. Jun. 1995; 1(6): 558-63.
Minshall, E.M., et al. Eosinophil-associated TGF-beta1 mRNA expression and airways fibrosis in bronchial asthma . . . Am J Respir Cell Mol boil. Sep. 1997; 17(3): 326-33.
Miyazaki, Y. et al. Expression of a Tumor Necrosis Factor-a Transgene in Murine Lung Causes Lymphocytic and Fibrosing Alveolitis a Mouse Model of Progressive Pulmonary Fibrosis. J Clin Invest. Jul. 1995; 96(1): 250-9.
Moeller, A., et al. Circulating Fibrocytes Are an Indicator of Poor Prognosis in Idiopathic Pulmonary Fibrosis. Am J Respir Crit Care Med. Apr. 1, 2009; 179(7): 588-94.
Monroe, D.M., et al. Platelets and Thrombin Generation. Arterioscler Thromb Vasc Biol. 2002; 22:1381-1389.
Moore BB, et al. CCR2-mediated recruitment of fibrocytes to the alveolar space after fibrotic injury. Am J Pathol. 2005;166(3):675-684.
Moore, B.B. et al. Murine models of pulmonary fibrosis. Am J Physiol Lung Cell Mol Physiol. Feb. 2008; 294(2): L152-60.
Moore, B.B. et al. Animal Models of Fibrotic Lung Disease. Am J Respir Cell Mol Biol. Aug. 2013; 49(2): 167-79.
Morrisey, E.E.,et al. Preparing for the First Breath: Genetic and Cellular Mechanisms in Lung Development. Dev Cell. Jan. 19, 2010; 18(1): 8-2.
Muggia, F. et al., Pulmonary toxicity of antitumor agents. Cancer Treat Rev, 10: 221-243, 1983.
Darby, I., et al. a-Smooth muscle actin is transiently expressed by myofibroblasts during experimental wound healing. Lab Invest. Jul. 1990; 63(1): 21-29.
Darby, I.A., et al. Fibroblasts and myofibroblasts in wound healing. Clin Cosmet Investig Dermatol. 2014; 7: 301-11.
De Langhe, S. P., et al. Levels of mesenchymal FGFR2 signaling modulate smooth muscle progenitor cell commmitment in the lung. Dev Biol. Nov. 1, 2006; 299(1): 52-62.
De Wever, O., et al. Role of tissue stroma in cancer cell invasion. J Pathol. Jul. 2003; 200(4): 429-447.

(56) References Cited

OTHER PUBLICATIONS

Degrendele, H.C., et al. Requirement for CD44 in Activated T Cell Extravasation into an Inflammatory Site. Science. Oct. 24, 1997; 278(5338): 672-5.

Degryse, A.L., et al. Repetitive intratracheal bleomycin models several features of idiopathic pulmonary fibrosis. Am J Physiol Lung Cell Mol Physiol. Oct. 2010; 299(4): L442-52.

Desmouliere, A., et al. Apoptosis Mediates the Decrease in Cellularity during the Transition between Granulation Tissue and Scar. Am J Pathol. Jan. 1995; 146(1): 56-66.

Di Sabatino A, et al. Blockade of transforming growth factor beta upregulates T-box transcription factor T-bet, and increases T helper cell type 1 cytokine and matrix metalloproteinase-3 production in the human gut mucosa. Gut. 2008,57(5):605-612.

Ding, B., et al. Endothelial-Derived Angiocrine Signals Induce and Sustain Regenerative Lung Alveolarization. Cell. Oct. 28, 2011; 147(3): 539-53.

DNAzymes Scientific Background. Sterna Biologicals, GmbH & Co. KG, www.sterna-biologicals.com. printed from Internet Sep. 24, 2018.

Duffield, J.S. Cellular and molecular mechanisms in kidney fibrosis. J Clin. Invest. Jun. 2014; 124(6): 2299-306.

Dulauroy, S. et al. Lineage tracing and genetic ablation of ADAM12+ perivascular cells identify a major source of profibrotic cells during acute tissue injury. Nat Med. Aug. 2012; 18(8): 1262-70.

Duong, H., et al. Pro-angiogenic Hematopoietic Progenitor Cells and Endothelial Colony Forming Cells in Pathological Angiogenesis of Bronchial and Pulmonary Circulation. Angiogenesis. 2011; 14(4): 411-22.

Fan, J et al. Interleukin-1 induces tubular epithelial-myofibroblast transdifferentiation through a transforming growth factor-beta1-dependent mechanism in vitro. Am J Kidney Dis. Apr. 2001; 37(4): 820-31.

Fernando RI, et al. The T-box transcription factor Brachyury promotes epithelial mesenchymal transition in human tumor cells. J Clin Invest. 2010;120(2):533-544.

Flaherty, K.R., et al. Prognostic Implications of Physiologic and Radiographic Changes in Idiopathic Interstitial PneumoniaAm J Respir Crit Care Med. Sep. 1, 2003; 168(5): 543-8.

Foronjy RF, et al. Structural emphysema does not correlate with lung compliance: lessons from the mouse smoking model. Exp Lung Res. 2005;31(6):547-562.

Fox, C., Drug Delivery & Development. Reversing Idiopathic Pulmonary Fibrosis. http://www.dddmag.com/news/2014/10/reversing-idiopathic-pulmonary-fibrosis, Oct. 15, 2014; downloaded from internet Aug. 15, 2018.

Franzdottir, S.R., et al. Airway branching morphogenesis in three dimensional culture. Respir Res. 2010; 11: 162.

Friedman, S.L. Fibrogenic cell reversion underlies fibrosis regression in liver. Proc Natl Acad Sci USA. Jun. 12, 2012; 109(24): 9230-9231.

Fukuda, Y., et al. Patterns of Pulmonary Structural Remodeling After Experimental Paraquat Toxicity. Am J Pathol. Mar. 1985; 118(3): 452-75.

Furuhashi, K., et al. Increased expression of YKL-40, a chitinase-like protein, in serum and lung of patients with idiopathic pulmonary fibrosis. Respir Med. Aug. 2010; 104(8): 1204-10.

Gangadharan, B. et al. Murine gammaherpesvirus-induced fibrosis is associated with the development of alternatively activated macrophages. J Leukoc Biol. Jul. 2008; 84(1): 50-8.

Gasse, P., et al. IL-1 and IL-23 Mediate Early IL-17A Production in Pulmonary Inflammation Leading to Late Fibrosis. PLoS One. 2011; 6(8): e23185.

Gasse P. et al. IL-1R1/MyD88 signaling and the inflammasome are essential in pulmonary inflammation and fibrosis in mice. J Clin Invest. Dec. 2007; 117(12): 3786-99.

Giangreco, A., et al. Molecular phenotype of airway side population cells. Am J Physiol Lung Cell Mol Physiol. 2004; 286: L624-30.

Giannone, G., et al. Substrate rigidity and force define form through tyrosine phosphatase and kinase pathways. Trends Cell Biol. Apr. 2006; 16(4): 213-23.

Gilani, S. R., et al. CD28 Down-Regulation on Circulating CD4 T-Cells Is Associated with Poor Prognoses of Patients with Idiopathic Pulmonary Fibrosis. PLoS One. Jan. 29, 2010; 5(1): e8959.

Gilbert, H.S. Myelofibrosis revisited: characterization and classification of myelofibrosis in the setting of myeloproliferative disease. Prog Clin Biol Res. 1984; 154: 3-17 (Abstract).

Goldstein R., et al., Failure of mechanical properties to parallel changes in lung connective tissue composition in bleomycin-induced pulmonary fibrosis in hamsters. Am Rev Respir Dis., 120(1):67-73, 1979.

Gomperts BN, et al. Foxj1 regulates basal body anchoring to the cytoskeleton of ciliated pulmonary epithelial cells. J Cell Sci. Mar. 15, 2004; 117(Pt 8): 1329-37.

Greene, K.E., et al. Serum surfactant proteins-A and -D as biomarkers in idiopathic pulmonary fibrosis. Eur Respir J. Mar. 2002; 19(3): 439-46.

Harari, S., et al. IPF: new insight on pathogenesis and treatment. Allergy. May 2010; 65(5):537-53.

Hashimoto, N., et al. Bone marrow-derived progenitor cells in pulmonary fibrosis. J Clin Invest. Jan. 2004; 113(2): 243-52.

Hashimoto, N., et al. Endothelial-Mesenchymal Transition in Bleomycin-Induced Pulmonary Fibrosis. Am J Respir Cell Mol Biol. Aug. 2010; 43(2): 161-72.

He, W., et al. Matrix Metalloproteinase-7 as a Surrogate Marker Predicts Renal Wnt/b-Catenin Activity in CKD. J Am Soc Nephrol. Feb. 2012; 23(2): 294-304.

Hecker L et al., NADPH Oxidase-4 Mediates Myofibroblast Activation and Fibrogenic Responses to Lung Injury. Nat Med., 15(9):1077-81, 2009.

Hegab, A. E., et al. Isolation and Characterization of Murine Multipotent Lung Stem Cells. Stem Cells Dev. 2010; 19: 523-36.

Heise, R. L., et al. Mechanical Stretch Induces Epithelial-Mesenchymal Transition in Alveolar Epithelia via Hyaluronan Activation of Innate Immunity. J Biol Chem. May 20, 2011; 286(20): 17435-44.

Henderson, N.C., et al. Targeting of alpha (v) integrin identifies a core molecular pathway that regulates fibrosis in several organs. Nat Med. Dec. 2013; 19(12): 1617-24.

Henikoff & Henikoff; "Amino acid substitution matrices from protein blocks"; Proc. Natl. Acad. Sci. USA vol. 89, pp. 10915-10919, Nov. 1992.

Higgins, D. G. and Sharp, P. M., ; Fast and sensitive multiple sequence alignments on a microcomputer; CABIOS, 5:151-153 (1989).

Higgins, D. G. and Sharp, P. M.; "CLUSTAL: a package for performing multiple sequence alignment on a microcomputer"; Gene 73:237-244 (1988).

Hinz, B. Formation and Function of the Myofibroblast during Tissue Repair. J Invest Dermatol. Mar. 2007; 127(3): 526-37.

Hinz, B. Tissue stiffness, latent TGF-beta1 activation, and mechanical signal transduction: implications for the pathogenesis and treatment of fibrosis. Curr Rheumatol Rep. Apr. 2009; 11(2): 120-6.

Hinz, B., et al. Alpha-Smooth Muscle Actin Expression Upregulates Fibroblast Contractile Activity. Mol Biol Cell. Sep. 2001; 12(9): 2730-41.

Hinz, B., et al. Biological Perspectives the Myofibroblast One Function, Multiple Origins. Am J Pathol. Jun. 2007; 170 (6): 1807-16.

Hinz, B., et al. Myofibroblast Development Is Characterized by Specific Cell-Cell Adherens Junctions. Mol Biol Cell. Sep. 2004; 15(9): 4310-20.

Hinz, B., Masters and servants of the force: The role of matrix adhesions in myofibroblast force perception and ransmission. Eur J Cell Biol. Apr. 2006; 85(3-4): 175-181.

Hodgson, U., et al. ELMOD2 Is a Candidate Gene for Familial Idiopathic Pulmonary Fibrosis. Am J Hum Genet. Jul. 2006; 79(1): 149-54.

Seibold, M.A., et al. A Common MUC5B Promoter Polymorphism and Pulmonary Fibrosis. N Engl J Med. Apr. 21, 2011; 364(16): 1503-12.

(56) References Cited

OTHER PUBLICATIONS

Selman M, et al. Idiopathic pulmonary fibrosis: aberrant recapitulation of developmental programs?. PLoS Med. 2008;5(3):e62.
Selman, M. & Pardo, A. Idiopathic pulmonary fibrosis: an epithelial/fibroblastic cross-talk disorder. Respir Res. 2002; 3: 3.
Shan, L., et al. Centrifugal Migration of Mesenchymal Cells in Embryonic Lung. Dev Dyn. 2008; 237: 750-5.
Shao, D.D., et al. Pivotal Advance: Th-1 cytokines inhibit, and Th-2 cytokines promote fibrocyte differentiation. J Leukoc Biol. Jun. 2008; 83(6): 1323-33.
Siegelman, M.H., et al. Activation and interaction of CD44 and hyaluronan in immunological systems. J Leukoc Biol. Aug. 1999; 66(2): 315-21.
Silva, J.M. et al. (2005) Second-generation shRNA libraries covering the mouse and human genomes. Nature Genetics 37(11):1281-1288.
Smith, M., et al. Usual interstitial pneumonia-pattern fibrosis in surgical lung biopsies. Clinical, radiological and histopathological clues to aetiology.J Clin Pathol. Oct. 2013; 66(1): 896-903.
Smith, T.F. and Waterman, M.S. Comparison of Biosequences. Adv. Appl. Math. 2:482-489(1981).
Snider, G. et al., Chronic Interstitial Pulmonary Fibrosis Produced in Hamsters by Endotracheal Bleomycin—Lung Volumes, Volume-Pressure Relations, Carbon Monoxide Uptake, and Arterial Blood Gas Studies. Am Rev Respir Dis. 117: 289-297.
Song, J. W., et al. Acute Exacerbation of Idiopathic Pulmonary Fibrosis: Incidence, Risk Factors, and Outcome. Eur Respir J. Feb. 2011; 37(2): 356-63.
Starcher B. et al., Increased elastin and collagen content in the lungs of hamsters receiving an intratracheal injection of bleomycin. Am Rev Respir Dis., 117(2):299-305, 1978.
Sternberg, N. & Hamilton, D. Bacteriophage P1 site-specific recombination: I. Recombination between loxP sites J Mol Biol. 1981; 150: 467-86.
Strunk, R.C., et al. Pulmonary Alveolar Type 11 Epithelial Cells Synthesize and Secrete Proteins of the Classical and Alternative Complement Pathways. J. Clin. Invest. 1988; 81: 1419-1426.
Suganuma, H., et al. Enhanced migration of fibroblasts derived from lungs with fibrotic lesions. Thorax. Sep. 1995; 50 (9): 984-9.
Summer, R., et al. Isolation of an Adult Mouse Lung Mesenchymal Progenitor Cell Population. Am J Respir Cell Mol Biol. 2007; 37: 152-9.
Sun, H. et al., Oligonucleotide Aptamers: New Tools for Targeted Cancer Therapy. Molec. Therapy—Nucleic Acids 2014, 3: e182; doi: 10.1038/mbna.2014.32.
Tager, A.M., et al. Inhibition of Pulmonary Fibrosis by the Chemokine IP-10/CXCL10. Am J Respir Cell Mol Biol. Oct. 2004; 31(4): 395-404.
Takeuchi JK, et al. Tbx5 and Tbx4 trigger limb initiation through activation of the Wnt/Fgf signaling cascade. Development. 2003;130(12):2729-2739.
Takeuchi, J. K., et al. Tbx5 and Tbx4 genes determine the wing/leg identity of limb buds. Nature. Apr. 29, 1999; 398 (6730): 810-4.
Tanjore, H., et al. Contribution of Epithelial-derived Fibroblasts to Bleomycin-induced Lung Fibrosis. Am J Respir Crit Care Med. Oct. 1, 2009; 180(7): 657-65.
Teder, P., et al. Resolution of Lung Inflammation by CD44. Science. Apr. 5, 2002; 296: 155-8.
Thannickal, V.J., et al. Myofibroblast Differentiation by Transforming Growth Factor-beta 1 Is Dependent on Cell Adhesion and Integrin Signaling via Focal Adhesion Kinase. J Biol Cehm. Apr. 4, 2003; 278(14): 12384-12389.
Thomas, A.Q., et al. Heterozygosity for a Surfactant Protein C Gene Mutation Associated with Usual Interstitial Pneumonitis and Cellular Nonspecific Interstitial Pneumonitis in One Kindred. Am J. Respir Crit Care Med. May 1, 2002; 165(9): 1322-8.
Thrall, R. et al., Bleomycin-induced pulmonary fibrosis in the rat: inhibition by indomethacin. Am J Pathol, 95: 117-130, 1979.
Timmermans, F., et al. Endothelial progenitor cells: identity defined?. J Cell Mol Med. 2009; 13: 87-102.
Tomasek, J.J., et al. Myofibroblasts and mechano-regulation of connective tissue remodelling. Nat Rev Mol Cell Biol. May 2002; 3(5): 349-63.
Toole, B. P. Hyaluronan: from extracellular glue to pericellular cue. Nat Rev Cancer. Jul. 2004; 4(7): 528-39.
Torry, D.J., et al. Anchorage-independent Colony Growth of Pulmonary Fibroblasts Derived from Fibrotic Human Lung Tissue. J Clin Invest. Apr. 1994; 93(4): 1525-32.
Tsakiri, K.D., et al. Adult-onset pulmonary fibrosis caused by mutations in telomerase. Proc Natl Acad Sci USA. May 1, 2007; 104(18): 7552-7.
Ulloa, L et al. Inhibition of transforming growth factor-b/SMAD signalling by the interferon-g/STAT pathway. Nature Feb. 25, 1999; 397(6721): 710-3.
Umezawa, H. et al., Studies on bleomycin Cancer 20: 891-895, 1967.
Umezawa, H., Chemistry and mechanism of action of bleomycin . . . Fed Proc, 33: 2296 2302, 1974.
Vaccaro, C.A., et al. Alveolar Wall Basement Membranes in Bleomycin-induced Pulmonary Fibrosis. Am Rev Respir Dis. Oct. 1985; 132(4): 905-12.
Valenta, T., et al. The many faces and functions of b-catenin. EMBO J. Jun. 13, 2012; 31(12): 2714-36.
Van Deventer HW, et al. Circulating fibrocytes prepare the lung for cancer metastasis by recruiting Ly-6C+ monocytes via CCL2. J Immunol. 2013;190(9):4861-4867.
Vittal, R. et al., Effects of the Protein Kinase Inhibitor, Imatinib Mesylate, on Epithelial/Mesenchymal Phenotypes: Implications for Treatment of Fibrotic Diseases. J Pharmacol Exp Ther., 321(1):35-44, 2007.
Vittal, R. et al., Modulation of Prosurvival Signaling in Fibroblasts by a Protein Kinase Inhibitor Protects against Fibrotic Tissue Injury. Am J Pathol., 166(2):367-75, 2005.
Voehringer, D., et al. Homeostasis and Effector Function of Lymphopenia-Induced "Memory-Like" T Cells in Constitutively T Cell-Depleted Mice1. J Immunol. Apr. 1, 2008; 180(7): 4742-53.
Volckaert, T., et al. Parabronchial smooth muscle constitutes an airway epithelial stem cell niche in the mouse lung after injury. J Clin Invest. 2011; 121: 4409-19.
Waghray, M., et al. Hydrogen peroxide is a diffusible paracrine signal for the induction of epithelial cell death by activated myofibroblasts. FASEB J. May 2005; 19(7): 854-6.
Wang, D. et al. A pure population of lung alveolar epithelial type II cells derived from human embryonic stem cells. Proc Natl Acad Sci USA. Mar. 13, 2007; 104(11): 4449-54.
Wang, Y., et al. Genetic Defects in Surfactant Protein A2 Are Associated with Pulmonary Fibrosis and Lung Cancer. Am J Hum Genet. Jan. 2009; 84(1): 52-9.
Wendling, O., et al. Efficient temporally-controlled targeted mutagenesis in smooth muscle cells of the adult mouse. Genesis. Jan. 2009; 47(1): 14-8.
Werner, S., et al. Regulation of Wound Healing by Growth Factors and Cytokines. Physiol Rev. Jul. 2003; 83(3): 835-870.
White, E.S., et al. Negative Regulation of Myofibroblast Differentiation by PTEN (Phosphatase and Tensin Homolog Deleted on Chromosome 10) Sem. Am J Respir Crit Care Med. Jan. 1, 2006; 173(1): 112-21.
White, ES et al., Pathogenetic mechanisms in usual interstitial pneumonia/ idiopathic pulmonary fibrosis. 2003, J. Pathol. 201: 343-354.
Wiegand, S. et al. Global Quantitative Phosphoproteome Analysis of Human Tumor Xenografts Treated with a CD44 Antagonist. Cancer Res. Sep. 2012; 72(17): 4329-39.
Willis BC, et al. Induction of epithelial-mesenchymal transition in alveolar epithelial cells by transforming growth factor-pl: potential role in idiopathic pulmonary fibrosis. Am J Pathol. 2005;166(5):1321-1332.
Wilson, M.S., et al. Bleomycin and IL-1beta-mediated pulmonary fibrosis is IL-17A dependent. J Exp Med. Mar. 15, 2010; 207(3): 535-52.
Wilson, M.S., et al. Colitis and Intestinal Inflammation in IL10−/− Mice Results From IL-13Ra2-Mediated Attenuation of IL-13 Activity. Gastroenterology. Jan. 2011; 140(1): 254-64.

(56) References Cited

OTHER PUBLICATIONS

Wipff, P., et al. Myofibroblast contraction activates latent TGF-beta1 from the extracellular matrix. J Cell Biol. Dec. 17, 2007; 179(6): 1311-23.
Wooten, J. and Federhen, S., Statistics of Local Complexity in Amino Acid Sequences and Sequence Databases. Comput. Chem., 17:149-163 (1993).
www.genecards.org/cgi-bin/carddisp.pl?gene=CD44. printed from internet Sep. 7, 2018.
www.genecards.org/cgi-bin/carddisp.pl?gene=CTNNB1. printed from internet Aug. 20, 2018.
www.genecards.org/cgi-bin/carddisp.pl?gene=WNT1. printed from internet Aug. 20, 2018.
Wynn, T.A., et al. An IL-12-based vaccination method for preventing fibrosis induced by schistosome infection. Nature. Aug. 17, 1995; 376(6541): 594-6.
Wynn, T.A., et al. Macrophages: Master Regulators of Inflammation and Fibrosis. Semin Liver Dis. Aug. 2010; 30(3): 245-57.
Wynn, T.A., et al. Mechanisms of fibrosis: therapeutic translation for fibrotic disease. Nat Med. Jul. 6, 2012; 18(7): 1028-40.
Xie, T., et al. Transcription Factor TBX4 Regulates Myofibroblast Accumulation and Lung Fibrosis. J. Clin Invest. Aug. 2016, vol. 126, No. 8, 3063-3079.
Yamamoto, H., et al. Epithelial-vascular cross talk mediated by VEGF-A and HGF signaling directs primary septae formation during distal lung morphogenesis. Dev Biol. Aug. 1, 2007; 308(1) 44-53.
Yoder, M.C., Progenitor Cells in the Pulmonary Circulation. Proc Am Thorac Soc. 2011; 8: 466-70.
Yokoyama, A., et al. Prognostic value of circulating KL-6 in idiopathic pulmonary fibrosis. Respirology. Mar. 2006; 11 (2): 164-8.
Zasloff, M. Antimicrobial peptides of multicellular organisms. Nature. Jan. 24, 2002; 415(6870): 389-95.
Zeisberg M, et al al. BMP-7 counteracts TGF-beta1-induced epithelial-to-mesenchymal transition and reverses chronic renal injury. Nat Med. 2003;9(7):964-968.
Zeisberg M., et al. Cellular Mechanisms of Tissue Fibrosis. 1. Common and organ-specific mechanisms associated with tissue fibrosis. Am J Physiol Cell Physiol. Feb. 1, 2013; 304(3): C216-25.
Zhang, K., et al. Lung monocyte chemoattractant protein-1 gene expression in bleomycin-induced pulmonary fibrosis. J Immunol. Nov. 15, 1994; 153(10): 4733-41.
Zhang, W., et al. Spatial-temporal targeting of lung-specific mesenchyme by a Tbx4 enhancer. BMC Biology 2013, 11:111.
Zhang, Y. et al. A Variant in the Promoter of MUC5B and Idiopathic Pulmonary Fibrosis. N Engl J Med. Apr. 21, 2011; 364(16): 1576-7.
Zhang, Y., et al. Enhanced IL-1 beta and tumor necrosis factor-alpha release and messenger RNA expression in macrophages from idiopathic pulmonary fibrosis or after asbestos exposure. J Immunol. May 1, 1993; 150(9): 4188-96.
Zhang, Y., et al., Biomarkers in idiopathic pulmonary fibrosis. Curr Opin Pulm Med. Sep. 2012; 18(5): 441-6.
Zhang. K., et al. Myofibroblasts and Their Role in Lung Collagen Gene Expression during Pulmonary Fibrosis. Am J Pathol. Jul. 1994; 145(1): 114-25.
Zhao, Y.X.., et al. Secretion of complement components of the alternative pathway (C3 and factor B) by the human alveolar type II epithelial cell line A549. Int J Mol Med. 2000; 5: 415-419.
Zheng, B., et al. LLigand-Dependent Genetic Recombination in Fibroblasts a Potentially Powerful Technique for Investigating Gene Function in Fibrosis Am J Pathol. May 2002; 160(5): 1609-17.
Zhou, Y., et al. Inhibition of mechanosensitive signaling in myofibroblasts ameliorates experimental pulmonary fibrosis. J Clin Invest. Mar. 2013; 123(3): 1096-108.
Zhu, F., et al. IL-17 induces apoptosis of vascular endothelial cells—A potential mechanism for human acute coronary syndrome. Clin Immunol. Nov. 2011; 141(2): 152-60.
Zhu, X., et al. Age-dependent fate and lineage restriction of single NG2 cells. Development Feb. 2011; 138(4): 745-53.
Zorzetto, M., et al. Complement Receptor 1 Gene Polymorphisms Are Associated with Idiopathic Pulmonary Fibrosis. Am J Respir Crit Care Med. Aug. 1, 2003; 168(3): 330-4.
Zorzetto, M., et al. Nod2/CARD15 gene polymorphisms in idiopathic pulmonary fibrosis. Sarcoidosis Vasc Diffuse Lung Dis. Oct. 2005; 22(3): 180-5.
Zuo, F., et al. Gene expression analysis reveals matrilysin as a key regulator of pulmonary fibrosis in mice and humans. Proc Natl Acad Sci USA. Apr. 30, 2002; 99(9): 6292-7.
Abe, R., et al. Peripheral Blood Fibrocytes: Differentiation Pathway and Migration to Wound Sites. J Immunol. Jun. 15, 2001; 166(12): 7556-62.
Acharya, P.S., et al., Fibroblast migration is mediated by CD44-dependent TGF beta activation. J Cell Sci. May 1, 2008; 121(Pt 9): 1393-402.
Ahn, M-H., et al. A promoter SNP rs4073T>A in the common allele of the interleukin 8 gene is associated with the development of idiopathic pulmonary fibrosis via the IL-8 protein enhancing mode. Respir Res. Jun 8, 2011; 12:73.
Altschul, P., et al. Gapped BLAST and PSI-BLAST: a new generation of protein database search programs. Nucleic Acids Res. 25:3389-3402 (1997).
Alvarez, D. F., et al. Lung microvascular endothelium is enriched with progenitor cells that exhibit vasculogenic capacity. Am J Physiol Lung Cell Mol Physiol. 2008; 294: L419-30.
Andersson-Sjoland, A., et al. Fibrocytes are a potential source of lung fibroblasts in idiopathic pulmonary fibrosis. Int J Biochem Cell Biol. 2008; 40(10) 2129-40.
Arch, R., et al. Participation in normal immune responses of a metastasis-inducing splice variant of CD44. Science. Jul. 31, 1992; 257(5070): 682-5.
Armanios, M.Y., et al. Telomerase Mutations in Families with Idiopathic Pulmonary Fibrosis. N Engl J Med. Mar. 29, 2007; 356(13): 1317-26.
Arora, R., et al. Multiple Roles and Interactions of Tbx4 and Tbx5 in Development of the Respiratory System. PLos Genet. 2012; 8(8): e1002866.
Astarita JL, et al. Podoplanin: emerging functions in development, the immune system, and cancer. Front Immunol. Sep. 12, 2012; vol. 3: Article 283, 1-11.
Baarsma, H.A., et al. Activation of WNT/b-Catenin Signaling in Pulmonary Fibroblasts by TGF-b1 Is Increased in Chronic Obstructive Pulmonary Disease. PLoS One. 2011; 6(9): e25450.
Balasubramaniam, V., et al. Bone marrow-derived angiogenic cells restore lung alveolar and vascular structure after neonatal hyperoxia in infant mice. Am J Physiol Lung Cell Mol Physiol. 2010; 298: L315-L323.
Balestrini, J.L, et al. The mechanical memory of lung myofibroblastswz. Integr Biol (Camb). Apr. 2012; 4(4): 410-21.
Barkauskas, C. E., et al. Cellular Mechanisms of Tissue Fibrosis. 7. New insights into the cellular mechanisms of pulmonary fibrosis. Am J Physiol Cell Physiol. Jun. 1, 2014; 306(11): C987-96.
Barkauskas, C.E., et al. Type 2 alveolar cells are stem cells in adult lung. J Clin Invest. Jul. 2013; 123(7): 3025-36.
Bartel, DP, MicroRNAs: genomics, biogenesis, mechanism, and function. Cell 116(2):281-297 (2004).
Bellusci, S., et al. Fibroblast Growth Factor 10 (FGF10) and branching morphogenesis in the embryonic mouse lung. Development Dec. 1997; 124(23): 4867-78.
Bergers, G., et al. The role of pericytes in blood-vessel formation and maintenance. Neuro Oncol. Oct. 2005; 7(4): 452-64.
Bjermer, L., et al. Hyaluronan and type III procollagen peptide concentrations in bronchoalveolar lavage fluid in diopathic pulmonary fibrosis.Thorax. Feb. 1989; 44(2): 126-31.
Bolton, S.J., et al. Changes in Clara Cell 10 kDa Protein (CC10)-positive Cell Distribution in Acute Lung Injury Following Repeated Lipopolysaccharide Challenge in the Rat. Toxicol Pathol. Apr. 2008; 36(3): 440-8.
Bournazos, S., et al. Fcy Receptor IIIb (CD16b) Polymorphisms are Associated with Susceptibility to Idiopathic Pulmonary Fibrosis. Lung. Dec. 2010; 188(6): 475-81.
Brummelkamp, T.R. et al. (2002) A system for stable expression of short interfering RNAs in mammalian cells. Science 296:550-553.

(56) References Cited

OTHER PUBLICATIONS

Bucala R, et al. Circulating fibrocytes define a new leukocyte subpopulation that mediates tissue repair. Mol Med. 1994;1(1):71-81.

Bujak, M., et al. The role of Interleukin-1 in the pathogenesis of heart disease. Arch Immulon Ther Exp (Warsz). May-Jun. 2009; 57(3): 165-76.

Camenisch, T.D., et al. Disruption of hyaluronan synthase-2 abrogates normal cardiac morphogenesis and hyaluronan-mediated transformation of epithelium to mesenchyme. J Clin Invest. Aug. 2000; 106(3): 349-60.

Campbell H, et al. Calculation of the internal surface of a lung. Nature 17:117 (1952).

Zebra-Thomas JA, et al. T-box gene products are required for mesenchymal induction of epithelial branching in the embryonic mouse lung. Dev Dyn. 2003;226(1):82-90.

Chambers, R.C. Abnormal wound healing responses in pulmonary fibrosis: focus on coagulation signalling. Eur Respir Rev. 2008; 17(109): 130-137.

Chan, JH, et al. Antisense oligonucleotides: from design to therapeutic application. Clin. Exp. Pharmacol. Physiol. 33 (5-6): 533-40 (2006).

Chapman HA. Epithelial-mesenchymal interactions in pulmonary fibrosis. Annu Rev Physiol. 2011;73:413-435.

Checa, M., et al. MMP-1 polymorphisms and the risk of idiopathic pulmonary fibrosis. Hum Genet. Dec. 2008; 124(5): 465-72.

Chen, J-H., et al. Beta-Catenin Mediates Mechanically Regulated, Transforming Growth Factor-beta1-Induced Myofibroblast Differentiation of Aortic Valve Interstitial Cells. Arterioscler Thromb Vasc Biol. Mar. 2011; 31(3): 590-7.

Cherng, S., et al. Alpha-Smooth Muscle Actin (?-SMA) . J Am Sci. 2008: 4(4): 7-9.

Chiaramonte, M.G., An IL-13 inhibitor blocks the development of hepatic fibrosis during a T-helper type 2-dominated inflammatory response et al. J Clin Invest. Sep. 1999; 104(6): 777-85.

Chiaramonte, M.G., et al. Regulation and function of the interleukin 13 receptor a2 during a T helper cell type 2-dominant immune response J Exp Med. Mar. 17, 2003; 197(6): 687-701.

Chilosi, M., et al. Aberrant Wnt/beta-Catenin Pathway Activation in Idiopathic Pulmonary Fibrosis. Am J Pathol. May 2003; 162(5): 1495-502.

Cho, C. Y., et al., Dressing the Part. Dermatol Clin. Jan. 1998; 16(1): 25-47.

Chung, M.P. et al. Role of Repeated Lung Injury and Genetic Background in Bleomycin-Induced Fibrosis. Am J Respir Cell Mol Biol. Sep. 2003; 29(3 Pt 1): 375-80.

Chunn, J. L. et al. Partially adenosine deaminase-deficient mice develop pulmonary fibrosis in association with adenosine elevations. Am J Physiol Lung Cell Mol Physiol. Mar. 2006; 290(3): L579-87.

Clark, H., et al. The genetics of neonatal respiratory disease.Semin Fetal Neonatal Med. Jun. 2005; 10(3): 271-82.

Claverie and States. Information Enhancement Methods for Large Scale Sequence Analysis. Comput. Chem., 17:191-201 (1993).

Collard, H.R., et al. Changes in Clinical and Physiologic Variables Predict Survival in Idiopathic Pulmonary Fibrosis. Am J Respir Crit Care Med. Sep. 1, 2003; 168(5): 538-42.

Collard, H.R., et al. Acute Exacerbations of Idiopathic Pulmonary Fibrosis. Am J Respir Crit Care Med. Oct. 1, 2007; 176(7): 636-43.

Collard, H.R., et al. Plasma biomarker profiles in acute exacerbation of idiopathic pulmonary fibrosis. Am J Physiol Lung Cell Mol Physiol. Jul. 2010; 299(1): L3-7.

Condren, A.B., et al. Perivascular Mural Cells of the Mouse Choroid Demonstrate Morphological Diversity That Is Correlated to Vasoregulatory Function. PLoS One. 2013; 8(1): e53386.

Corpet, F., et al; "Multiple sequence alignment with hierarchical clustering"; Nucleic Acids Research 16:10881-90 (1988).

Cortez, D.M., et al. IL-17 stimulates MMP-1 expression in primary human cardiac fibroblasts via p38 MAPK- and ERK1/2-dependent C/EBP-beta , NF-kappaB, and AP-1 activation. Am J Physiol Heart Circ Physiol Dec. 2007; 293(6): H3356-65.

Crivellato, E. The role of angiogenic growth factors in organogenesis. Int J Dev Biol. 2011; 55(4-5): 365-75.

Cronkhite, J.T., et al. Telomere Shortening in Familial and Sporadic Pulmonary Fibrosis. Am J Respir Crit Care Med. Oct. 1, 2008; 178(7): 729-37.

Birmingham et al., Nat. Protoc. 2:2068-78 (2007).

Naito et al., Front. Genet. 3:102 (2012).

Laganà et al., Front. Bioeng. Biotechnol. 2:65 (2014).

Jana et al., Appl. Microbiol. Biotechnol. 65:649-57 (2004).

Kanasty et al., Nat. Mater. 12:967-77 (2013).

Lewis et al., Nat. Genet. 32:107-08 (2002).

Pandit et al., Am. J. Respir. Crit. Care Med. 182:220-29 (2010).

Xie et al., Am. J. Respir. Cell. Mol. Biol. 57:721-32 (2017).

Dr. Noble, Kumar et al., J. Allergy Clin. Immunol. 128:1077-85 (2011).

Liu et al., J. Exp. Med. 207:1589-97 (2010).

Garbuzenko et al., Intratracheal versus intravenous liposomal delivery of siRNA, antisense oligonucleotides and anticancer drug, Pharm. Res. 26:382-94 (2009).

Gutbeir et al., RNAi-mediated suppression of constitutive pulmonary gene expression by smallinterfering RNA in mice, Pulm. Pharmacol. Ther. 23:334-44 (2010).

Jensen et al., Spray drying of siRNA-containing PLGA nanoparticles intended for inhalation. J. Control. Release 142:138-45 (2010).

Merkel et aL, Nonviral siRNA Delivery to the Lung: Investigation of PEG-PEI Polyplexes and Their In Vivo Performance, Mol. Pharm. 6:1246-60 (2009).

Perl et al., Silencing of Fas, but not caspase-8, in lung epithelial cells ameliorates pulmonary apoptosis, inflammation, and neutrophil influx after hemorrhagic shock and sepsis, Am. J. Pathol. 167:1545-59 (2005).

Rosas-Taraco et al., Intrapulmonary Delivery of XCL1-Targeting Small Interfering RNA in Mice Chronically Infected with Mycobacterium tuberculosis, Am. J. Respir. Cell Mol. Biol. 41:136-45 (2009).

Wang et al., Attenuation of fibrosis in vitro and in vivo with SPARC siRNA, Arthritis Res. Ther. 12:R60 (2010).

\* cited by examiner

METHOD EFFECTIVE TO MODULATE EXPRESSION OF T-BOX PROTEIN 4 (TBX4) FOR REDUCING PROGRESSION OF LUNG FIBROSIS AFTER A LUNG INJURY

CROSS-REFERENCE TO RELATED APPLICATIONS

This application is a National Stage Application under 35 U.S.C. 371, of PCT International Patent Application No.: PCT/IB2016/056575, filed Nov. 1, 2016, which claims the benefit of priority to U.S. Provisional Application No. 62/232,854 filed Sep. 25, 2015, entitled "Identification and Function of TBX4 Resident Fibroblasts as a Major Source of Fibrotic Fibroblasts," the content of which is incorporated by reference in its entirety.

STATEMENT OF GOVERNMENT FUNDING

This invention was made with government support under P01 HL108793, R01 HL060539, and R01 HL122068, awarded by the National Institutes of Health. The government has certain rights in the invention.

FIELD OF THE INVENTION

The described invention generally relates to the pathogenesis of pulmonary fibrosis and therapeutics for treating the same.

BACKGROUND OF THE INVENTION

Anatomy and Physiology of the Lungs

The lungs comprise a pair of organs occupying the pulmonary cavities of the thorax, and are the organs of respiration in which aeration of the blood takes place. Normal human lungs weigh about 1 kg, of which 40% to 50% is blood. The lungs contain about 2.5 L of air at end expiration and 6 L of air at full inflation. In human lungs, the right lung is slightly larger than the left, because ⅔ of the heart is located on the left side of the body. The right lung is divided into three lobes (superior lobe, middle lobe, and inferior, or basal lobe), while the left lung is divided into two lobes (superior lobe and inferior, or basal lobe), and contains the cardiac notch, an indentation in the lung that surrounds the apex of the heart.

Each lung is surrounded by the pleura, which are double-layered serous membranes. The parietal pleura forms the outer layer of the membrane and is attached to the wall of the thoracic cavity; the visceral pleura forms the inner layer of the membrane covering the outer surface of the lungs. Between the parietal and visceral pleura is the pleural cavity, which creates a hollow space into which the lungs expand during inhalation. Serous fluid secreted by the pleural membranes lubricates the inside of the pleural cavity to prevent irritation of the lungs during breathing.

The lungs occupy the majority of the space within the thoracic cavity; they extend laterally from the heart to the ribs on both sides of the chest and continue posteriorly toward the spine. Each lung is roughly cone-shaped with the superior end of the lung forming the point of the cone and the inferior end forming the base. The superior end of the lungs narrows to a rounded tip known as the apex. The inferior end of the lungs, known as the base, rests on the dome-shaped diaphragm. The base of the lungs is concave, following the contours of the diaphragm.

Air enters the body through the nose or mouth and passes through the pharynx, larynx, and trachea. Prior to reaching the lungs, the trachea splits into the left and right bronchi, which are large, hollow tubes made of hyaline cartilage and lined with ciliated pseudostratified epithelium. The hyaline cartilage of the bronchi adds rigidity and prevents the bronchi from collapsing and blocking airflow to the lungs. The pseudostratified epithelium lines the inside of the hyaline cartilage. Each lung receives air from a single, large primary bronchus.

As the primary bronchi enter the lungs, they branch off into smaller secondary bronchi that carry air to each lobe of the lung. The secondary bronchi further branch into many smaller tertiary bronchi within each lobe. The secondary and tertiary bronchi improve the efficiency of the lungs by distributing air evenly within each lobe.

The pseudostratified epithelium that lines the bronchi contains many cilia and goblet cells. The goblet cells secrete mucus. The cilia move together to push mucus secreted by the goblet cells away from the lungs.

Particles of dust and even pathogens like viruses, bacteria, and fungi in the air entering the lungs stick to the mucus and are carried out of the respiratory tract, helping to keep the lungs clean and free of disease.

Many small bronchioles branch off from the tertiary bronchi. Bronchioles differ from bronchi both in size and in the composition of their walls. While bronchi have hyaline cartilage rings in their walls, bronchioles are comprised of elastin fibers and smooth muscle tissue. The tissue of the bronchiole walls allows the diameter of bronchioles to change to a significant degree. When the body requires greater volumes of air entering the lungs, such as during periods of physical activity, the bronchioles dilate to permit increased airflow. In response to dust or other environmental pollutants, the bronchioles can constrict to prevent pollution of the lungs.

The bronchioles further branch off into many tiny terminal bronchioles. Terminal bronchioles are the smallest air tubes in the lungs and terminate at the alveoli of the lungs. Like bronchioles, the terminal bronchioles are elastic, capable of dilating or contracting to control airflow into the alveoli.

The alveoli, the functional units of the lungs, permit gas exchange between the air in the lungs and the blood in the capillaries of the lungs. Alveoli are found in small clusters called alveolar sacs at the end of the terminal bronchiole. Each alveolus is a hollow, cup-shaped cavity surrounded by many fine capillaries. The alveolar epithelium covers >99% of the internal surface area of the lungs (Wang et al. Proc Natl Acad Sci USA. 2007 Mar. 13; 104(11): 4449-54).

Adult lungs are very complicated organs containing at least 40-60 different cell types including fibroblasts (McQualter & Bertoncello. Stem Cells. 2012 May; 30(5): 811-6).

The walls of each alveolus are lined with simple squamous epithelial cells known as alveolar cells, ciliated cells, secretory cells, mainly nonciliated bronchiolar secretory cells which express Secretoglobin 1A member 1 (Scgb1a1+ club cells) (Kidiyoor et al., Gene and Cell Therapy: Therapeutic Mechanisms and Strategies 761 (Nancy Smyth Templeton ed., 4$^{th}$ ed. 2015)), and mesenchymal cell types including resident fibroblasts, myofibroblasts, and perivascular cells that wrap around capillaries (pericytes) (Barkauskas & Noble. Am J Physiol Cell Physiol. 2014 Jun. 1; 306(11): C987-96). The term "club cells" as used herein refers to dome-shaped cells with short microvilli, found in the bronchioles of the lungs. Club cells are the epithelial progenitor cells of the small airways. Club cells were formerly known as "Clara cells." A thin layer of connective tissue underlies and supports the alveolar cells. Present within this connective tissue are fibroblasts, the least specialized cells in the connective tissue family, which are found dispersed in connective tissue throughout the body, and play a key role in the wound healing process (Alberts et al. Molecular Biology of the Cell. 4$^{th}$ Ed. New York: Garland Science; 2002. Fibroblasts and Their Transformations: The Connective-Tissue Cell Family, 1300-1301). Surrounding the connective tissue on the outer border of the alveolus are capillaries. A respiratory membrane is formed where the walls of a capillary touch the walls of an alveolus. At the respiratory membrane, gas exchange occurs freely between the air and blood through the extremely thin walls of the alveolus and capillary.

There are two major types of alveolar cells, type 1 alveolar epithelial cells (AEC1s), and type 2 alveolar epithelial cells (AEC2s). AEC1 s are large flat cells through which the exchange of $CO_2/O_2$ takes place; they cover approximately 95% of the alveolar surface, comprise approximately 40% of the alveolar epithelium, and 8% of the peripheral lung cells; in contrast, AEC2s are small, cuboidal cells that cover approximately 5% of the alveolar surface, comprise 60% of the alveolar epithelium, and 15% of the peripheral lung cells, and are characterized by their ability to synthesize and secrete surfactant protein C (SPC) and by the distinct morphological appearance of inclusion bodies known as lamellar bodies (Wang et al. Proc Natl Acad Sci USA. 2007 Mar. 13; 104(11): 4449-54; Barkauskas & Noble. Am J Physiol Cell Physiol. 2014 Jun. 1; 306(11): C987-96): AEC2s function: 1) to synthesize, store, and secrete surfactant, which reduces surface tension, preventing collapse of the alveolus; 2) to transport ions from the alveolar fluid into the interstitium, thereby minimizing alveolar fluid and maximizing gas exchange; 3) to serve as progenitor cells for AEC1s, particularly during reepithelialization of the alveolus after lung injury; and 4) to provide pulmonary host defense by synthesizing and secreting several complement proteins including C3 and C5 (Strunk et al. J Clin Invest. 1988; 81: 1419-1426; Rothman et al. J Immunol. 1990; 145: 592-598; Zhao et al. Int J Mol Med. 2000; 5: 415-419) as well as numerous cytokines and interleukins that modulate lymphocyte, macrophage, and neutrophil functions (Mason. Respirology. 2006 January; 11 Suppl: S12-5; Wang et al. Proc Natl Acad Sci USA. 2007 Mar. 13; 104(11): 4449-54).

Septal cells and macrophages are also found inside the alveoli. Septal cells produce alveolar fluid that coats the inner surface of the alveoli. Alveolar fluid is a surfactant that moistens the alveoli, helps maintain the elasticity of the lungs, and prevents the thin alveolar walls from collapsing. Macrophages in the alveoli keep the lungs clean and free of infection by capturing and phagocytizing pathogens and other foreign matter that enter the alveoli along with inhaled air.

The lungs receive air from the external environment through the process of negative pressure breathing, which requires a pressure differential between the air inside the alveoli and atmospheric air. Muscles surrounding the lungs, such as the diaphragm, intercostal muscles, and abdominal muscles, expand and contract to change the volume of the thoracic cavity. Muscles expand the thoracic cavity and decrease the pressure inside the alveoli to draw atmospheric air into the lungs, in a process known as inhalation or inspiration. Muscles contract the size of the thoracic cavity to increase the pressure inside of the alveoli and force air out of the lungs, in a process known as exhalation or expiration.

External respiration is the process of exchanging oxygen and carbon dioxide between the air inside the alveoli and the blood in the capillaries of the lungs. Air inside the alveoli contains a higher partial pressure of oxygen compared to that in the blood in the capillaries. Conversely, blood in the lungs' capillaries contains a higher partial pressure of carbon dioxide compared to that in the air in the alveoli. These partial pressures cause oxygen to diffuse out of the air and into the blood through the respiratory membrane. At the same time, carbon dioxide diffuses out of the blood and into the air through the respiratory membrane. The exchange of oxygen into the blood and carbon dioxide into the air allows the blood leaving the lungs to provide oxygen to the body's cells, while depositing carbon dioxide waste into the air.

The lungs are a frequent target of infection, including those caused by viruses, bacteria, or fungal organisms, and are subject to myriad diseases and conditions. Lung diseases affecting the airways include, without limitation, asthma (an inflammatory disease of the lungs characterized by reversible (in most cases) airway obstruction), bronchitis (inflammation of the mucous membrane of the bronchial tubes), chronic obstructive pulmonary disease (general term used for those diseases with permanent or temporary narrowing of small bronchi, in which forced expiratory flow is slowed, especially when no etiologic or other more specific term can be applied), cystic fibrosis (a congenital metabolic disorder in which secretions of exocrine glands are abnormal, excessively viscid mucus causes obstruction of passageways, and the sodium and chloride content of sweat are increased throughout the patient's life), and emphysema (a lung condition characterized by increase beyond the normal in the size of air spaces distal to the terminal bronchiole (those parts containing alveoli), with destructive changes in their walls and reduction in their number).

Lung diseases affecting the alveoli include, without limitation, acute respiratory distress syndrome (acute lung injury from a variety of causes, characterized by interstitial and/or alveolar edema and hemorrhage as well as perivascular pulmonary edema associated with hyaline membrane formation, proliferation of collagen fibers, and swollen epithelium with increased pinocytosis), emphysema, lung cancer (any of various types of malignant neoplasms affecting the lungs), pneumonia (inflammation of the lung parenchyma characterized by consolidation of the affected part, the alveolar air spaces being filled with exudate, inflammatory cells, and fibrin), pulmonary edema (an accumulation of an excessive amount of watery fluid in cells or intercellular tissues affecting the lungs, usually resulting from mitral stenosis or left ventricular failure), pneumoconiosis (inflammation commonly leading to fibrosis of the lungs caused by the inhalation of dust incident to various occupations), and tuberculosis (a specific disease caused by infection by *Mycobacterium tuberculosis*, the tubercle *bacillus*, which can affect almost any tissue or organ of the body, the most common seat of the disease being the lungs).

Lung diseases affecting the interstitium, the thin lining between the alveoli, include, without limitation, pneumonia, pulmonary edema, and interstitial lung disease, a broad collection of lung conditions including, without limitation, autoimmune diseases (disorders in which the loss of function or destruction of normal tissue arises from humoral or cellular immune responses to the body's own tissue constituents), idiopathic pulmonary fibrosis (an acute to chronic inflammatory process or interstitial fibrosis of the lung of unknown etiology), and sarcoidosis (a systemic granulomatous disease of unknown cause, especially involving the lungs with resulting interstitial fibrosis, but also involving lymph nodes, skin, liver, spleen, eyes, phalangeal bones, and parotid glands).

Lung diseases affecting blood vessels of the lung include, without limitation, pulmonary embolism (obstruction or occlusion of pulmonary arteries by an embolus, most frequently by detached fragments of thrombus from a leg or pelvic vein) and pulmonary hypertension (high blood pressure in the pulmonary circuit).

Lung diseases affecting the pleura include, without limitation, pleural effusion (increased fluid within the pericardial sac), pneumothorax (the presence of free air or gas in the pleural cavity), and mesothelioma (a rare neoplasm derived from the lining of the cells of the pleura and peritoneum which grows as a thick sheet covering the viscera, and is composed of spindle cells or fibrous tissue which may enclose glandlike spaces lined by cuboidal cells).

Lung diseases affecting the chest wall include, without limitation, obesity hypoventilation syndrome (a combination of severe, grotesque obesity, somnolence, and general debility, theoretically resulting from hypoventilation induced by the obesity) and neuromuscular disorders, including, without limitation, amyotrophic lateral sclerosis (a fatal degenerative disease involving the corticobulbar, corticospinal, and spinal motor neurons, manifested by progressive weakness and wasting of muscles innervated by the affected neurons) and myasthenia gravis (a disorder of neuromuscular transmission marked by fluctuating weakness and fatigue of certain voluntary muscles, including those innervated by brainstem motor nuclei).

Regenerative Cells of the Lungs

The adult lung comprises at least 40-60 different cell types of endodermal, mesodermal, and ectodermal origin, which are precisely organized in an elaborate 3D structure with regional diversity along the proximal-distal axis. In addition to the variety of epithelial cells, these include cartilaginous cells of the upper airways, airway smooth muscle cells, interstitial fibroblasts, myofibroblasts, lipofibroblasts, and pericytes as well as vascular, microvascular, and lymphatic endothelial cells, and innervating neural cells. The regenerative ability of lung epithelial stem/progenitor cells in the different regions of the lung are thought to be determined not only by their intrinsic developmental potential but also by the complex interplay of permissive or restrictive cues provided by these intimately associated cell lineages as well as the circulating cells, soluble and insoluble factors and cytokines within their niche microenvironment (McQualter & Bertoncello. Stem Cells. 2012 May; 30(5); 811-16).

The crosstalk between the different cell lineages is reciprocal, multidirectional, and interdependent. Autocrine and paracrine factors elaborated by mesenchymal and endothelial cells are required for lung epithelial cell proliferation and differentiation (Yamamoto et al. Dev Biol. 2007 Aug. 1; 308(1) 44-53; Ding et al. Cell. 2011 Oct. 28; 147(3): 539-53), while endothelial and epithelial cell-derived factors also regulate mesenchymal cell proliferation and differentiation, extracellular matrix deposition and remodeling, and adhesion-mediated signaling (Crivellato. Int J Dev Biol. 2011; 55(4-5): 365-75); Grinnell & Harrington. Pulmonary endothelial cell interactions with the extracellular matrix. In: Voelkel N F, Rounds S, eds. The Pulmonary Endothelium: Function in Health and Disease. Chichester, West Suxssex: Wiley-Blackwell, 2009: 51-72). Chemotactic factors elaborated by these cell lineages also orchestrate the recruitment of inflammatory cells, which participate in the remodeling of the niche and the regulation of the proliferation and differentiation of its cellular constituents (McQualter & Bertoncello. Stem Cells. 2012 May; 30(5); 811-16).

Lung Mesenchymal Stem/Progenitor Cells

Tracheal and distal embryonic lung mesenchyme have been demonstrated to have inductive properties for the regional specification of the embryonic epithelium (Shannon & Deterding. Epithelial-mesenchymal interactions in lung development. In: McDonald J A, ed. Lung Biology in Health and Disease. Vol. 100. New York: Marcel Dekker Inc, 1997, pp. 81-118.). During lung development, mesenchymal stromal cells at the distal tip of the branching epithelium are known to secrete fibroblast growth factor (FGF)-10, which influences the fate and specificity of early lung epithelial progenitor cells (Bellusci et al. Development. 1997 December; 124(23): 4867-78; Ramasamy et al. Dev Biol. 2007 Jul. 15; 307(2): 237-47). FGF-10 is a component of a multifaceted epithelial-mesenchymal cell signaling network involving BMP, Wnt, and Shh pathways which coordinate the proliferation and differentiation of progenitor cells in the developing lung (reviewed in Morrisey & Hogan. Dev Cell. 2010 Jan. 19; 18(1): 8-23). Lineage tracing studies have also revealed that FGF-10$^{pos}$ mesenchymal cells residing at the branching tip of the epithelium function as stem/progenitor cells for smooth muscle cells, which become distributed along the elongating airways (De Langhe et al. Dev Biol. 2006 Nov. 1; 299(1): 52-62; Mailleuix et al. Development. 2005 May; 132(9): 2157-66). In other studies, mesenchymal stromal cells adjacent to the trachea and extrapulmonary bronchi have also been shown to give rise to bronchiolar smooth muscle cells (Shan et al. Dev Dyn. 2008; 237: 750-5). Collectively, these studies suggest that at least two distinct populations of mesenchymal stromal cells endowed with epithelial modulating properties emerge during development.

Several studies have identified resident mesenchymal stromal cells in adult lungs with the capacity for adipogenic, chondrogenic, osteogenic, and myogenic differentiation. These cells have been clonally expanded from heterogeneous populations of mixed lineage cells defined by their ability to efflux Hoechst 33342 (Giangreco et al. Am J Physiol Lung Cell Mol Physiol. 2004; 286: L624-30; Summer et al. Am J Respir Cell Mol Biol. 2007; 37: 152-9), by their capacity for outgrowth from lung explant cultures (Hoffman et al. Stem Cells Dev. 2011; 20: 1779-92) or by their characteristic expression of Sca-1 (McQualter et al. Stem Cells. 2009; 27: 612-22; Hegab et al. Stem Cells Dev. 2010; 19: 523-36). In addition, further enrichment of CD45$^{neg}$CD31$^{neg}$Sca-1$^{pos}$ mesenchymal stromal cells has been achieved based on their lack of EpCAM expression, which selectively labels epithelial lineage cells (McQualter et al. Proc Natl Acad Sci USA 2010; 107: 1414-19). Resolution of the mesenchymal and epithelial lineages has revealed that the endogenous lung mesenchymal stromal cell population is necessary and sufficient to support the proliferation and differentiation of bronchiolar epithelial stem/progenitor cells in coculture (Id.). This suggests that adult mesenchymal stromal cells share similar epithelial inductive properties to their embryonic counterparts and are an important element of the epithelial stem/progenitor cell niche in the adult lung. This concept is also supported by recent in vivo studies showing that following naphthalene injury of club cells, parabronchial mesenchymal cells secrete FGF-10 to support epithelial regeneration from surviving epithelial stem/progenitor cells (Volckaert et al. J Clin Invest. 2011; 121: 4409-19).

Lung Endothelial Progenitor Cells

Endothelial-epithelial cell interactions and angiogenic and angiocrine factors elaborated in the lung epithelial stem/progenitor cell microenvironment also play a role in the regulation of endogenous lung epithelial stem/progenitor cell regeneration and repair (Yamamoto et al. Dev Biol. 2007 Aug. 1; 308(1) 44-53; Ding et al. Cell. 2011 Oct. 28; 147(3): 539-53; Crivellato. Int J Dev Biol. 2011; 55(4-5): 365-75); Grinnell & Harrington. Pulmonary endothelial cell interactions with the extracellular matrix. In: Voelkel N F, Rounds S, eds. The Pulmonary Endothelium: Function in Health and Disease. Chichester, West Suxssex: Wiley-Blackwell, 2009: 51-72). For example, it has been reported that the coculture of human vascular endothelial cells with a human bronchial epithelial cell line promotes the generation of branching bronchioalveolar epithelial structures in a 3D culture system (Frazdottir et al. Respir Res. 2010; 11: 162). While considerable progress has been made in understanding the heterogeneity, functional diversity, and pathophysiological behavior of lung vascular and microvascular endothelial cells, the immunophenotypic profiling, quantitation, and functional analysis of lung endothelial progenitor cells (EPC) lags far behind. As for EPC derived from human umbilical cord blood, bone marrow, and mobilized peripheral blood (Timmermans et al. J Cell Mol Med. 2009; 13: 87-102), the rarity of EPC in the lung, their lack of distinguishing markers, and the inability to discriminate circulating EPC and tissue resident EPC have been major impediments in assessing the contribution of endogenous lung EPC in lung vascular repair, and lung regeneration and remodeling (Thebaud & Yoder. Pulmonary endothelial progenitor cells. In: Voelkel N F, Rounds S, eds. The Pulmonary Endothelium: Function in Health and Disease. Chichester, West Sussex: Wiley, 2009: 203-16; Yoder. Proc Am Thorac Soc. 2011; 8: 466-70).

Lung macrovascular and microvascular endothelial cells can be resolved on the basis of their preferential binding to the lectins *Helix pomatia* and *Griffonia simplicifolica*, respectively (King et al. Microvasc Res. 2004; 67: 139-51), but there are no other cell surface markers that can discriminate mature lung endothelial cells and EPC (Yoder. Proc Am Thorac Soc. 2011; 8: 466-70). In addition, the rarity of EPC has necessitated the ex vivo expansion and passaging of adherent heterogeneous rat (Alvarez et al. Am J Physiol Lung Cell Mol Physiol. 2008; 294: L419-30) or mouse (Schniedermann et al. BMC Cell Biol. 2010; 11:50) lung endothelial cells in liquid culture prior to quantitation and flow cytometric and functional analysis of lung-derived EPC in in vitro assays. These assays suggest that the lung microvasculature is a rich source of EPC. However, the incidence, immunophenotypic and functional properties of EPC in the primary explanted endothelial cells compared with their ex vivo manipulated, selected, and expanded counterparts remains indeterminate. The ability of these endogenous lung EPCs to contribute to vascular repair and remodeling in vivo is also unproven (Yoder. Proc Am Thorac Soc. 2011; 8: 466-70). Recent studies suggest it likely that both circulating EPC and resident lung EPC contribute to endothelial cell regeneration and repair (Balasubramian et al. Am J Physiol Lung Cell Mol Physiol. 2010; 298: L315-23; Duong et al. Angiogenesis. 2011: 411-22; Chamoto et al. Am J Respir Cell Mol Biol. 2012 March; 46(3): 283-9).

General Principles of Wound Healing

The term "wound healing" refers to the processes by which the body repairs trauma to any of its tissues, especially those caused by physical means and with interruption of continuity.

A wound-healing response can be viewed as comprising four separate phases, comprising: 1) an initial phase post injury involving hemostasis; 2) a second phase involving inflammation; 3) a third phase involving granulation and proliferation; and 4) a fourth phase involving remodeling and maturation. The culmination of the wound-healing response results in the replacement of normal tissue structures with fibroblastic mediated scar tissue. Processes involved in the wound healing response, however, can go awry and produce an exuberance of fibroblastic proliferation, which can result in tissue damage, including hypertrophic scarring (a widened or unsightly scar that does not extend the original boundaries of the wound).

Initial Phase—Hemostasis

An initial injury results in an outflow of blood and lymphatic fluid. This is also the process during which the initial reparative blood clot is created. Both the intrinsic coagulation pathways, so called because all of the components are intrinsic to plasma, and the extrinsic coagulation pathways are activated. The intrinsic and extrinsic systems converge to activate the final common pathways causing fibrin formation. FIG. 1 shows an illustrative representation of the classical coagulation cascades. It is generally recognized that these systems function together and interact in vivo.

The intrinsic coagulation pathway is initiated when blood contacts any surface except normal endothelial and blood cells. This pathway, also known as the contact activation pathway, begins with formation of the primary complex on collagen by high-molecular weight kininogen (HMWK), prekallikrein, and coagulation factor (Factor) XII (Hageman factor). Prekallikrein is converted to kallikrein and Factor XII becomes Factor XIIa. Factor XIIa converts Factor XI into Factor XIa. Factor XIa activates Factor IX, which, with its co-factor FVIIIa form the tenase complex, which activates Factor X to Factor Xa.

The extrinsic coagulation pathway, also known as the tissue factor pathway, generates a thrombin burst and is initiated when tissue thromboplastin activates Factor VII. Upon vessel injury, tissue factor (TF), a nonenzymatic lipoprotein cofactor that greatly increases the proteolytic efficiency of Factor VIIa, is exposed to the blood and enzyme coagulation factor VII (proconvertin) circulating in the blood. Once bound to TF, Factor VII is activated to Factor VIIa by different proteases, including thrombin (Factor IIa), Factors Xa, IXa, XIIa and the Factor VIIa-TF complex itself. The Factor VIIa-TF complex activates Factors IX and X. The activation of Factor Xa by the Factor VIIa-TF complex almost immediately is inhibited by tissue factor pathway inhibitor (TFPI). Factor Xa and its cofactor Va form the prothrombinase complex which activates the conversion of prothrombin to thrombin. Thrombin then activates other components of the coagulation cascade, including Factors V and VIII (which activates Factor XI, which, in turn, activates Factor IX), and activates and releases Factor VIII from being bound to von Willebrand Factor (vWF). Factors VIIa and IXa together form the "tenase" complex, which activates Factor X, and so the cycle continues.

As currently understood, coagulation in vivo is a 3-step process centered on cell surfaces. FIG. 2 shows an illustration of the cell-surface based model of coagulation in vivo (Monroe Arterioscler Thromb Vasc Biol. 2002; 22:1381-1389). In the first step, coagulation begins primarily by initiation with tissue factor, which is present on the subendothelium, tissues not normally exposed to blood, activated monocytes and endothelium when activated by inflammation. Factors VII and VIIa bind to tissue factor and adjacent collagen. The factor VIIa-tissue factor complex activates factor X and IX. Factor Xa activates factor V, forming a prothrombinase complex (factor Xa, Va and calcium) on the tissue factor expressing cell. In the second step, coagulation is amplified as platelets adhere to the site of injury in the blood vessel. Thrombin is activated by platelet adherence and then acts to fully activate platelets, enhance their adhesion and to release factor V from the platelet a granules. Thrombin on the surface of activated platelets activates factors V, VIII and XI, with subsequent activation of factor IX. The tenase complex (factors IXa, VIIIa and calcium) now is present on platelets where factor Xa can be produced and can generate another prothrombinase complex on the platelet so that there can be large-scale production of thrombin. Propagation, the third step, and is a combination of activation of the prothrombinase complexes that allow large amounts of thrombin to be generated from prothrombin. More platelets can be recruited, as well as activation of fibrin polymers and factor XIII.

The inflammatory phase (see below) begins during the hemostasis phase. Thrombocytes, as well as recruited white blood cells, release numerous factors to ramp up the healing process. Alpha-granules liberate platelet-derived growth factor (PDGF), platelet factor IV, and transforming growth factor beta (TGF-β). The processes of inflammation, collagen degradation and collagenogenesis, myoblastic creation from transformed fibroblasts, growth of new blood vessels, and reepithelialization are mediated by a host of cytokines and growth factors. The interleukins strongly influence the inflammatory process. Vascular endothelial growth factor (VEGF) and other factors enhance blood vessel formation, and some have multiple roles, such as fibroblast growth factor (FGF)-2, which affects not only the process of angiogenesis but also that of reepithelialization. Vasoactive amines, such as histamine and serotonin, are released from dense bodies found in thrombocytes. PDGF is chemotactic for fibroblasts and, along with TGF-β, is a potent modulator of fibroblastic mitosis, leading to prolific collagen fibril construction in later phases. Fibrinogen is cleaved into fibrin, and the framework for completion of the coagulation process is formed. Fibrin provides the structural support for cellular constituents of inflammation. This process starts immediately after the insult and may continue for a few days.

Second Phase: Inflammation

The early component of the inflammatory phase is predominated by the influx of the polymorphonuclear leukocytes (PMNs) and the later component of the inflammatory phase is predominated by monocytes/macrophages.

Within the first 6-8 hours, PMNs engorge the wound. TGF-β facilitates PMN migration from surrounding blood vessels, from which they extrude themselves from these vessels. These cells cleanse the wound, clearing it of debris. The PMNs attain their maximal numbers in 24-48 hours and commence their departure by hour 72. Other chemotactic agents are released, including FGF, TGF-β and TGF-α, PDGF, and plasma-activated complements C3a and C5a (anaphylactic toxins). They are sequestered by macrophages or interred within the scab or eschar (Id.; Habif. Dermatologic surgical procedures. Clinic Dermatology: A Color Guide to Diagnosis and Therapy. $3^{rd}$ ed. 1996. 809-810).

As the process continues, monocytes also exude from surrounding blood vessels. Once they leave the vessel, these are termed macrophages. The macrophages continue the cleansing process, manufacture various growth factors during days 3-4, and orchestrate the multiplication of endothelial cells with the sprouting of new blood vessels, the duplication of smooth muscle cells, and the creation of the milieu created by the fibroblast. Many factors influencing the wound healing process are secreted by macrophages, including TGFs, cytokines and interleukin (IL)-1, tumor necrosis factor (TNF), and PDGF.

Third Phase: Granulation and Proliferation

The granulation and proliferation phase consists of an overall and ongoing process, comprising subphases termed the "fibroplasia, matrix deposition, angiogenesis and re-epithelialization" subphases (Cho & Lo. Dermatol Clin. 1998 January; 16(1): 25-47).

By days 5-7, fibroblasts have migrated into the wound, laying down new collagen of subtypes I and III. Early in normal wound healing, type III collagen predominates but is later replaced by type I collagen.

Tropocollagen is the precursor of all collagen types and is transformed within the cell's rough endoplasmic reticulum, where proline and lysine are hydroxylated. Disulfide bonds are established, allowing 3 tropocollagen strands to form a triple left-handed triple helix, termed procollagen. As the procollagen is secreted into the extracellular space, peptidases in the cell membrane cleave terminal peptide chains, creating true collagen fibrils.

The wound is suffused with glycosaminoglycans (GAGs) and fibronectin produced by fibroblasts. These GAGs include heparin sulfate, hyaluronic acid, chondroitin sulfate, and keratin sulfate. Proteoglycans are GAGs that are bonded covalently to a protein core and contribute to matrix deposition.

Angiogenesis results from parent vessel offshoots. The formation of new vasculature requires extracellular matrix and basement membrane degradation followed by migration, mitosis, and maturation of endothelial cells. Basic FGF and vascular endothelial growth factor are believed to modulate angiogenesis.

Re-epithelization occurs with the migration of cells from the periphery of the wound and accessory or adjoining tissues. This process commences with the spreading of cells within 24 hours. Division of peripheral cells occurs in hours 48-72, resulting in a thin epithelial cell layer, which bridges the wound. Epidermal growth factors are believed to play a key role in this aspect of wound healing.

This succession of subphases can last up to 4 weeks in the clean and uncontaminated wound.

Fourth Phase: Remodeling and Maturation

After the third week, the wound undergoes constant alterations, known as remodeling, which can last for years after the initial injury occurred. Collagen is degraded and deposited in an equilibrium-producing fashion, resulting in no change in the amount of collagen present in the wound. The collagen deposition in normal wound healing reaches a peak by the third week after the wound is created. Contraction of the wound is an ongoing process resulting in part from the proliferation of specialized fibroblasts termed myofibroblasts, which provide mechanical support and integrity to the tissue after initial injury. Wound contraction occurs to a greater extent with secondary healing (i.e., healing by second intention, which describes a wound left open and allowed to close by reepithelialization and contraction by myofibroblasts) than with primary healing (i.e., healing by first intention, which describes a wound closed by approximation of wound margins or by placement of a graft or flap, or wounds created and closed in the operating room, unlike via reepithelialization and contraction by myofibroblasts). Maximal tensile strength (the greatest longitudinal stress a substance can bear without tearing apart) of the wound is achieved by the 12th week, and the ultimate resultant scar has only 80% of the tensile strength of the original skin that it has replaced. At the end of tissue repair, the reconstructed ECM takes over the mechanical load and myofibroblasts disappear by massive apoptosis (Tomasek et al. Nat Rev Mol Cell Biol. 2002 May; 3(5): 349-63).

Fibroblastic Cells and Myofibroblast Differentiation in Normal Conditions

Under normal conditions, fibroblastic cells exhibit few or no actin-associated cell-cell and cell-matrix contacts and little ECM production (Tomasek et al. Nat Rev Mol Cell Biol. 2002 May; 3(5): 349-63), but after tissue injury, they become activated to migrate into the damaged tissue and to synthesize ECM components (Hinz. J Invest Dermatol. 2007 March; 127(3): 526-37) by cytokines locally released from inflammatory and resident cells (Werner & Grose. Physiol Rev. 2003 July; 83(3): 835-70) or from malignant epithelial cells (De Wever & Mareel. J Pathol. 2003 July; 200(4): 429-47).

Another important stimulus for this phenotypic transition is the change of the mechanical microenvironment; whereas fibroblasts in intact tissue are generally stress-shielded by the crosslinked ECM, this protective structure is lost in the continuously remodeled ECM of injured tissue (Tomasek et al. Nat Rev Mol Cell Biol. 2002 May; 3(5): 349-63). In response to mechanical challenge, fibroblasts acquire contractile stress fibers that are first composed of cytoplasmic actins (Tomasek et al. Nat Rev Mol Cell Biol. 2002 May; 3(5): 349-63), hallmarking the "protomyofibroblast." Stress fibers are connected to fibrous ECM proteins at sites of integrin-containing cell-matrix junctions (Hinz. Eur J Cell Biol. 2006 April; 85(3-4): 175-81) and between cells via de novo established N-cadherin-type adherens junctions (Hinz et al. Mol Biol Cell. 2004 September; 15(9): 4310-20).

In culture, protomyofibroblasts are a stable phenotype, representing an intermediate step in most in vivo conditions where they proceed toward the "differentiated myofibroblast" that is characterized by de novo expression of α-smooth muscle actin (α-SMA), its most commonly used molecular marker, and by increased production of ECM proteins. Expression of α-SMA in stress fibers confers to the differentiated myofibroblast at least a twofold stronger contractile activity compared with α-SMA-negative fibroblasts in culture (Hinz et al. Am J Pathol. 2007 June; 170(6): 1807-16).

At least three local events are needed to generate α-SMA-positive differentiated myofibroblasts: 1) accumulation of biologically active transforming growth factor (TGF) β1; 2) the presence of specialized ECM proteins like the ED-A splice variant of fibronectin; and 3) high extracellular stress, arising from the mechanical properties of the ECM and cell remodeling activity (Tomasek et al. Nat Rev Mol Cell Biol. 2002 May; 3(5): 349-63). Mechanoperception is mediated by specialized cell-matrix junctions, called "fibronexus" in vivo and "supermature focal adhesions" (FAs) in vitro (Hinz. Eur J Cell Biol. 2006 April; 85(3-4): 175-81). Analogously, small N-cadherin-type cell-cell adhesions develop into larger OB-cadherin (cadherin-11)-type junctions during generation of the differentiated myofibroblast in vitro and in vivo (Hinz et al. Mol Biol Cell. 2004 September; 15(9): 4310-20; Hinz et al. Am J Pathol. 2007 June; 170(6): 1807-16).

The main myofibroblast inducer TGFβ1 up-regulates expression of fibronectin and its integrin receptors in lung fibroblasts; this is closely linked to the activation/phosphorylation of focal adhesion kinase essential for the induction of myofibroblast differentiation (Thannickal et al. J Biol Chem. 2003 Apr. 4; 278(14): 12384-9). At the end of tissue repair, the reconstructed ECM again takes over the mechanical load and myofibroblasts disappear by massive apoptosis (Tomasek et al. Nat Rev Mol Cell Biol. 2002 May; 3(5): 349-63); stress release is a powerful promoter of myofibroblast apoptosis in vivo (Hinz et al. Am J Pathol. 2007 June; 170(6): 1807-16).

After injury, the main myofibroblast progenitor appears to be the locally residing fibroblast, which transiently differentiates into a protomyofibroblast, characterized by α-SMA-negative stress fibers. In the lung, the epithelial-mesenchymal transition ("EMT"), the biologic process that allows an epithelial cell to undergo multiple biochemical changes that enable it to assume a mesenchymal cell phenotype (Kalluri & Weinberg. J Clin Invest. 2009 Jun. 1; 119(6): 1420-28)), may provide an additional mechanism to generate fibroblasts (Hinz et al. Am J Pathol. 2007 June; 170(6): 1807-16).

Pulmonary Fibrosis

Pulmonary fibrosis, an interstitial lung disease, is a general term used to describe an increased accumulation of extracellular matrix ("ECM") in the distal lung, rendering the lung stiff and compromising its ability to facilitate normal gas exchange. Patients typically present with the insidious onset of shortness of breath with exertion as the disease often goes unnoticed in its early stages. Pulmonary fibrosis can be associated with a number of underlying diseases (such as connective tissue/rheumatologic disease) or environmental exposures (asbestosis), or it can be idiopathic, i.e., of unknown cause, in nature (Barkauskas & Nobel. Am J Physiol Cell Physiol. 2014 Jun. 1; 306(11): C987-96).

Progressive tissue fibrosis is a major cause of morbidity, and idiopathic pulmonary fibrosis (IPF) is a terminal illness characterized by unremitting ECM deposition in the lung with very limited choice of therapies (Noble et al. J Clin Invest. 2012 August; 122(8): 2756-62). Although certain mediators have been identified as initiating progressive fibrosis, the mechanisms that contribute to the disease are unknown.

IPF, a chronic, terminal disease that manifests over several years, is the most common form of fibrotic lung disease with a prevalence of 14.0-42.7 cases per 100,000 individuals in the United States (depending on the case definition used) and a median survival of 2.5-3.5 yr (Raghu et al. Am J Respir Crit Care Med. 2006 Oct. 1; 174(7): 810-6). It is characterized by excess ECM components and scar tissue within the lungs, and exercise-induced breathlessness and chronic dry cough are the prominent symptoms. IPF is viewed as a disease of aging, with the median age at diagnosis being in the mid-60s. There are few effective therapies for IPF short of lung transplant (Meltzer and Nobel. Orphanet J Rare Dis. 2008 Mar. 26; 3: 8. Doi: 10,1186/1750-1172-3-8). Because a pharmacologic therapy capable of halting or at least slowing the progression of the disease has been elusive, there are intense efforts to better understand the factors that trigger and perpetuate this disease.

IPF belongs to a family of lung disorders known as interstitial lung diseases ("ILD"), or more accurately, the diffuse parenchymal lung diseases ("DPLD"). Within this broad category of diffuse lung diseases, IPF belongs to the subgroup known as idiopathic interstitial pneumonia ("IIP"). By definition, the etiology of IIP is unknown. There are seven distinct IIPs, differentiated by specific clinical features and pathological patterns (Katzenstein et al. Am J Respir Crit Care Med. 2008 April; 157(4 Pt 1): 1301-15). IPF is the most common form of IIP, and is associated with the pathologic pattern known as usual interstitial pneumonia (UIP). The UIP pattern of fibrosis is characterized by two features: 1) Spatial or geographic heterogeneity, which refers to a patchy distribution of dense lung scarring with areas of less affected or normal lung tissue; and 2) Temporal heterogeneity, which refers to areas of densely collagenized fibrosis with variable smooth muscle proliferation alternating with active fibroblast foci (Smith et al. J Clin Pathol. 2013 October; 66(1): 896-903). Therefore, IPF is often referred to as IPF/UIP. IPF is usually fatal, with an average survival of approximately three years from the time of diagnosis (Collard et al. Am J Respir Crit Care Med. 2003 Sep. 1; 168(5): 538-42; Flaherty, et al. Am J Respir Crit Care Med. 2003 Sep. 1; 168(5): 543-8; Latsi et al. Am J Respir Crit Care Med. 2003 Sep. 1; 168(5): 531-7).

IPF arises in the alveolar regions of the lung, a region that consists of AEC2s, and AEC1s, as well as a number of mesenchymal cell types. It is hypothesized that cross talk between the alveolar epithelium and its associated mesenchyme is dysregulated in IPF pathogenesis, and this leads to the unchecked proliferation of extracellular matrix-producing cells. Evidence from genetic analysis of rare familial cases of IPF suggests that defects that incite the development of the disease can originate in the alveolar epithelium (Barkauskas & Noble. Am J Physiol Cell Physiol. 2014 June 1; 306(11): C987-96).

Examples of non-medication based interventions for IPF include pulmonary rehabilitation, long-term oxygen therapy, mechanical ventilation, and lung transplantation. Of these treatments, the only intervention that improves survival in select patients with IPF is lung transplantation (Rafii et al. J Thorac Dis. 2013; 5(1): 48-73). However, lung transplantation is not without significant risks, including infection, given the need for immunosuppression, acute and chronic graft rejection, and airway stenosis (Id.).

Many proposed medication based treatments have failed to date (Id.). These include anti-inflammatory or immunomodulatory therapies, such as corticosteroid monotherapy, azathioprine, cyclophosphamide, everolimus; anticoagulants and therapies targeting the coagulation cascade, such as warfarin, heparin, and prednisolone; endothelin receptor antagonists and vasodilators, such as bosentan, ambrisentan, macitentan, and sildenafil; and antifibrotics and cytokine/kinase inhibitors, such as interferon-gamma, etanercept, imatinib, and CC-930 (Id.). Many of these failures have been associated with a high degree of side effects, which would be expected for medications of these classes, and limited therapeutic effects.

To date, two therapeutic medications have been FDA approved for the treatment of IPF. Esbriet® (pirfenidone), a small molecule antifibrotic that acts on multiple pathways, including the transforming growth factor beta (TGF-β) pathway, and Ofev® (nintedanib), a small molecule inhibitor of the receptors for tyrosine kinases, fibroblast growth factor (FGF), platelet-derived growth factor (PDGF), and vascular endothelial growth factor (VEGF). Although these medications have side effects and do not appear to be able to reverse IPF, they have been shown to significantly slow the progression of the disease.

Recently, microRNAs have shown promise as a therapeutic tool in the treatment of IPF. MicroRNAs (miRNAs) include a broad class of small evolutionarily conserved noncoding RNAs that have important roles in a variety of patho-physiological processes by blocking translation or promoting degradation of complementary target mRNAs (Wynn & Ramalingam. Nat Med. 2012 Jul. 6; 18(7): 1028-40). Although unique subsets of miRNAs have been identified in various fibrotic diseases, a much smaller subset of miRNAs have emerged as regulators of the fibrotic process. For example, miR-21 is expressed in the lungs of individuals with IPF, and mice treated with miR-21 antisense probes were protected from bleomycin-induced pulmonary fibrosis (Liu et al. J Exp Med. 2010 Aug. 2; 207(8): 1589-97). Mechanistically, miR-21 is thought to promote fibrosis by regulating TGF-β1 and MAP kinase signaling in activated myofibroblasts (Id), and miR-29 also seems to promote fibrosis in human cells by directly regulating type I collagen expression (Ogawa et al. Biochem Biophys Res Commun. 2010 Jan. 1; 391(1): 316-21). In addition, miR-29 has been found to be down regulated in various forms of fibrosis, including IPF. Animal studies injecting a miR-29 mimic into mice has demonstrated promising results even in cases of "established fibrosis." (Fox. Drug Discovery & Development http://www.dddmag.com/news/2014/10/reversing-idiopathic-pulmonary-fibrosis).

Wound Healing in Pulmonary Fibrosis

Pulmonary fibrosis is hypothesized to develop because epithelial injury and/or cellular stress is/are met by a dysregulated mesenchymal response, leading to deposition of excess collagen and other ECM components into the fibrotic lung (Barkauskas & Noble. Am J Physiol Cell Physiol. 2014 Apr. 16; 306L C987-96).

The wound healing response is dysregulated in pulmonary fibrosis, and disruptions to the highly coordinated wound-repair processes result in pathological scar formation and excessive deposition of ECM components, such as collagen (Chambers. Eur Respir Rev. 2008; 17(109): 130-7). It is thought that in pulmonary fibrosis, aberrant activation of alveolar epithelial cells provokes the migration, proliferation, and activation of mesenchymal cells with the formation of fibroblastic/myofibroblastic foci, leading to the exaggerated accumulation of extracellular matrix with the irreversible destruction of lung tissue (Harari & Caminati. Allergy. 2010 May; 65(5):537-53).

Following injury or "wear and tear" to the alveolar epithelium in otherwise normal lungs, dead or damaged alveolar epithelial cells are replaced by descendants of AEC2s that self-renew and differentiate to AEC1s. It is hypothesized that Scgb1a1+ club secretory cells and/or basal cells serve as a source of AEC2s following injury. These repair processes effectively cover denuded basal lamina, and in the normal healing process, fibrosis does not occur (Barkauskas & Noble. Am J Physiol Cell Physiol. 2014 Jun. 1; 306(11): C987-96). However, in pulmonary fibrosis, abnormal AEC2s are observed, usually overlying fibroblast foci (Rock et al. Proc Natl Acad Sci USA. 2011 Dec. 27; 108(52): E1475-83). The abnormal, hyperplastic morphology of the AEC2s in IPF is thought to relate to cellular stress and the failure to regenerate AEC1s lost by injury or wear and tear. The inability of defective AEC2s to cover the basement membrane denuded by the loss of AEC1s, results the release of profibrotic signals and may perpetuate the development of fibroblast foci (Id.).

In addition to activating the coagulation cascade, platelets and damaged epithelial and endothelial cells release a variety of chemotactic factors that recruit inflammatory monocytes and neutrophils to the site of tissue damage (Wynn & Ramalingam. Nat Med. 2012 Jul. 6; 18(7): 1028-40).

Various growth factors and cytokines secreted by innate inflammatory cells (including macrophages, neutrophils, mast cells and eosinophils) have emerged as potential targets for antifibrotic therapy (Id.). Tumor necrosis factor-α (TNF-α) and interleukin-1β (IL-1β), in particular, have been identified as important targets in a variety of fibrotic diseases (Zhang et al. J Immunol. 1993 May 1; 150(9): 4188-96). Mice that overexpress TNF-α or IL-1β in the lung develop highly progressive pulmonary fibrosis (Miyazaki et al. J Clin Invest. 1995 July; 96(1): 250-9; Kolb et al. J Clin Invest. 2001 June; 107(12): 1529-36). Studies have also shown an essential role for TNF-α in the development of silica- and bleomycin-induced pulmonary fibrosis in mice (Piguet et al. Nature. 1990 Mar. 15; 344(6263): 245-7; Piguet et al. J Exp Med. 1989 Sep. 1; 170(3): 655-63). In support of these experimental findings, patients with idiopathic or systemic sclerosis—associated pulmonary fibrosis have high levels of TNF-α (Piguet et al. Am J Pathol. 1993 September; 143(3): 651-5). Other studies have documented profibrotic activity for IL-1β and NALP3/ASC inflammasome signaling in macrophages (Gasse et al. J Clin Invest. 2007 December; 117(12): 3786-99). Pulmonary fibrosis induced by bleomycin and silica is reduced in IL-1β-deficient mice (Bujak et al. Arch Immunol Ther Exp (Warsz). 2009 May-June; 57(3): 165-76; Jones et al. Nephrol Dial Transplant. 2009; 24: 3024-32; Kamari et al. J Hepatol. 2011 November; 55(5): 1086-94). Like TNF-α, IL-1β is a potent proinflammatory mediator that exacerbates parenchymal-cell injury. It also induces EMT and myofibroblast activation through a TGF-β1-mediated mechanism (Fan et al. Am J Kidney Dis. 2001 April; 37(4): 820-31), confirming that it functions as a potent upstream driver of fibrosis. IL-1β and TNF-α also increase expression of IL-6, which shows autocrine growth-factor activity in fibroblasts. Studies suggest that the cellular source of TGF-β1 dictates its activity, with TGF-β1 derived from macrophages generally showing wound-healing and profibrotic activity and TGF-β1 secreted from CD4+T regulatory cells ($T_{reg}$ cells) functioning as an anti-inflammatory and antifibrotic mediator (Kitani et al. J Exp Med. 2003 Oct. 20; 198(8): 1179-88). Mice deficient in TGF-β1 develop numerous autoimmune disorders and are more susceptible to cancer (Id.).

The CD4+$T_H$17 cell subset that expresses the proinflammatory cytokine IL-17A is emerging as a driver of fibrosis. IL-17A expression has been implicated in the pathogenesis of pulmonary fibrosis (Wilson et al. J Exp Med. 2010 Mar. 15; 207(3): 535-52). In many cases, IL-17A expression is associated with persistent neutrophilia (Laan et al. J Immunol. 1999 Feb. 15; 162(4): 2347-52), and it has been suggested that exaggerated neutrophil recruitment contributes to the development of tissue damage and fibrosis by inducing apoptosis in vascular endothelial cells (Zhu et al. Clin Immunol. 2011 November; 141(2): 152-60). Neutrophil recruitment is also an important predictor of early mortality in IPF patients (Kinder et al. Chest. 2008 January; 133(1): 226-32). Mechanistic studies investigating the IL-17 pathway of fibrosis in mice have identified the proinflammatory cytokines IL-1β and IL-23 as important upstream initiators of profibrotic $T_H$17 responses (Wilson et al. J Exp Med. 2010 Mar. 15; 207(3): 535-52; Gasse et al. PLoS One. 2011; 6(8): e23185). A link between IL-17A and TGF-β1 has also been identified (Wilson et al. J Exp Med. 2010 Mar. 15; 207(3): 535-52). In addition to its role in promoting neutrophilic inflammation, IL-17A has been shown to directly induce expression of matrix metalloproteinase-1 in primary human cardiac fibroblasts (Cortez et al. Am J Physiol Heart Circ Physiol. 2007 December; 293(6): H3356-65), suggesting that IL-17A promotes fibrosis by both exacerbating the upstream inflammatory response and regulating the downstream activation of fibroblasts (Wynn & Ramalingam. Nat Med. 2012 Jul. 6; 18(7): 1028-40).

IL-13 has emerged as a dominant mediator of fibrotic tissue remodeling in several experimental and natural models of fibrosis (Chiaramonte et al. J Clin Invest. 1999 September; 104(6): 777-85). IL-13 production has been implicated in the development of IPF (Murray et al. Int J Biochem Cell Biol. 2008; 40(10): 2174-82). Mechanistically, IL-13 has been hypothesized to induce fibrosis by stimulating the production and activation of TGF-β (Lee et al. J Exp Med. 2001 Sep. 17; 194(6): 809-21). Other studies have suggested that IL-13 can promote fibrosis independently of TGF-β (Liu et al. J Immunol. 2011 Sep. 1; 187(5): 2814-23; Kaviratne et al. J Immunol. 2004 Sep. 15; 173(6): 4020-9) by directly activating the synthetic and proliferative properties of fibroblasts, epithelial cells and smooth-muscle cells (Kuperman et al. Nat Med. 2002 August; 8(8): 885-9; Lee et al. Am J Respir Cell Mol Biol. 2001 October; 25(4): 474-85). Unlike IL-17A—which seems to promote fibrosis indirectly by inducing tissue damage and inflammation—IL-13 and TGF-β show direct fibrotic activity. $T_H$2 cells that produce IL-13 and $T_{reg}$ cells that express TGF-β are also known to inhibit $T_H$17 responses (Wilson et al. Gastroenterology. 2011 January; 140(1): 254-64), suggesting dual roles for IL-13 and TGF-β in the wound-healing response, as both cytokines suppress inflammation while promoting fibrosis. The profibrotic activity of IL-13 is controlled by the abundance of the IL-13Rα1 signaling receptor and IL-13Rα2 decoy receptor expressed on target cells such as myofibroblasts (Ramalingam et al. Nat Immunol. 2008 January; 9(1): 25-33; Chiaramonte et al. J Exp Med. 2003 Mar. 17; 197(6): 687-701). When decoy receptor expression is low or absent, IL-13-dependent fibrosis is exacerbated (Mentink-Kane et al. Gastroenterology. 2011 December; 141(6): 2200-9). However, mice deficient in IL-13Rα2 are more resistant to IL-1β- and IL-17-driven inflammation, probably because of the enhanced IL-13 activity (Wilson et al. Gastroenterology. 2011 January; 140(1): 254-64), suggesting that IL-13Rα2 functions as a key regulator of both $T_H$17-mediated inflammation and $T_H$2-driven fibrosis (Mentink-Kane & Wynn. Immunol Rev. 2004 December; 202: 191-202).

Mechanistically, IFN-γ is believed to inhibit fibrosis, at least in part, by antagonizing the profibrotic activity of TGF-β1. IFN-γ inhibits the TGF-β-induced phosphorylation of the signal transducer Smad3 and subsequent activation of TGF-β-responsive genes (Ulloa et al. Nature 1999 Feb. 25; 397(6721): 710-3). IFN-γ also acts through a pathway dependent on Janus-associated kinase (Jak1) and the transcription factor Stat1 and induces expression of Smad7, which can prevent the interaction of Smad3 with the TGF-β receptor, thus further attenuating TGF-β-induced signaling. IFN-γ also directly inhibits fibroblast proliferation, TGF-β1-induced expression of the genes encoding procollagen I and procollagen III, and collagen synthesis in activated myofibroblasts. IFN-γ also prevents the $T_H$2 cytokine-induced differentiation of CD14+ peripheral blood monocytes into fibroblast-like cells called fibrocytes, which are believed to participate in the development of fibrosis in many organ systems Shao et al. J Leukoc Biol. 2008 June; 83(6): 1323-33). By virtue of its ability to stimulate IFN-γ production in $T_H$1 and natural killer cells, IL-12 has shown similar antifibrotic activity in vivo in mice (Wynn et al. Nature. 1995 Aug. 17; 376(6541): 594-6; Keane et al. Am J Physiol Lung Cell Mol Physiol. 2001 July; 281(1): L92-7). Despite an abundance of in vitro and in vivo evidence supporting an antifibrotic role for $T_H$1-type immunity, clinical studies investigating the therapeutic potential of IFN-γ in the treatment of IPF, systemic sclerosis and other fibrotic disorders have so far been mostly unsuccessful (King et al. Lancet. 2009 Jul. 18; 374(9685): 222-8).

Circulating myeloid cells respond to a gradient of CCL2 and are recruited to damaged tissues, where they differentiate into macrophages that phagocytose the fibrin clot and cellular debris.

Macrophages, which appear early in the wound-healing response and are major producers of TGF-β, one of the drivers of fibrosis (Wynn & Ramalingam. Nat Med. 2012 Jul. 6; 18(7): 1028-40), have also been implicated in the pathogenesis of fibrosis (Wynn & Ramalingam. Nat Med. 2012 Jul. 6; 18(7): 1028-40). Recent literature indicates that various factors should be taken in account in evaluating macrophage activity (Martinez & Gordon. F1000Prime Rep. 2014; 6: 13). Martinez & Gordon have hypothesized that macrophages do not form stable subsets but respond to a combination of factors present in tissues, and that various pathways interact to form complex, even mixed, macrophage phenotypes (Id.).

Although it is widely recognized that monocytes, macrophages and neutrophils have important roles in the progression and resolution of fibrosis (Wynn & Barron. Semin Liver Dis. 2010 August; 30(3): 245-57), other myeloid-lineage cells (such as mast cells, eosinophils and basophils) have also been implicated in the pathogenesis of fibrosis in multiple organ systems (Wynn & Ramalingam. Nat Med. 2012 Jul. 6; 18(7): 1028-40). Mechanistic studies in rats have suggested that mast cells promote fibrosis by recruiting inflammatory leukocytes and by producing profibrotic mediators (Levick et al. Hypertension. 2009 June; 53(6): 1041-7). Eosinophils seem to function in a similar fashion and are considered to be important sources of TGF-β1 and IL-13 (Reiman et al. Infect Immun. 2006 March; 74(3): 1471-9; Minshall et al. Am J Respir Cell Mol boil. 1997 September; 17(3): 326-33). Eosinophils have been most commonly associated with the development of pulmonary fibrosis (Humbles et al. Science. 2004 Sep. 17; 305(5691): 1776-9. Bronchoalveolar-lavage eosinophilia has also been identified as a predictive biomarker of progressive lung disease in IPF and pulmonary fibrosis associated with collagen vascular disorder (Peterson et al. Chest. 1987 July; 92(1): 51-6). Although basophils have a less clear role in the development of fibrosis than the other myeloid-cell populations, they have been implicated in the pathogenesis of myelofibrosis and are frequently found in greater numbers in patients with interstitial lung disease (Gilbert. Prog Clin Biol Res. 1984; 154: 3-17).

ECM fragments, including hyaluronan, have also been shown to be important drivers of fibrosis by stimulating chemokine and proinflammatory cytokine production by inflammatory monocytes and macrophages (Li et al. J Exp Med. 2011 Jul. 4; 208(7): 1459-71).

While in normal wound healing, myofibroblasts are lost via apoptosis when the tissue integrity has been sufficiently restored to be mechanically coherent (Darby et al. Lab Invest. 1990 July; 63(1): 21-9); Desmouliere et al. Am J Pathol. 1995 January; 146(1): 56-66), in the wound healing response in pulmonary fibrosis, myofibroblasts remain, failing to undergo apoptosis, and in turn lead to ongoing pathology of accumulation of collagen and other ECM components, and scarring (Darby et al. Clin Cosmet Investig Dermatol. 2014; 7: 301-11). In other words, in pulmonary fibrosis, there is a defect in the granulation and proliferation and remodeling phases; if the remodeling phase of the granulation tissue fails to happen (neither apoptosis of the cells present in the granulation tissue, myofibroblasts, and vascular cells, nor the reorganization of the ECM), myofibroblasts may persist, leading to pathological situations characterized by pulmonary fibrosis (Id.).

Fibroblastic Cells and Myofibroblast Differentiation in Fibrotic Conditions

Fibroblasts and myofibroblasts from IPF patients have been shown to have distinct properties, including the ability to invade the ECM. A hallmark and defining pathological feature of IPF is the formation of fibroblastic foci, which are the accumulation of myofibroblasts in the interstitium of the lung juxtaposed to the alveolar epithelium with destruction of the adjoining alveolar basement membrane (Selman & Pardo. Respir Res. 2002; 3: 3). The destruction of alveolar basement membrane was also observed in experimental lung fibrosis (Fukuda et al. Am J Pathol. 1985 March; 118(3): 452-75; Vaccaro et al. Am Rev Respir Dis. 1985 October; 132(4): 905-12). In view of the many characteristics that encompass features of fibrosis, such as the elaboration of ECM and expression/activation of TGFβ1 (Zhang et al. Am J Pathol. 1994 July; 145(1): 114-25); Zhang et al. J Immunol. 1994 Nov. 15; 153(10): 4733-41), the persistence of the myofibroblast is thought to be of significance in the propagation of fibrosis in pulmonary fibrosis. Early studies of the origin of the myofibroblast in lung injury and fibrosis suggest several possibilities based on observations of its cytoskeletal phenotype, tissue localization, and in vitro studies. Based on evidence that myofibroblasts arise de novo and on the kinetics of the induction of α-SMA expression, perivascular and peribronchiolar adventitial fibroblasts, i.e., the local fibroblasts have been suggested as precursors (Zhang et al. Am J Pathol. 1994 July; 145(1): 114-25), but it has also been reported that circulating fibrocytes (expressing CD45, CD34, collagen I, and CXCR4) can migrate to sites of tissue injury and differentiate into myofibroblasts (Abe et al. J Immunol. 2001 Jun. 15; 166(12): 7556-62; Phillips et al. J Clin Invest. 2004 August; 114(3): 438-46). It has been suggested that such newly appearing myofibroblasts, characterized by α-SMA and/or desmin, expression, may be responsible for the increased lung collagen gene expression in pulmonary fibrosis (Zhang et al. Am J Pathol. 1994 July; 145(1): 114-25).

The mechanism underlying the source of myofibroblasts in pulmonary fibrosis is complex; it has been determined that the presence of Smad3, an intracellular signal transducer for TGF-β1, may have an essential role in myofibroblast differentiation (Ramirez et al. Am J Transplant. 2006 September; 6(9): 2080-8; Hu et al. Am J Respir Cell Mol boil. 2007 January; 36(1): 78-84). However, regulation of the α-SMA gene is quite complex (Giannone & Sheetz. Trends Cell Biol. 2006 April; 16(4): 213-23; Ramirez et al. Am J Transplant. 2006 September; 6(9): 2080-8; Hu et al. Am J Respir Cell Mol boil. 2007 January; 36(1): 78-84). Additional transcription factors, including C/EBPβ (CCAAT/enhancer-binding protein β), GKLF (gut-enriched Krüppel-like factor), Sp1/Sp3, c-myb, and the downstream effector component of Notch signaling, have been implicated to regulate this gene in a complex and interactive manner, and in addition to inducers, suppressors such as the liver-enriched inhibitory protein isoform of C/EBPβ may serve to keep the precursor fibroblast in an undifferentiated state under normal homeostasis (Hinz et al. Am J Pathol. 2007 June; 170(6): 1807-16). Epigenetic modifications in fibroblasts also contribute to the pathogenesis of fibrosis by stably altering the activation status of myofibroblasts (Wynn & Ramalingam. Nat Med. 2012 Jul. 6; 18(7): 1028-40).

In pulmonary fibrosis, myofibroblasts are found in abundance in areas of high ECM expression and represent the predominant source of heightened ECM and cytokine gene expression (Zhang et al. Am J Pathol. 1994 July; 145(1): 114-25). The myofibroblast is a factor in alveolar epithelial apoptosis, denudation, and retardation of epithelial regeneration (Waghray et al. FASEB J. 2005 May; 19(7): 854-6). Thus, in addition to its potential contribution to reduction in lung tissue compliance, the myofibroblast is likely to play significant roles in promoting ECM deposition, release of inflammatory mediators, and epithelial injury, all of which are considered to be key factors in perpetuating the cycle of injury and fibrosis. As noted above, in pulmonary fibrosis, myofibroblasts fail to undergo apoptosis, as in the normal wound healing response, which leads to ongoing pathology of accumulation of collagen and other ECM components, and scarring (Darby et al. Clin Cosmet Investig Dermatol. 2014; 7: 301-11).

TGFβ1 can induce p38 mitogen-activated protein kinase pathway activation with subsequent activation of the pro-survival phosphatidylinositol 3-kinase-AKT pathway (Horowitz et al. J Biol Chem. 2004 Jan. 9; 279(2): 1359-67). Deficiency in PTEN, a phosphatidylinositol 3-kinase-AKT pathway inhibitor, is associated with increased myofibroblast differentiation (White et al. Am J Respir Crit Care Med. 2006 Jan. 1; 173(1): 112-21). Thus, in addition to promoting myofibroblast differentiation, combinatorial activation of the adhesion-dependent focal adhesion kinase pathway and the soluble growth factor-mediated AKT pathway confers apoptosis/anoikis (programmed cell death induced by anchorage-dependent cells detaching from surrounding ECM) resistance to TGFβ1-differentiated myofibroblasts (Horowitz et al. Cell Signal. 2007 April; 19(4): 761-71).

IPF Fibroblasts Possess a Malignant Phenotype with an Increased Capacity for Invasion It has been proposed that fibroblasts in the IPF lung acquire a phenotype that is reminiscent of malignant cells (Barkauskas & Noble. Am J Physiol Cell Physiol. 2014 Jun. 1; 306(11): C987-96). Fibroblasts from the IPF lung display enhanced migratory capacity when assessed in a chemotaxis chamber with platelet-derived growth factor (PDGF) as the chemoattractant. Fibroblasts from tissues with more dense fibrosis displayed capacity for migration compared with fibroblasts isolated from earlier stage disease (Suganuma et al. Thorax. 1995 September; 50(9): 984-9). IPF fibroblasts, compared with fibroblasts from normal human lung, display slower growth rates, higher rates of apoptosis, and a profibrotic secretory phenotype (Ramos et al. Am J Respir Cell Mol Biol. 2001 May; 24(5): 591-8). In addition, fibrotic lung fibroblasts, unlike normal fibroblasts and more consistent with cancer-derived cells, are able to survive in the absence of attachment and interaction with extracellular matrix and neighboring cells, displaying anchorage-independent growth in soft agar (Torry et al. J Clin Invest. 1994 April; 93(4): 1525-32).

IPF Fibroblasts Demonstrate Impaired Mechanosensitive Signaling

It has long been viewed that myofibroblasts, with their contractile properties, are key effector cells in wound healing (Barkauskas & Noble. Am J Physiol Cell Physiol. 2014 Jun. 1; 306(11): C987-96). After facilitating wound closure, these cells typically disappear from granulation tissue, presumably via a de-differentiation mechanism (Kisseleva et al. Proc Natl Acad Sci USA. 2012 Jun. 12; 109(24): 9448-53), a clearance mechanism (Friedman. Proc Natl Acad Sci USA. 2012 Jun. 12; 109(24): 9230-1; Krizhanovsky et al. Cell. 2008 Aug. 22; 134(4): 657-67), or a combination of both. In IPF, myofibroblasts are believed to persist inappropriately, leading to progressive fibrosis. It has been shown that mechanical stimuli (e.g., stiff extracellular matrix with myofibroblasts generating high contractile forces) can be converted to fibrogenic signals (e.g., liberation of TGF-β1), which, in turn, maintains the myofibroblastic phenotype (Wipff et al. J Cell Biol. 2007 Dec. 17; 179(6): 1311-23). An intrinsic mechanotransduction mechanism that promotes myofibroblast differentiation regulated by nuclear translocation of MKL1 (myocardin-related transcription factor-A, a mechanosensitive transcription factor that is involved in activating the fibrotic gene program) that results in stiff matrix-promoting aSMA gene expression by normal lung fibroblasts (Huang et al. Am J Respir Cell Mol Biol. 2012 September; 47(3): 340-8) has been described. These experiments were done by comparing (myo)fibroblast behavior on polyacrylamide hydrogels of differing stiffness. This intrinsic mechanotransduction is mediated by the Rho kinase (ROCK) pathway, which regulates myofibroblast contractility, differentiation, and survival experiments (Zhou et al. J Clin Invest. 2013 March; 123(3): 1096-108). These experiments also demonstrated that preexisting myofibroblasts can be shuttled to an apoptotic fate if their contractile properties are disrupted (Barkauskas & Noble. Am J Physiol Cell Physiol. 2014 Jun. 1; 306(11): C987-96).

Mechanisms and Pathways of Fibrosis

Because ECM-secreting myofibroblasts are central to the pathogenesis of fibrotic diseases, fibrosis research has focused on elucidating the molecular and immunological mechanisms that initiate, maintain and terminate the differentiation of quiescent fibroblasts into actively proliferating, ECM-producing myofibroblasts (Wynn & Ramalingam. Nat Med. 2012 Jul. 6; 18(7): 1028-40). The mechanisms that control progressive fibrosis, however, are largely unknown (Li et al. J Exp Med. 2011 Jul. 4; 208(7): 1459-71).

Origin of Profibrotic Fibroblasts

The origin of fibrotic fibroblasts has been of great interest in understanding the pathogenesis of tissue fibrosis (Dulauroy et al. Nat Med. 2012 August; 18(8): 1262-70; Hung et al. Am J Respir Crit Care Med. 2013 Oct. 1; 188(7): 820-30; LeBleu et al. Nat Med. 2013 February; 19(2): 227-31; Rock et al. Proc Natl Acad Sci USA. 2011 Dec. 27; 108(52): E1475-83). Fibrotic fibroblasts in IPF are extremely heterogeneous (Jordana et al. Am Rev Respir Dis. 1988 March; 137(3): 579-84), suggesting they may be raised from different cell types, or represent different stages of activation, or are influenced by their milieu (Zeisberg and Kalluri. Am J Physiol Cell Physiol. 2013 Feb. 1; 304(3): C216-25.). The heterogeneous nature of fibroblasts has also been demonstrated in mouse models (Rock et al. Proc Natl Acad Sci USA. 2011 Dec. 27; 108(52): E1475-83). A common, long-sought-after, marker for fibroblasts has not been identified because of this heterogeneity (Zeisberg and Kalluri. Am J Physiol Cell Physiol. 2013 Feb. 1; 304(3): C216-25), and the major source of profibrotic fibroblasts has not yet been discovered.

Markers such as a smooth muscle actin (α SMA, encoded by ACTA2 gene, the actin isoform that predominates within smooth-muscle cells and plays an important role in fibrogenesis (Cherng et al. J Am Sci. 2008: 4(4): 7-9)), FSP1/S100A4 (fibroblast-specific protein 1/S100A4-positive protein, a marker of fibroblasts in different organs undergoing tissue remodeling (Osterreicher et al. Proc Natl Acad Sci USA. 2010 Nov. 23; 108(1): 308-13)), Vimentin (a major constituent of the intermediate filament (IF) family of proteins, known to maintain cellular integrity and provide resistant against stress (Satelli & Li. Cell Mol Life Sci. 2011 September; 68(18): 3033-46)), Desmin, and PDGFRB (platelet-derived growth factor receptor, beta polypeptide, a tyrosine kinase receptor for members of the PDGF family) are either not exclusively expressed by fibroblasts or specific to all fibroblasts (Krenning et al. J Cell Physiol. 2010

November; 225(3): 631-7; Rock et al., Proc Natl Acad Sci USA. 2011 Dec. 27; 108(52): E1475-83).

It has been suggested that several cellular sources contribute to fibrotic fibroblasts. For example, it has been suggested that circulating fibrocytes or other bone marrow-derived progenitor cells of extrapulmonary origin might be able to migrate to active fibrotic lesions and become fibrotic cells (Andersson-Sjoland et al. Int J Biochem Cell Biol. 2008; 40(10) 2129-40; Hashimoto et al. J Clin Invest. 2004 January; 113(2): 243-52; Phillips et al. J Clin Invest. 2004 August; 114(3): 438-46). Experimental fibrosis models have led to the proposal that epithelial cells (Degryse et al. Am J Physiol Lung Cell Mol Physiol. 2010 October; 299(4): L442-52; Kim et al. Proc Natl Acad Sci USA. 2006 Aug. 29; 103(35): 13180-5; Tanjore et al. Am J Respir Crit Care Med. 2009 Oct. 1; 180(7): 657-65) or endothelial cells (Hashimoto et al. Am J Respir Cell Mol Biol. 2010 August; 43(2): 161-72; LeBleu et al. Nat Med. 2013 August; 19(8): 1047-53; Li and Jimenez. Arthritis Rheum. 2011 August; 63(8): 2473-83) may be able to transform to stromal cells in experimental fibrosis models. However, a genetic tracing approach showed that lung epithelial cells such as Sftpc-lineage AEC2s, as well as Scgb1a1-lineage club cells, do not give rise to fibroblasts (Rock et al. Proc Natl Acad Sci USA. 2011 Dec. 27; 108(52): E1475-83). Genetic fate-mapping methods have confirmed that pericytes proliferate during fibrogenesis, where the pericytes were trace-labeled with either NG2, FoxJ1 or Foxd1 (Hung et al. Am J Respir Crit Care Med. 2013 Oct. 1; 188(7): 820-30 Rock et al. Proc Natl Acad Sci USA. 2011 Dec. 27; 108(52): E1475-83). However, neither these cells nor their progeny express high levels of the myofibroblast marker αSMA; expression of αSMA marks myofibroblasts and smooth muscle cells. Some perivascular Gli1+ cells with distinct characteristics of mesenchymal stem cells (MSCs) can differentiate into myofibroblasts in tissue fibrosis (Kramann et al. Cell Stem Cell. 2015 Jan. 8; 16(1): 51-66).

A mesenchymal transcription factor, T-box protein 4 (Tbx4), which is expressed early during embryonic development and controls limb identity (Takeuchi et al. Nature. 1999 Apr. 29; 398(6730): 810-4)) and airway branching (Arora et al. PLos Genet. 2012; 8(8): e1002866) has been identified as a possible source of fibrotic fibroblasts. Tbx4, a member of the T-box family of transcription factors, is involved in multiple biological processes, including angiogenesis, morphogenesis of an epithelium, DNA-templated transcription and regulation of transcription, multicellular organismal development, lung development, limb morphogenesis, and skeletal system morphogenesis; Tbx4 has been found to interact with over 150 different proteins (Papaioannou. Development. 2014 October; 141(20): 3819-33; http://www.genecards.org/cgi-bin/carddisp.pl?gene=TBX4).

Experiments involving the ablation of TBx4+ cells or the disruption of Tbx4 signaling attenuated bleomycin-induced lung fibrosis in in vivo mouse studies. The inventors have shown, by in vivo different mesenchymal marker tracking, multicolor clonal cell labeling, specific cell ablation, and gene deletion in a cell type specific fashion, that Tbx4 lineage cells give rise to fibroblasts, smooth muscle cells, pericytes and endothelial cells in the lung. Tbx4+ cells expanded, proliferated, and formed clonal-like patches within fibrotic foci, and are the major source of αSMA+ fibrotic fibroblasts. Specific deletion of Tbx4+ cells or Tbx4 gene in either collagen- or α-SMA-expressing fibrotic fibroblasts significantly attenuated lung fibrosis, revealing the involvement of Tbx4 in the TGF-β pathway with regards to fibroblast activation and differentiation during tissue fibrosis.

C. Intrinsic, Autocrine and Epigenetic Mechanisms Regulate Fibrosis

Hyaluronan (HA) is a nonsulfated glycosaminoglycan produced by mesenchymal cells and a variety of tumor cells and has been suggested to contribute to tumor metastasis through interactions with its cognate cell surface receptor CD44 (Arch et al. Science. 1992 Jul. 31; 257(5070): 682-5; Toole, Nat Rev Cancer. 2004 July; 4(7): 528-39). HA is nearly ubiquitous in its distribution, being present in the interstitial spaces of most animal tissues. Accumulation of HA has been shown to be a characteristic of disorders that are associated with progressive tissue fibrosis (Bjermer et al. Thorax. 1989 February; 44(2): 126-31). HA has also been shown to accumulate in the lungs of rats after bleomycin-induced injury, and has a role in regulating the inflammatory response (Jiang et al. Nat Med. 2005 November; 11(11): 1173-9; Noble et al. Physiol Rev. 2011 January; 91(1): 221-64). Three HA synthase genes (HAS1-3) have been identified. Targeted deletion of HAS2 generates an embryonic lethal phenotype caused by impaired cardiac development (Camenisch et al. J Clin Invest. 2000 August; 106(3): 349-60).

CD44 is a ubiquitous cell-surface glycoprotein involved in myriad processes, comprising over 25 signaling super pathways (www.genecards.org/cgi-bin/carddisp.pl?gene-CD44). FIG. 3 illustrates pathways in which CD44 is involved. CD44 is a major cell surface receptor for HA and plays an important role in inflammatory cell recruitment (Mikecz et al. Nat Med. 1995 June; 1(6): 558-63; Siegelman et al. J Leukoc Biol. 1999 August; 66(2): 315-21) and activation (Nobel et al. J Clin Invest. 1993 June; 91(6): 2368-77; DeGrendele et al. Science. 1997 Oct. 24; 278 (5338): 672-5), as well as tumor growth and metastasis (Lesley et al. Adv Immunol. 1993; 54: 271-335). CD44 is necessary for hematopoietic cells to clear HA from sites of inflammation (Teder et al. Science. 2002 Apr. 5; 296(5565: 155-8), and is critical for the recruitment of fibroblasts to injury sites (Acharya et al., J Cell Sci. 2008 May 1; 121(Pt 9): 1393-402.).

The inexorable course of progressive fibrosis in IPF has led to the theory that fibroblasts may take on properties similar to metastatic cancer cells that overexpress HA. Consistent with this concept is a recent study showing that IPF fibroblasts have abnormalities in translational control (Larsson et al. PLoS One. 2008 Sep. 16; 3(9): e3220) that can be found in cancer cells. One of the seminal properties of metastatic cancer cells is the ability to invade basement membrane. It has been suggested that fibrotic fibroblasts and myofibroblasts drive fibrogenesis by invasion and destruction of basement membrane and that HA-CD44 interactions may regulate this process.

Mechanical modifications to the ECM and cell-intrinsic changes in fibroblasts and epithelial cells have been shown to contribute to the progression of fibrosis by maintaining the activation of the following fibrogenic pathways (Wynn & Ramalingam. Nat Med. 2012 Jul. 6; 18(7): 1028-40).

1. The Wnt-β-Catenin Signaling Pathway

The Wnt-β-catenin signaling pathway is constitutively activated in AEC2s in mouse models of pulmonary fibrosis and in patients diagnosed with IPF and chronic obstructive pulmonary disease (Baarsma et al. PLoS One. 2011; 6(9): e25450). The Wnt-β-catenin signaling pathway is illustrated in FIG. 4. This ubiquitous pathway is involved in organ development, tissue homeostasis, cell growth, renewal, and regeneration, and is intimately involved in tumorigenesis (Valenta et al. EMBO J. 2012 Jun. 13; 31(12): 2714-36). Wnt-1 is involved in over 30 signaling super pathways, and β-catenin is involved in nearly 100 signaling super pathways (www.genecards.org/cgi-bin/carddisp.pl?gene=WNT1; www.genecards.org/cgi-bin/carddisp.pl?gene=CTNNB1)

Mechanistically, Wnt-1—inducible signaling protein 1 (WISP-1) has been shown in mice to increase the proliferation of AEC2s, and promote EMT in the lung (Wynn & Ramalingam. Nat Med. 2012 Jul. 6; 18(7): 1028-40). WISP-1 also increases the synthesis of ECM components in mouse and human lung fibroblasts (Jiang et al. J Hepatol. 2006 September; 45(3): 401-9). Blocking studies demonstrated that bleomycin-induced pulmonary fibrosis is highly dependent on the Wnt-1 pathway (Konigshoff et al. J Clin Invest. 2009 April; 119(4): 772-87).

As tissues become more fibrotic, the increased tissue stiffness and decreased elasticity result in mechanical stress, which has been shown to exacerbate tissue injury and perpetuate the activation of local fibroblasts expressing α-smooth muscle actin (α-SMA) (Hinz et al. Mol Biol Cell. 2001 September; 12(9): 2730-41). Two in vitro studies in mouse and porcine cells have suggested that mechanical stress contributes to aberrant wound healing and fibrosis by inducing EMT in AEC2s via a mechanism driven by TGF-β1, Wnt-β-catenin and hyaluronan (Heise et al. J Biol Chem. 2011 May 20; 286(20): 17435-44; Chen et al. Arterioscler Thromb Vasc Biol. 2011 March; 31(3): 590-7). Fibroblasts that are activated as a result of increased tissue or substrate stiffness also seem to maintain their activated phenotype when returned to healthy 'soft' tissues (Balestrini et al. Integr Biol (Camb). 2012 April; 4(4): 410-21), suggesting that mechanical sensing by fibroblasts can permanently alter their behavior in favor of a fibrotic phenotype. It has been suggested that the differentiation of fibroblasts into ECM-producing myofibroblasts is controlled by the combined actions of IL-1β, TGF-β1 and mechanical tension (Hinz. Curr Rheumatol Rep. 2009 April; 11(2): 120-6). Increased compression, shear forces and hydrostatic pressures associated with portal hypertension and vascular remodeling can also perpetuate myofibroblast activation (Wynn & Ramalingam. Nat Med. 2012 Jul. 6; 18(7): 1028-40).

Biomarkers in IPF

Researchers have made efforts to identify diagnostic and predictive biomarkers to improve the drug development in IPF, especially in view of the devastating effects and lethality of IPF and its unknown origin (Zhang & Kaminski. Curr Opin Pulm Med. 2012 September; 18(5): 441-6).

A. Diagnostic Biomarkers

In the context of peripheral blood markers, multiple molecules have been shown to distinguish patients with IPF from controls. These include KL-6 (a high molecular weight glycoprotein used as a serum marker for interstitial lung diseases (Yokoyama et al. Respirology. 2006 March; 11(2): 164-8), surfactant proteins SP-A and SP-D (collagenous glycoproteins investigated at biomarkers for IPF (Greene et al. Eur Respir J. 2002 March; 19(3): 439-46)), matrix metalloproteases MMP-1 and MMP-7 (interstitial collagenases investigated as biomarkers for IPF (Rosas et al. PLoS Med. 2008 Apr. 29; 5(4): e93), SPP1 (glycoprotein observed to be upregulated in human IPF (Pardo et al. PLoS Med. 2005 September; 2(9): e251)) and YKL-40 (a mammalian chitinase-like protein observed to be upregulated in IPF (Furuhashi et al. Respir Med. 2010 August; 104(8): 1204-10). However, the diagnostic utility of any of these molecules is in doubt as the majority of the studies usually only compared IPF to control individuals, and when smoking controls or other interstitial lung diseases ("ILDs") were analyzed, they often had increased levels of the markers (Zhang & Kaminski. Curr Opin Pulm Med. 2012 September; 18(5): 441-6).

B. Disease Susceptibility Biomarkers

Multiple mutations associated with familial and sporadic forms of IPF have been reported including mutations in surfactant (Thomas et al. Am J. Respir Crit Care Med. 2002 May 1; 165(9): 1322-8; Lawson et al. Thorax. 2004 November; 59(11): 977-80; Wang et al. Am J Hum Genet. 2009 January; 84(1): 52-9) and telomerase proteins (Armanios et al. N Engl J Med. 2007 Mar. 29; 356(13): 1317-26; Tsakiri et al. Proc Natl Acad Sci USA. 2007 May 1; 104(18): 7552-7). Polymorphisms within TERT (telomerase reverse transcriptase) have also been identified [single nucleotide polymorphism (SNP) in intron 2 of the TERT gene—rs2736100] in a genome-wide association (GWA) study including a derivation cohort of 159 sporadic IPF patients and 934 controls as well as a replication cohort of 83 sporadic IPF cases and 535 controls (Mushiroda et al. J Med Genet. 2008 October; 45(10): 654-6). Leukocyte telomere shortening was found in 24% of familial pulmonary fibrosis and 23% of sporadic IPF cases when compared to control individuals (P=2.6×10-8) (Cronkhite et al. Am J Respir Crit Care med. 2008 Oct. 1; 178(7): 729-37) in a study that contained 201 control individuals, 59 probands with familial pulmonary fibrosis and 73 sporadic pulmonary fibrosis cases without TERT or TERC (telomerase RNA component) mutations. Other genetic variants have been described in IPF, including genes encoding ELMOD2 (a GPTase-activating protein (Hodgson et al. Am J Hun Genet. 2006 July; 79(1): 149-54)), IL-1 (cytokine involved in immune and inflammatory responses (Hutyrova et al. Am j Respir Crit Care Med. 2002 Jan. 15; 165(2): 148-51)), CR-1 (complement receptor 1, a transmembrane glycoprotein, (Zorzetto et al. Am J Respir Crit Care Med. 2003 Aug. 1; 168(3): 330-4)), IL12p40 and IFN-γ (IL-12 p40 subunit and IFN-γ (Latsi et al. Respir Res. 2003. 4:6)), NOD2/CARD15 (an intracellular innate immune sensor (Zorzetto et al. Sarcoidosis Vasc Diffuse Lung Dis. 2005 October; 22(3): 180-5)), MMP-1 (matrix metalloproteinase-1 (Checa et al. Hum Genet. 2008 December; 124(5): 465-72), ENA-78 (epithelial neutrophil activating peptide 78), IP-10 (interferon-inducible protein 10), and VEGF (vascular endothelial growth factor), (Liu et al. Zhonghua Yi Xue Za Zhi. 2009 Oct. 20; 89(38): 2690-4), CD16b (Fcγ receptor Mb (Bournazos et al. Lung. 2010 December; 188(6): 475-81)), IL-8 (interleukin 8 (Ahn et al. Respir Res. 2011 Jun. 8; 12:73)) and HER2 (human epidermal growth factor receptor 2 (Martinelli et al. Mol Biol Rep. 2011 October; 38(7): 4613-7)), but the majority have not been replicated. Recently, a SNP in the putative promoter of MUC5B (rs35705950) that was associated with familial interstitial pneumonia (minor allele frequency of 34%, P=1.2×10$^{-15}$) and IPF (minor allele frequency of 38%, P=2.5×10$^{-37}$) has been identified; in controls, the minor allele frequency was 9% (Seibold et al. N Engl J Med. 2011 Apr. 21; 364(16): 1503-12). The odds ratio was 6.2 [95% confidence interval (CI) 3.7-10.4] for familial interstitial pneumonia and 8.3 (95% CI 5.8-11.9) for IPF (Id.). These findings were simultaneously confirmed by other researchers in an independent case-control study that included 341 IPF and 801 control individuals (Zhang et al. N Engl J Med. 2011 Apr. 21; 364(16): 1576-7). The minor-allele frequency was 34.3% in patients with IPF and 11.1% in controls (allelic association, P=7.6×10-40) (Id.).

C. Prognostic Biomarkers

High blood concentrations of KL-6, also known as MUC-1, repeatedly have been shown to be predictive of decreased survival in IPF (Zhang & Kaminski. Curr Opin Pulm Med. 2012 September; 18(5): 441-6). Most studies have been limited by cohort size and lack replication, but are still highly consistent and support the use of KL-6 in disease stratification (Ishikawa et al. Respir Investig. 2012 March; 50(1): 3-13. Other studies have shown that serum CCL18 (chemokine (C—C motif) ligand 18) levels were able to predict outcomes in IPF (higher serum CCL18 concentrations were predictive of decreased total lung capacity, decreased forced vital capacity and increased mortality (Prasse et al. Am J Respir Crit Care Med. 2009 Apr. 15; 179(8): 717-23)), that high serum SP-A concentrations was a predictor of early mortality in IPF (Kinder et al. Chest. 2009 June; 135(6): 1557-63), and that high serum concentrations of YKL-40 distinguished two groups with distinct survival patterns with the hazard ratio for serum YKL-40 (cut-off 79 ng/ml) as 10.9 (95% CI 1.9-63.8, P<0.01) (Korthagen et al. Respir Med. 2011 January; 105(1): 106-13). Researchers using a targeted proteomic approach screened 95 proteins in the plasma of 140 IPF patients (derivation cohort) and validated the results in a replication cohort (101 patients) (Richards et al. Am J Respir Crit Care Med. 2012 Jan. 1; 185(1): 67-76). High plasma concentrations of MMP-7, ICAM-1 and IL-8 were predictive of poor overall survival in both cohorts (Id.). The derivation cohort was used to derive a personal clinical and molecular mortality prediction index (PCMI) using the step AIC approach (Venables & Ripley. Modern applied statistics with S. New York: Springer; 2002). This index [PCMI=114×I(Male)+2×(100%−FVC % predicted)+3×(100%−Dlco % predicted)+111×I(MMP-7≥4.3 ng/ml)] was highly predictive of mortality in the replication cohort with a C-index for early mortality of 84 (Richards et al. Am J Respir Crit Care Med. 2012 Jan. 1; 185(1): 67-76).

Similarly, changes in circulating blood cell populations have been associated with outcome. Recent studies have demonstrated in a cohort of 51 patients that increases in circulating fibrocytes predicted poor prognosis (Moeller et al. Am J Respir Crit Care Med. 2009 Apr. 1; 179(7): 588-94) and other researchers have observed that downregulation of CD28 in circulating CD4 T cells was a marker of poor prognoses in a cohort of 89 IPF patients (Gilani et al. PLoS One. 2010 Jan. 29; 5(1): e8959.

D. Disease Activity Markers

There is no real definition of the disease activity of IPF. It is conceivable that KL-6, SP-A and MMP-7 are markers of alveolar epithelial cell injury and CCL-18 a marker of alveolar macrophage activation; however, at present, markers for some of the processes that happen in IPF such as deposition of excess collagen have not yet been discovered. Mechanistically, the biomarker that may be tied most closely to disease pathogenesis is MMP-7, a pluripotent matrix metalloprotease expressed in alveolar type II cells. MMP-7 is a WNT/β-catenin pathway target molecule (He et al. J Am Soc Nephrol. 2012 February; 23(2): 294-304), suggesting that increases of MMP-7 are reflective of aberrant WNT/β catenin that has been described in IPF (Chilosi et al. Am J Pathol. 2003 May; 162(5): 1495-502; Konigshoff et al. J Clin Invest. 2009 April; 119(4): 772-87). MMP-7 knockout mice are relatively protected from bleomycin-induced fibrosis, suggesting that it is mechanistically involved in the fibrosis pathways (Zuo et al. Proc Natl Acad Sci USA. 2002 Apr. 30; 99(9): 6292-7). However, at present, there is no data to support MMP-7 as a marker of disease activity (Id.).

Acute exacerbations of IPF (AE-IPF) are episodes of decline in respiratory status without an identifiable cause (Collard et al. Am J Respir Crit Care Med. 2007 Oct. 1; 176(7): 636-43), that lead to significant mortality (Song et al. Eur Respir J. February; 37(2): 356-63). Of the previous markers mentioned, KL-6 has been mostly widely studied in this context (Ishikawa et al. Respir Investig. 2012 March; 50(1): 3-13; Collard et al. Am J Physiol Lung Cell Mol Physiol. 2010 July; 299(1): L3-7; Satoh et al. J Intern Med. 2006 November; 260(5): 429-34). It appears that AE-IPF are associated with increases in blood KL-6, although the mechanisms have not yet been elucidated. Comparisons of gene expression in the lungs of patients with AE-IPF lungs to stable IPF (Konishi et al. Am J Respir Crit Care med. 2009 Jul. 15; 180(2): 167-75) has identified 579 differentially expressed genes, and did not find any indication of infectious or inflammatory cause. Researchers have found increases in α-defensins, a group of innate antimicrobial peptides, in the mRNA levels as well as in the plasma protein level of AE-IPF patients, suggesting that they should be evaluated as biomarkers for acute exacerbations (Zasloff. Nature. 2002 Jan. 24; 415(6870): 389-95).

E. Drug Efficacy Biomarkers

There are no drug efficacy biomarkers in IPF (Zhang & Kaminski. Curr Opin Pulm Med. 2012 September; 18(5): 441-6).

Utility and Limitations of Animal Models in the Study of IPF

Bleomycin, a chemotherapeutic agent used in the treatment of certain human cancers, has been the most commonly used agent to induce pulmonary fibrosis in animal models of the disease. Bleomycin can be administered through a variety of routes including intratracheal (most common), intraperitoneal, oropharyngeal aspiration, and via osmotic pump. It induces DNA strand breaks (Lown & Sim. Biochem Biophys Res Commun. 1977 Aug. 22; 77(4): 1150-7) and oxidative injury (Sausville et al. Biochem Biophys Res Commun. 1976 Dec. 6; 73(3): 814-22), thus leading to epithelial injury, inflammation, and ultimately fibrosis (Barkauskas & Noble. Am J Physiol Cell Physiol. 2014 Jun. 1; 306(11): C987-96).

The bleomycin model is well-documented and the best characterized murine model in use today to demonstrate efficacy of a particular drug or protein kinase inhibitor in the post-inflammatory/pre-fibrotic/fibro-preventive stages (Vittal, R. et al., *J Pharmacol Exp Ther.*, 321(1):35-44, 2007; Vittal, R. et al., *Am J Pathol.*, 166(2):367-75, 2005; Hecker L. et al., Nat Med., 15(9):1077-81, 2009).

The antibiotic bleomycin was originally isolated from *Streptomyces verticillatus* (Umezawa, H. et al., *Cancer* 20: 891-895, 1967), and was subsequently found to be effective against squamous cell carcinomas and skin tumors (Umezawa, H., *Fed Proc,* 33: 2296-2302, 1974); however, its usefulness as an anti-neoplastic agent was limited by dose-dependent pulmonary toxicity resulting in fibrosis (Muggia, F. et al., *Cancer Treat Rev,* 10: 221-243, 1983). The delivery of bleomycin via the intratracheal route (generally 1.25-4 U/kg, depending on the source) has the advantage that a single injection of the drug produces lung injury and resultant fibrosis in rodents (Phan, S. et al., *Am Rev Respir Dis* 121: 501-506, 1980; Snider, G. et al., *Am Rev Respir Dis.* 117: 289-297, 1978; Thrall, R. et al., *Am J Pathol,* 95: 117-130, 1979). Intratracheal delivery of the drug to rodents results in direct damage initially to alveolar epithelial cells. This event is followed by the development of neutrophilic and lymphocytic pan-alveolitis within the first week (Janick-Buckner, D. et al., *Toxicol Appl Pharmacol.*, 100(3):465-73, 1989). Subsequently, alveolar inflammatory cells are cleared, fibroblast proliferation is noted, and extracellular matrix is synthesized (Schrier D. et al., *Am Rev Respir Dis.*, 127(1):63-6, 1983). The development of fibrosis in this model can be seen biochemically and histologically by day 14 with maximal responses generally noted around days 21-28 (Izbicki G. et al., *Int J Exp Pathol.*, 83(3):111-9, 2002; Phan, S. et al., *Chest.*, 83(5 Suppl):44S-45S, 1983). Beyond 28 days, however, the response to bleomycin is more variable. Original reports suggest that bleomycin delivered intratracheally may induce fibrosis that progresses or persists for 60-90 days (Thrall R. et al., *Am J Pathol.*, 95(1):117-30, 1979; Goldstein R., et al., *Am Rev Respir Dis.*, 120(1):67-73, 1979; Starcher B. et al., *Am Rev Respir Dis.*, 117(2):299-305, 1978); however, other reports demonstrate a self-limiting response that begins to resolve after this period (Thrall R. et al., *Am J Pathol.*, 95(1):117-30, 1979; Phan, S. et al., *Chest*, 83(5 Suppl): 44S-45S, 1983; Lawson W. et al., *Am J Pathol.* 2005; 167(5):1267-1277). While the resolving nature of this model does not mimic human disease, this aspect of the model offers an opportunity for studying fibrotic resolution at these later time points.

The pathology generated by intratracheal bleomycin is not fully representative of IPF histology. The diagnostic criteria for IPF (usual interstitial pneumonia) are threefold: 1) nonuniform pattern of disease involvement with normal lung interspersed with diseased lung, 2) architectural distortion (honeycomb change and/or scar), and 3) presence of fibroblast foci, presumed to be indicative of current ongoing disease. These structures are covered by hyperplastic AEC2s (Katzenstein et al. Hum Pathol. 2008 September; 39(9): 1275-94). While not a diagnostic criterion, human IPF specimens also typically include areas of alveolar collapse with incorporation of basal lamina (Myers & Katzenstein. Chest. 1988 December; 94(6): 1309-11). While experimental bleomycin fibrosis can recapitulate alveolar collapse and cystic air spaces 14 days after intratracheal instillation (Moore et al. Am J Respir Cell Mol Biol), it is also typically characterized by significant neutrophilic inflammation, and there rarely exist examples of the hyperplastic AEC2s that are pathognomonic for the human disease (Degryse et al. Am J Physiol Lung Cell Mol Physiol. 2010 October; 299(4): L442-52; Moore et al. Am J Respir Cell Mol Biol. 2013 August; 49(2): 167-79; Barkauskas & Noble. Am J Physiol Cell Physiol. 2014 Jun. 1; 306(11): C987-96).

Unlike IPF, however, the fibrosis generated after intratracheal bleomycin is not progressive. Following intratracheal bleomycin, collagen content (as assessed by hydroxyproline assay) peaks around 21-28 days postinjury (Izbicki et al. Int J Exp Pathol. 2002 June; 83(3): 111-9). Recent reports and personal experience with this model suggest that the fibrosis induced by a single exposure to bleomycin is self-limited and can display some resolution/regression during the weeks following the injury (Chung et al. Am J Respir Cell Mol Biol. 2003 September; 29(3 Pt 1): 375-80; Lawson et al. Am J Pathol. 2005 November; 167(5): 1267-77; Rock et al. Proc Natl Acad Sci USA. 2011 Dec. 27; 108(52): E1475-83; Barkauskas & Noble. Am J Physiol Cell Physiol. 2014 Jun. 1; 306(11): C987-96).

Investigators have tried to optimize the bleomycin fibrosis model to better replicate the histology associated with human IPF. In one such study, a repetitive bleomycin model was developed in an attempt to recapitulate the recurrent alveolar injury that is hypothesized to drive IPF pathogenesis. Degryse et al. (Am J Physiol Lung Cell Mol Physiol. 2010 October; 299(4): L442-52) describe a model in which they administered intratracheal bleomycin biweekly up to eight times. The histology from this repetitive injury model revealed prominent hyperplastic AEC2s in areas of fibrosis as well as more of a temporally heterogeneous pattern of lung injury (i.e., fibrotic scar next to hyperplastic AEC2s next to normal tissue). Further, the fibrosis that developed seemed to persist until at least 10 weeks after the last bleomycin dose. While the histological results of this model do seem more consistent with human IPF, the time-intensive nature of this model may limit its applicability in the laboratory (Barkauskas & Noble. Am J Physiol Cell Physiol. 2014 Jun. 1; 306(11): C987-96).

Despite its imperfections, the bleomycin model of pulmonary fibrosis remains the most common in the study of fibrotic lung disease. Other fibrosis generating models include the following (reviewed in Moore et al. Am J Physiol Lung Cell Mol Physiol. 2008 February; 294(2): L152-60): granulomatous inflammation (Jakubzick et al Am J Pathol. 2003 May; 162(5): 1475-86), fluorescein isocyanate (Kolodsick et al. J Immunol. 2004 Apr. 1; 172(7): 4068-76; Roberts et al. J Pathol. 1995 July; 176(3): 309-18), irradiation-induced (McDonald et al. Radiother Oncol. 1993 March; 26(3): 212-8), adenosine deaminase deficiency (Chunn et al. Am J Physiol Lung Cell Mol Physiol. 2006 March; 290(3): L579-87), and murine gamma-herpesvirus (which is typically used to augment a fibrotic response to another stimulus) (Gangadharan et al. J Leukoc Biol. 2008 July; 84(1): 50-8; Lok et al. Eur Respir J. 2002 November; 20(5): 1228-32). While many investigators are now designing experiments with human IPF tissue/cells, the field at large still relies heavily on murine models of the disease. A murine model of IPF that recapitulates the disease more faithfully than bleomycin would be most welcome (Barkauskas & Noble. Am J Physiol Cell Physiol. 2014 Jun. 1; 306(11): C987-96).

To date, only limited treatments or therapies exist for the treatment of IPF, and there is a substantial unmet need for effective treatments that can alter the course of IPF by slowing or reversing disease progression. Many clinical trials have ended unsuccessfully after showing negligible patient benefit or high incidence of side effects.

The described invention involves a validated therapeutic target for the development of drugs for patients with progressive tissue fibrosis.

SUMMARY OF THE INVENTION

According to one aspect, the described invention provides a method for reducing progression of lung fibrosis after a lung injury comprising administering a therapeutic amount of a therapeutic agent, wherein the therapeutic amount is effective: (a) to modulate expression of a T-box transcription factor in a population of cells in lung; and (b) to reduce proliferation of the population of cells in lung expressing the T-box transcription factor.

According to some embodiments, the T-box transcription factor is T-box protein 4 (Tbx4).

According to some embodiments, the therapeutic agent is an siRNA of amino acid sequence 5'-rGrCrArCrUrGrCrCrArArGrArArArCrArUrGrGrArArArGGT-3' (SEQ ID NO: 1). According to some embodiments, the therapeutic agent is an siRNA of amino acid sequence 5'-rUrGrCrArArUrUrArUrCrUrArArGrArArArGrUrGrArCrUrUTG-3' (SEQ ID NO: 2). According to some embodiments, knockdown of Tbx4 with the siRNA is effective to reduce invasiveness of myofibroblasts. According to some embodiments, the therapeutic amount of the Tbx4 siRNA is effective to decrease TGFβ-induced release of hyaluronic acid (HA).

According to some embodiments, the population of cells in lung in which Tbx4 is expressed is heterogeneous. According to some embodiments, the population of cells in lung in which Tbx4 is expressed comprises one or more of a population of pericytes, a population of lipofibroblasts, a population of endothelial cells, or a population of myofibroblasts. According to some embodiments, the population of cells in lung in which Tbx4 is expressed is further characterized by expression of one or more markers selected from α-smooth muscle actin (αSMA), Col1a1, desmin, vimentin, NG2, and PDGFRβ.

According to some embodiments, the population of myofibroblasts in lung is characterized by expression of Tbx4 and αSMA.

According to some embodiments, the population of cells in lung in which Tbx4 is expressed comprises a population of fibroblasts resident in the lung of the subject.

According to some embodiments, inhibition of expression of Tbx4 is effective to modulate expression of Has-2.

According to some embodiments, the therapeutic amount of the therapeutic agent is effective to reduce symptoms of pulmonary fibrosis.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Glossary

Figure 1:
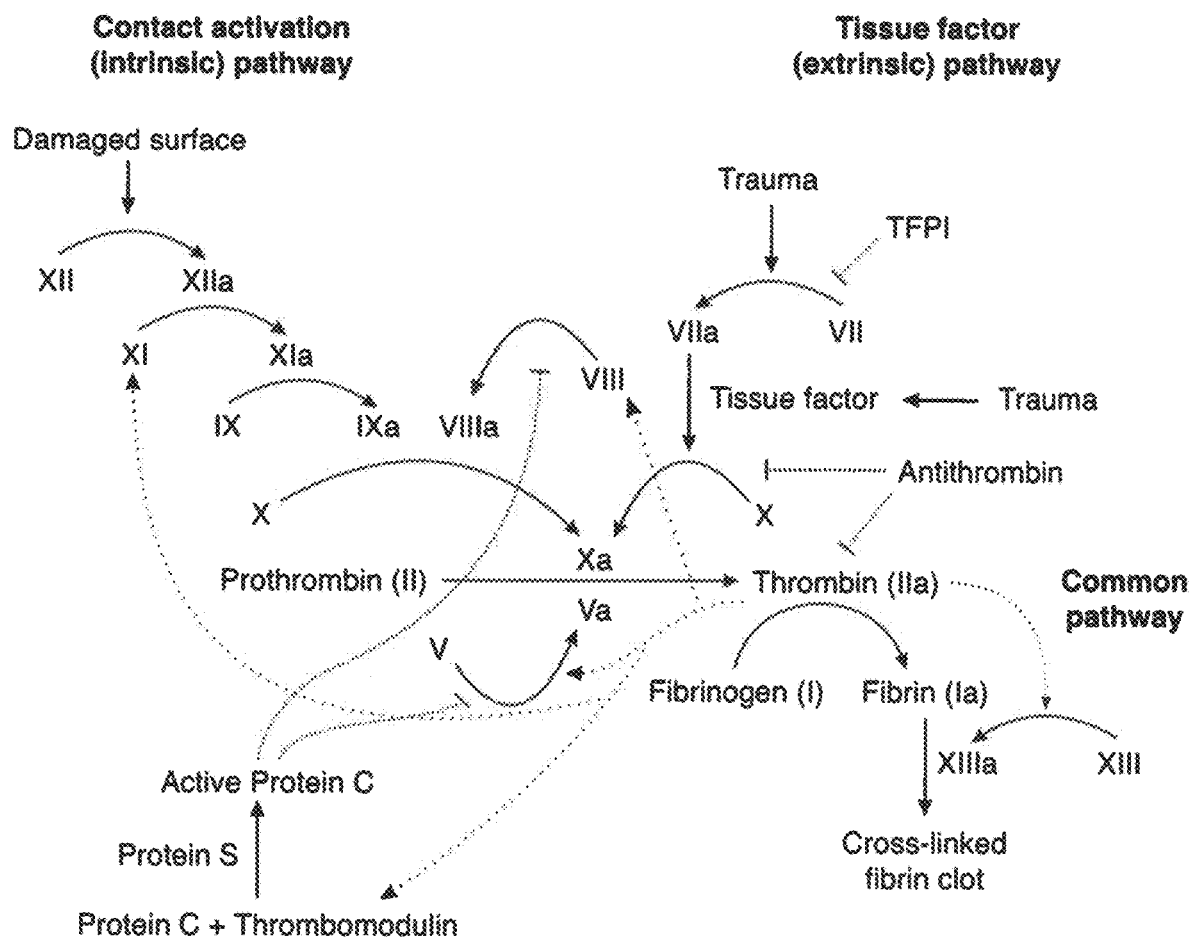
FIG. 1 shows the contact activation (intrinsic) and the tissue factor (extrinsic) coagulation pathways.
Figure 2:
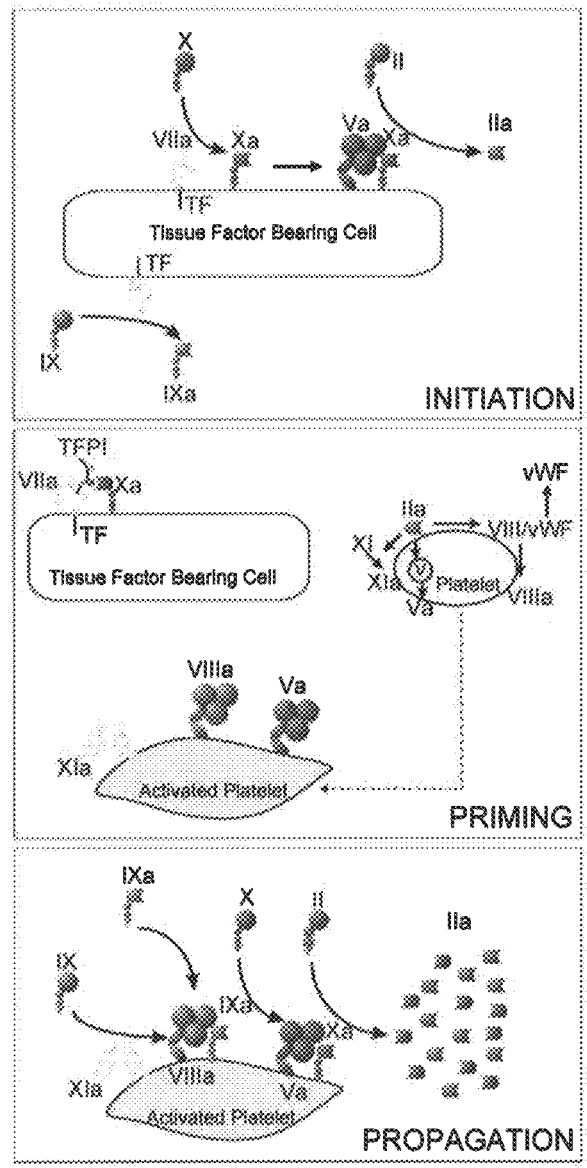
FIG. 2 shows a three stage cell-surface based model of coagulation, comprising initiation, priming, and propagation (Monroe et al. Arterioscler Thromb Vasc Biol. 2002 Sep. 1; 22:1381-1389).
Figure 3:
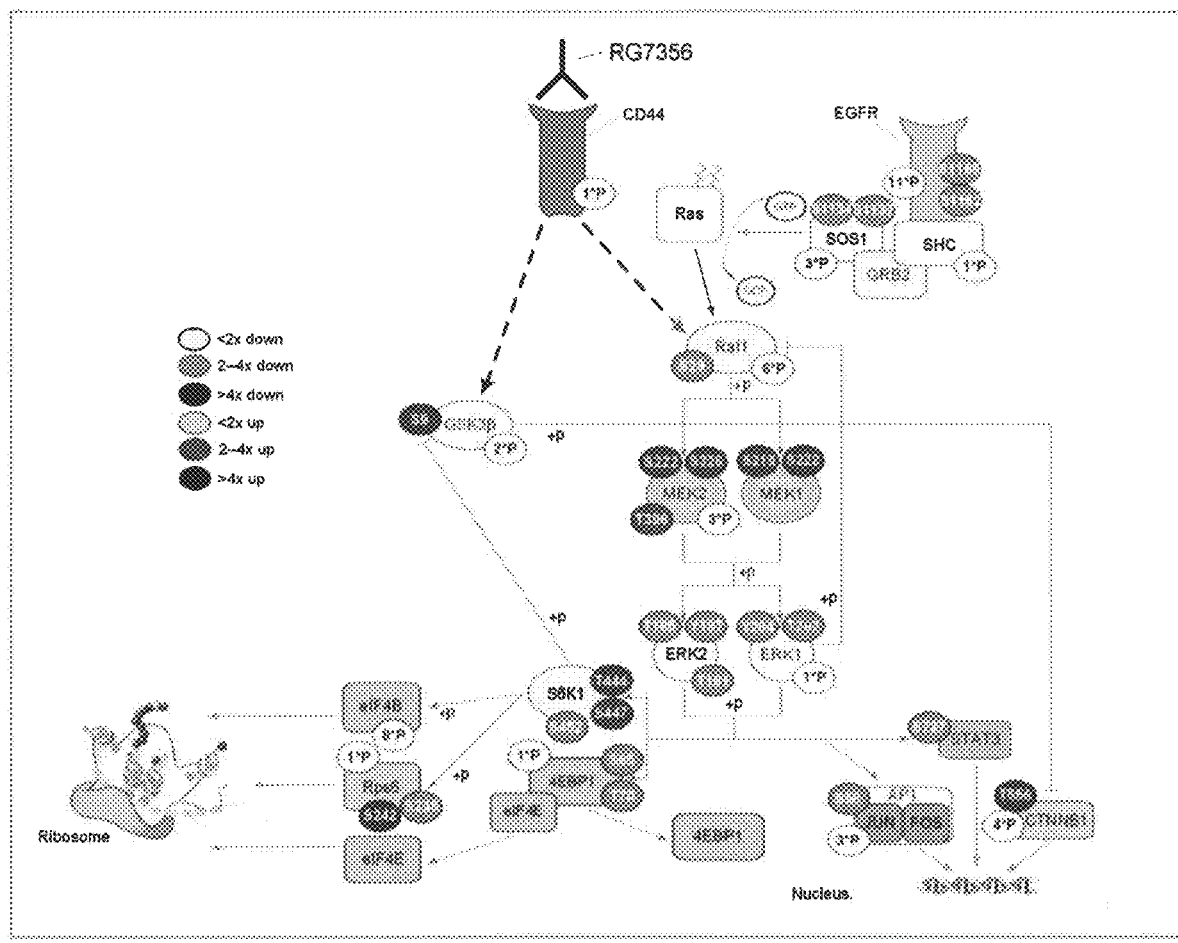
FIG. 3 depicts the role of CD44 in various pathways (Wiegand et al. Cancer Res. 2012 September; 72(17): 4329-39).
Figure 4:
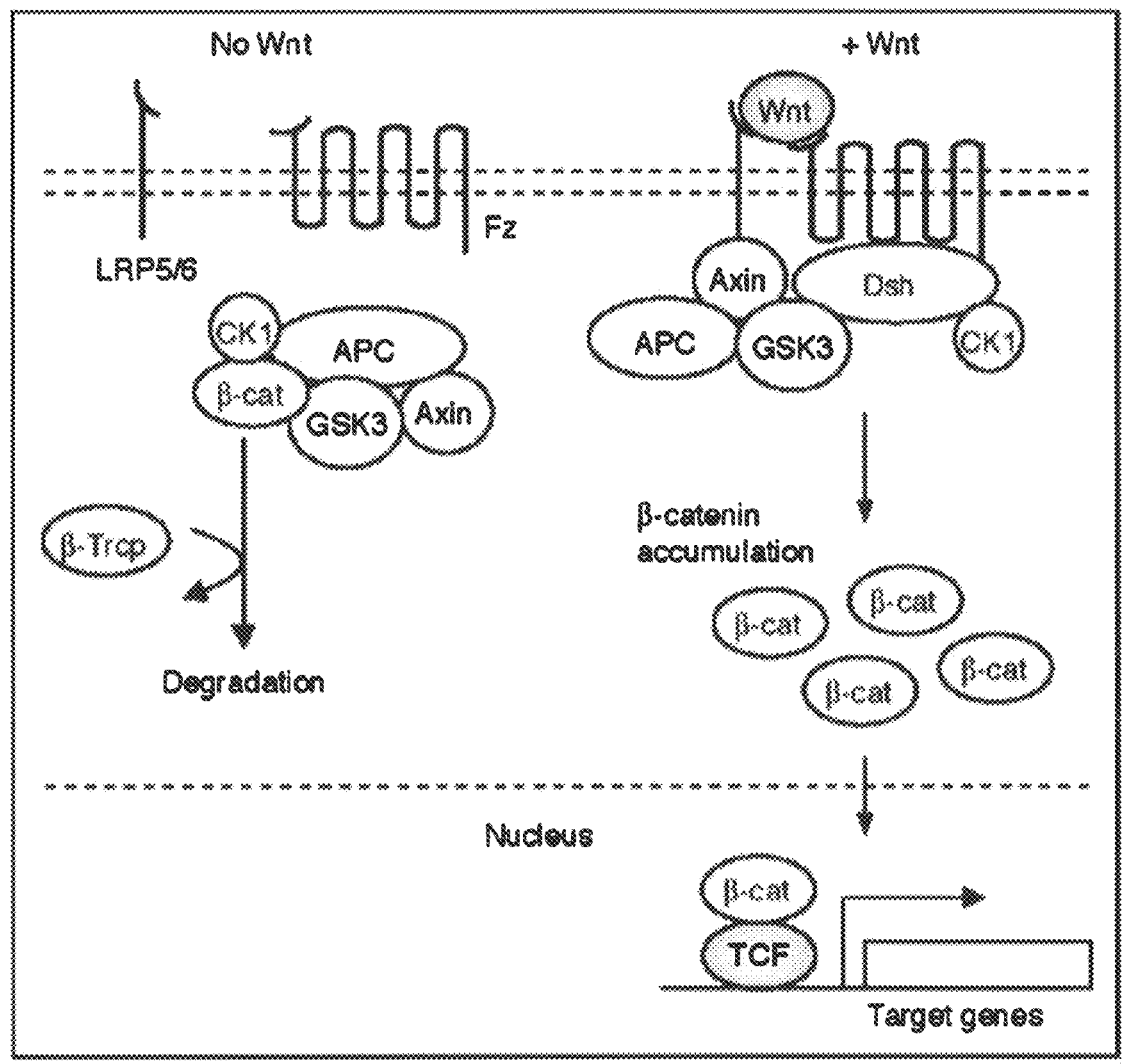
FIG. 4 depicts the canonical Wnt-β-catenin signal transduction cascade (Komiya & Habas. Organogenesis. 2008 April-June; 4(2): 68-75).
Figure 5:
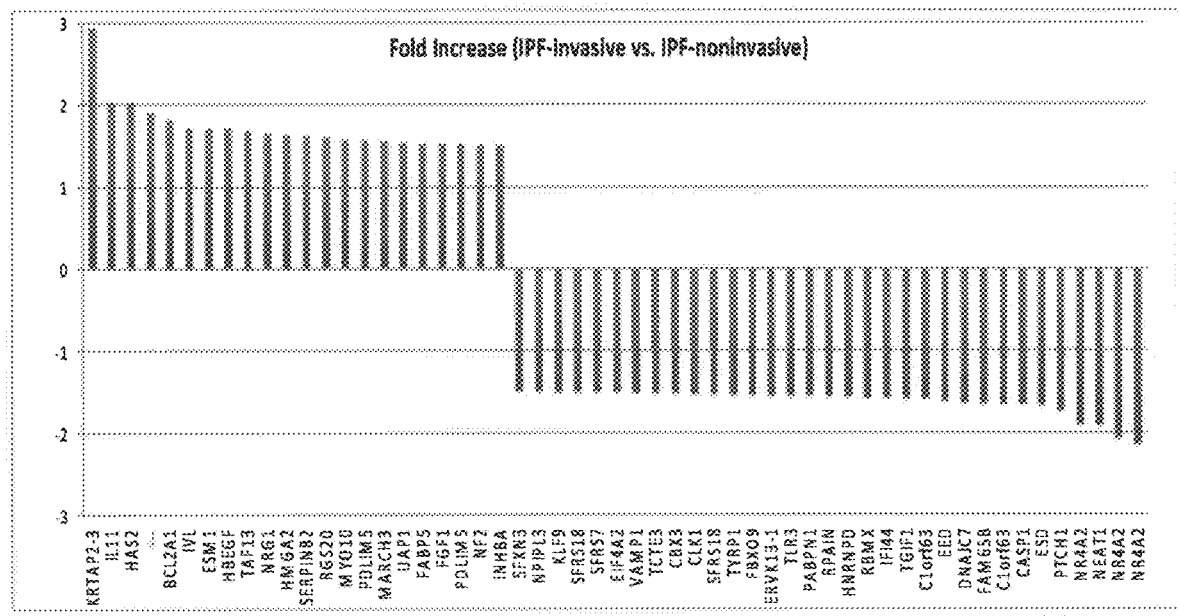
FIG. 5 shows a comparison of gene expression in invasive and non-invasive fibroblasts (normalized, in fold changes relative gene expression (in fold change)) by gene array analysis.
Figure 6:
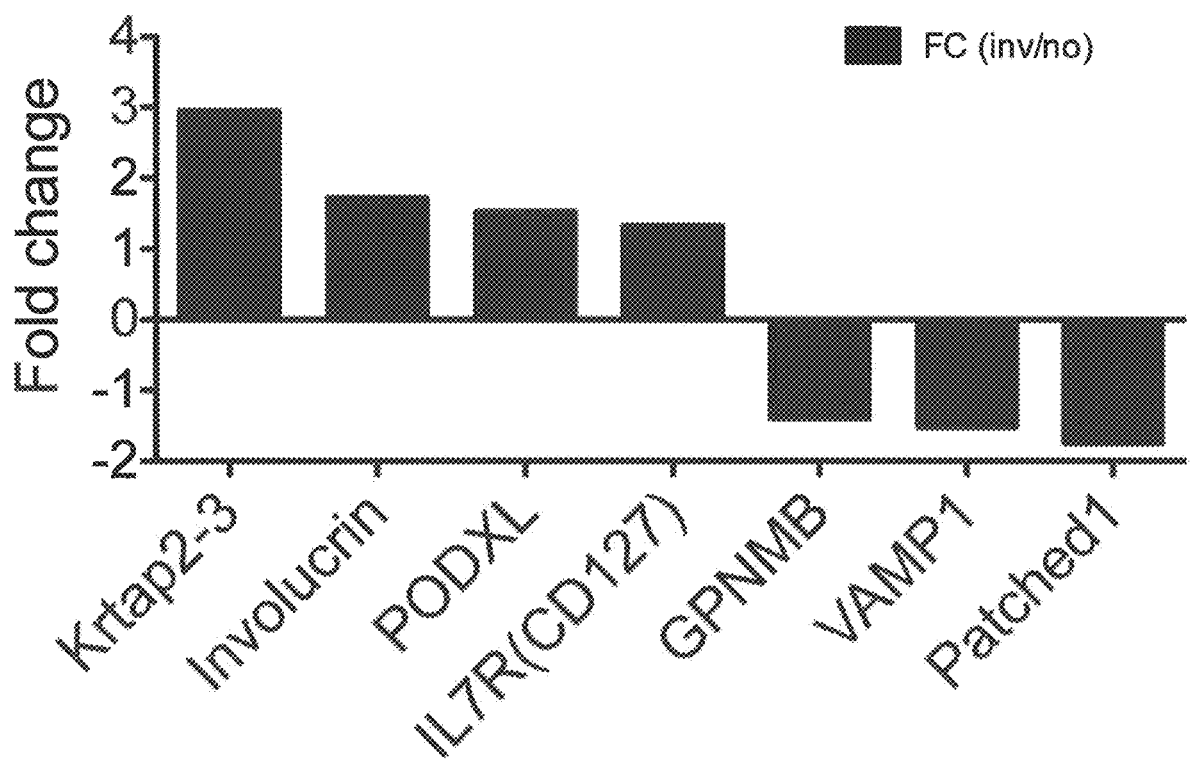
FIG. 6 shows a comparison of relative gene expression (in fold change) of transcription factors in invasive and non-invasive fibroblasts by gene array analysis.
Figure 7:
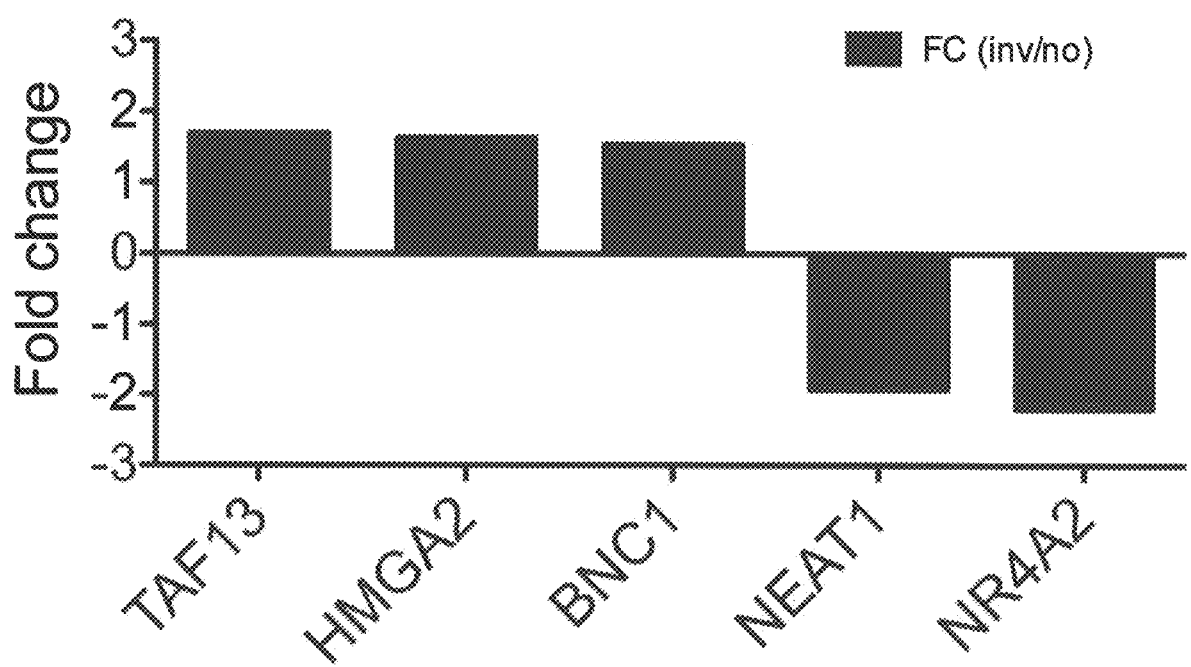
FIG. 7 shows a comparison of relative gene expression (in fold change) of cell surface molecules in invasive and non-invasive fibroblasts by gene array analysis.

The terms "amino acid residue" or "amino acid" or "residue" are used interchangeably to refer to an amino acid that is incorporated into a protein, a polypeptide, or a peptide, including, but not limited to, a naturally occurring amino acid and known analogs of natural amino acids that can function in a similar manner as naturally occurring amino acids.

The abbreviations used herein for amino acids are those abbreviations which are conventionally used: A=Ala=Alanine; R=Arg=Arginine; N=Asn=Asparagine;

D=Asp=Aspartic acid; C=Cys=Cysteine; Q=Gln=Glutamine; E=Glu=Glutamic acid; G=Gly=Glycine; H=His=Histidine; I=Ile=Isoleucine; L=Leu=Leucine; K=Lys=Lysine; M=Met=Methionine; F=Phe=Phenylalanine; P=Pro=Proline; S=Ser=Serine; T=Thr=Threonine; W=Trp=Tryptophan; Y=Tyr=Tyrosine; V=Val=Valine. The amino acids may be L- or D-amino acids. An amino acid may be replaced by a synthetic amino acid which is altered so as to increase the half-life of the peptide or to increase the potency of the peptide, or to increase the bioavailability of the peptide.

The following represent groups of amino acids that are conservative substitutions for one another:
Alanine (A), Serine (S), Threonine (T);
Aspartic Acid (D), Glutamic Acid (E);
Asparagine (N), Glutamine (Q);
Arginine (R), Lysine (K);
Isoleucine (I), Leucine (L), Methionine (M), Valine (V);
and Phenylalanine (F), Tyrosine (Y), Tryptophan (W).

Anatomical Terms

When referring to animals, that typically have one end with a head and mouth, with the opposite end often having the anus and tail, the head end is referred to as the cranial end, while the tail end is referred to as the caudal end. Within the head itself, rostral refers to the direction toward the end of the nose, and caudal is used to refer to the tail direction. The surface or side of an animal's body that is normally oriented upwards, away from the pull of gravity, is the dorsal side; the opposite side, typically the one closest to the ground when walking on all legs, swimming or flying, is the ventral side. On the limbs or other appendages, a point closer to the main body is "proximal"; a point farther away is "distal". Three basic reference planes are used in zoological anatomy. A "sagittal" plane divides the body into left and right portions. The "midsagittal" plane is in the midline, i.e. it would pass through midline structures such as the spine, and all other sagittal planes are parallel to it. A "coronal" plane divides the body into dorsal and ventral portions. A "transverse" plane divides the body into cranial and caudal portions.

When referring to humans, the body and its parts are always described using the assumption that the body is standing upright. Portions of the body which are closer to the head end are "superior" (corresponding to cranial in animals), while those farther away are "inferior" (corresponding to caudal in animals). Objects near the front of the body are referred to as "anterior" (corresponding to ventral in animals); those near the rear of the body are referred to as "posterior" (corresponding to dorsal in animals). A transverse, axial, or horizontal plane is an X-Y plane, parallel to the ground, which separates the superior/head from the inferior/feet. A coronal or frontal plane is a Y-Z plane, perpendicular to the ground, which separates the anterior from the posterior. A sagittal plane is an X-Z plane, perpendicular to the ground and to the coronal plane, which separates left from right. The midsagittal plane is the specific sagittal plane that is exactly in the middle of the body.

Structures near the midline are called medial and those near the sides of animals are called lateral. Therefore, medial structures are closer to the midsagittal plane, lateral structures are further from the midsagittal plane. Structures in the midline of the body are median. For example, the tip of a human subject's nose is in the median line.

Ipsilateral means on the same side, contralateral means on the other side and bilateral means on both sides. Structures that are close to the center of the body are proximal or central, while ones more distant are distal or peripheral. For example, the hands are at the distal end of the arms, while the shoulders are at the proximal ends.

The term "biomarkers" as used herein refers to are molecules or genes that carry information about the health or disease state of the individual. Generally speaking, biomarkers can be divided into several classes based on the type of the information that they provide. Diagnostic biomarkers allow the distinction of one disease from the other, and can be used in disease classification and diagnosis. Disease susceptibility markers—most often gene mutations and polymorphisms associated with the disease—are often included with diagnostic markers, but in fact differ because in the healthy individual they just indicate an increased risk and their diagnostic value is unclear in complex disease. Prognostic biomarkers are markers that allow the prediction of outcome, usually at the time of presentation. Diagnostic and prognostic markers should be distinguished from disease activity biomarkers that may change during the course of the disease—although in some cases they may overlap. The last group of biomarkers can be broadly defined as treatment efficacy biomarkers—these include markers that a drug is indeed affecting the pathway it is supposed to affect, markers that indicate toxicity and markers that indicate a real beneficial drug effect that could eventually be used as surrogate endpoints in drug studies (Zhang & Kaminski. Curr Opin Pulm Med. 2012 September; 18(5): 441-6).

The term "bronchoalveolar lavage" (BAL) as used herein refers a medical procedure in which a bronchoscope is passed through the mouth or nose into the lungs and fluid is squirted into a small part of the lung and then collected for examination.

The term "5-bromo-2-deoxyuridine" (BrdU) as used herein refers to a thymidine analog, which is readily incorporated in replicating DNA in dividing cells. BrdU is utilized as a tool to measure cell proliferation with anti-BrdU antibodies.

The term "CC10" as used herein refers a 10 kDa protein, which is the major secretory protein of club cells, and is thought to play a protective role in the lung (Bolton et al. Toxicol Pathol. 2008 April; 36(3): 440-8).

The term "cell line" as used herein refers to a population of cultured cells that has undergone a change allowing the cells to grow indefinitely.

The term "cell strain" as used herein refers to a population of cultured cells that has a finite life span.

The term "CFP" as used herein refers to cyan fluorescent protein, which possesses bright fluorescence with excitation/emission maxima at 458 and 480 nm, respectively.

The term "complementary" as used herein refers to two nucleic acid sequences or strands that can form a perfect base-paired double helix with each other.

The term "Confetti" as used herein refers to a reporter construct that functions as a stochastic multicolor Cre recombinase reporter of multiple fluorescent proteins from a single genomic locus. This enables a way to label and distinguish individual/adjacent cells with nuclear localized, membrane-targeted, or cytoplasmic fluorescent proteins in Cre recombined cells.

The term "Col1a1" as used herein refers to a marker for the pro-alpha 1 chain of type I collagen.

The term "Col1a2" as used herein refers to the gene encoding the pro-alpha 2 chain of type I collagen. IPF patients have been found to have increased expression levels of Col1a2 (Konishi et al. Am J Respir Crit Care Med. 2009 Jul. 15; 180(2): 167-75).

The term "chondroitin sulfate proteoglycan 4" (CSPG4) as used herein refers to the human homolog of NG2. NG2 is a proteoglycan marker for macrophages and pericytes.

The term "Cre-lox system" as used herein refers to a sophisticated tool for general knockouts, conditional knockouts, and reporter strains. The Cre-lox mechanism was discovered in P1 bacteriophage (Sauer & Henderson. J Mol Biol. 1988; 85: 5166-70; Sternberg & Hamilton. J Mol Biol. 1981; 150: 467-86), and requires only two components: 1) Cre recombinase, an enzyme that catalyzes recombination between two loxP sites; and 2) LoxP sites, specific 34-base pair (bp) sequences consisting of an 8-bp core sequence, where recombination takes place, and two flanking 13-bp inverted repeats. The term "CreER" refers to a fusion of Cre and a tamoxifen-responsive estrogen receptor, and is commonly used in fate mapping studies.

The term "desmin" as used herein refers to a protein found in intermediate filaments that copolymerizes with vimentin to form constituents of connective tissue, cell wells, filaments etc. It is found in the Z disk of skeletal and cardiac muscle cells. (Paulin & Li. Exp Cell Res. 2004 Nov. 15; 301(1): 1-7))

The term "downstream" with respect to a gene, refers to the direction RNA polymerase moves during transcription, which is toward the end of the template DNA strand with a 3' hydroxyl group. The term "upstream" is the direction on a DNA opposite to the direction RNA polymerase moves during transcription.

The term "EGFP" as used herein refers to enhanced green fluorescent protein, a protein composed of 238 amino acid residues (26.9 kDa) that exhibits bright green fluorescence when exposed to light in the blue to ultraviolet range.

The term "epithelial-mesenchymal transition" (EMT) as used herein refers to a biological process that allows a polarized epithelial cell, which normally interacts with basement membrane via its basal surface, to underdo multiple biochemical changes that enable it to assume a mesenchymal cell phenotype, which includes enhanced migratory capacity, invasiveness, elevated resistance to apoptosis, and greatly increased production of ECM components (Kalluri & Neilson. J Clin Invest. 2003 December; 112(12): 1776-84). A number of distinct molecular processes are engaged in order to initiate EMT and enable it to reach completion, including activation of transcription factors, expression of specific cell-surface proteins, reorganization and expression of cytoskeletal proteins, production of ECM-degrading enzymes, and changes in the expression of specific microRNAs (Kalluri & Weinberg. J Clin Invest. 2009 June; 119(6): 1420-8).

The term "expression vector" as used herein refers to a modified DNA molecule that carries a gene or DNA which is specially constructed into a suitable host cell and there directs synthesis of a protein product encoded by an inserted sequence.

The term "FACS" as used herein, refers to fluorescence-activated cell sorting, a specialized form of flow cytometry.

The term "fate mapping" as used herein refers to methods of elucidating how embryonic tissue organization relates to postnatal tissue structure and function, and is used in studying the etiology of human disorders (Jensen & Dymecki. Methods Mol Biol. 2014; 1092: 437-54). When carried out at single-cell resolution, fate mapping is also known as cell lineage tracing. In cell lineage tracing a single cell is marked in such a way that the mark is transmitted to the cell's progeny, resulting in a set of labeled clones, providing information about the number of progeny of the founder cell, their location, and their differentiation status (Kretzschmar & Watt. Cell. 2012 Jan. 20; 148(1-2): 33-45).

The term "fibroblast" as used herein refers to a connective tissue cell that secretes collagen and other components of the extracellular matrix, which migrates and proliferates during normal wound healing.

The term "flow cytometry" as used herein refers to a tool for interrogating the phenotype and characteristics of cells. Flow cytometry is a system for sensing cells or particles as they move in a liquid stream through a laser (light amplification by stimulated emission of radiation)/light beam past a sensing area. The relative light-scattering and color-discriminated fluorescence of the microscopic particles is measured. Analysis and differentiation of the cells is based on size, granularity, and whether the cells are carrying fluorescent molecules in the form of either antibodies or dyes. As the cell passes through the laser beam, light is scattered in all directions, and the light scattered in the forward direction at low angles (0.5-10 degrees) from the axis is proportional to the square of the radius of a sphere and so to the size of the cell or particle. Light may enter the cell; thus, the 90 degree light (right-angled, side) scatter may be labeled with fluorochrome-linked antibodies or stained with fluorescent membrane, cytoplasmic, or nuclear dyes. Thus, the differentiation of cell types, the presence of membrane receptors and antigens, membrane potential, pH, enzyme activity, and DNA content may be facilitated. Flow cytometers are multiparameter, recording several measurements on each cell; therefore, it is possible to identify a homogeneous subpopulation within a heterogeneous population (Marion G. Macey, Flow cytometry: principles and applications, Humana Press, 2007).

The term "FoxD1" as used herein refers to a gene encoding a protein, forkhead box D1, which belongs to the forkhead family of transcription factors, which are characterized by a distinct forkhead domain. The lung contains an extensive population of FoxD1 progenitor-derived pericytes that are an important lung myofibroblast precursor population (Hung C, et al. Am J Respir Crit Care Med. 2013 Oct. 1; 188(7): 820-30).

The term "FoxJ1" as used herein refers to a gene encoding a protein, forkhead box J1, which belongs to the forkhead family of transcription factors, which are characterized by a distinct forkhead domain. FoxJ1 is required for cilia formation and regulates basal body anchoring to the cytoskeleton of ciliated pulmonary epithelial cells (Gomperts B N, et al. J Cell Sci. 2004 Mar. 15; 117(Pt 8): 1329-37).

The term "gene" as used herein is the entire DNA sequence, including exons, introns, and noncoding transcription-control regions necessary for production of a functional protein or RNA.

The terms "gene expression" or "expression" are used interchangeably to refer to the process by which information encoded in a gene is converted into an observable phenotype.

The term "growth" as used herein refers to a process of becoming larger, longer or more numerous, or an increase in size, number, or volume.

The term "interfere" or "to interfere with" as used herein refers to the hampering, impeding, dampening, hindering, obstructing, blocking, reducing or preventing of an action or occurrence.

The term "invasion" or "invasiveness" as used herein refers to a process that includes penetration of and movement through surrounding tissues.

The term "involucrin" as used herein refers to a component of the keratinocyte crosslinked envelope, is found in the cytoplasm and crosslinked to membrane proteins by transglutaminase.

The term "knockdown" or "knockout" are used interchangeably to refer to selectively inactivating a gene.

The term "knock-in" as used herein refers to a genetic engineering method that involves the insertion of a protein coding cDNA sequence at a particular locus in a target organism's chromosome (Gibson, Greg (2009). A Primer of Genome Science 3rd ed. Sunderland, Mass.: Sinauer. pp. 301-302).

The term "lipofibroblast" as used herein refers to a lipid-containing alveolar interstitial fibroblast recognizable by characteristic lipid droplets. Lipofibroblasts participate in the synthesis of ECM proteins, including collagen and elastin, and produce leptin, which binds to AEC2s, stimulating their production of surfactant (Rehan & Torday. PPAR Res. 2012; 2012: 289867).

The term "Masson's trichrome stain" as used herein refers to a stain used in the study of connective tissue, muscle and collagen fibers. It is used primarily for distinguishing collagen from muscle tissue. Typically, it contains nuclear, collagenous, and cytoplasmic dyes in mordants, such as phosphotungstic or phosphomolybdic acid.

The term mCherry" as used herein refers to a 28.8 kDa red fluorescent protein with 256 amino acids.

The term "migration" as used herein refers to movement of a cell from one place or location to another.

The term "modulate" as used herein means to regulate, alter, adapt, or adjust to a certain measure or proportion.

The term "mT/mG" as used herein refers to a double-fluorescent Cre reporter allele that expresses cell membrane-localized red fluorescence in widespread cells and tissues prior to Cre recombinase exposure, and cell membrane-localized green fluorescence in Cre recombinase expressing cells (and future cell lineages derived from these cells).

The term "NG2" as used herein refers to neural/glial antigen. NG2 is found in the plasma membrane of many cell types, and has been reported to be expressed exclusively by pericytes during vascular morphogenesis (Ozerdem et al. Dev Dyn. 2001 October; 222(2): 218-27).

The term "nucleic acid" is used herein to refer to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

The term "nucleotide" is used herein to refer to a chemical compound that consists of a heterocyclic base, a sugar, and one or more phosphate groups. In the most common nucleotides, the base is a derivative of purine or pyrimidine, and the sugar is the pentose deoxyribose or ribose. Nucleotides are the monomers of nucleic acids, with three or more bonding together in order to form a nucleic acid. Nucleotides are the structural units of RNA, DNA, and several cofactors, including, but not limited to, CoA, FAD, DMN, NAD, and NADP. Purines include adenine (A), and guanine (G); pyrimidines include cytosine (C), thymine (T), and uracil (U).

The term "oligonucleotide" as used herein refers to relatively short (13-25 nucleotides) unmodified or chemically modified single-stranded DNA molecules.

The following terms are used herein to describe the sequence relationships between two or more nucleic acids or polynucleotides: (a) "reference sequence", (b) "comparison window", (c) "sequence identity", (d) "percentage of sequence identity", and (e) "substantial identity".

The term "reference sequence" refers to a sequence used as a basis for sequence comparison. A reference sequence may be a subset or the entirety of a specified sequence; for example, as a segment of a full-length cDNA or gene sequence, or the complete cDNA or gene sequence.

The term "comparison window" refers to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be at least 30 contiguous nucleotides in length, at least 40 contiguous nucleotides in length, at least 50 contiguous nucleotides in length, at least 100 contiguous nucleotides in length, or longer. Those of skill in the art understand that to avoid a high similarity to a reference sequence due to inclusion of gaps in the polynucleotide sequence, a gap penalty typically is introduced and is subtracted from the number of matches.

Methods of alignment of sequences for comparison are well-known in the art. Optimal alignment of sequences for comparison may be conducted by the local homology algorithm of Smith and Waterman, Adv. Appl. Math. 2:482 (1981); by the homology alignment algorithm of Needleman and Wunsch, J. Mol. Biol. 48:443 (1970); by the search for similarity method of Pearson and Lipman, Proc. Natl. Acad. Sci. 85:2444 (1988); by computerized implementations of these algorithms, including, but not limited to: CLUSTAL in the PC/Gene program by Intelligenetics, Mountain View, Calif.; GAP, BESTFIT, BLAST, FASTA, and TFASTA in the Wisconsin Genetics Software Package, Genetics Computer Group (GCG), 575 Science Dr., Madison, Wis., USA; the CLUSTAL program is well described by Higgins and Sharp, Gene 73:237-244 (1988); Higgins and Sharp, CABIOS 5:151-153 (1989); Corpet, et al., Nucleic Acids Research 16:10881-90 (1988); Huang, et al., Computer Applications in the Biosciences 8:155-65 (1992), and Pearson, et al., Methods in Molecular Biology 24:307-331 (1994). The BLAST family of programs, which can be used for database similarity searches, includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, Current Protocols in Molecular Biology, Chapter 19, Ausubel, et al., Eds., Greene Publishing and Wiley-Interscience, New York (1995).

Unless otherwise stated, sequence identity/similarity values provided herein refer to the value obtained using the BLAST 2.0 suite of programs using default parameters. Altschul et al., Nucleic Acids Res. 25:3389-3402 (1997). Software for performing BLAST analyses is publicly available, e.g., through the National Center for Biotechnology-Information at ncbi.nlm.nih.gov. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits then are extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, a cutoff of 100, M=5, N=−4, and a comparison of both strands. For amino acid sequences, the BLASTP program uses as defaults a word length (W) of 3, an expectation (E) of 10, and the BLOSUM62 scoring matrix (see Henikoff & Henikoff, Proc. Natl. Acad. Sci. USA, 1989, 89:10915).

In addition to calculating percent sequence identity, the BLAST algorithm also performs a statistical analysis of the similarity between two sequences (see, e.g., Karlin & Altschul, Proc. Natl. Acad. Sci. USA, 1993, 90: 5873-5787). One measure of similarity provided by the BLAST algorithm is the smallest sum probability (P(N)), which provides an indication of the probability by which a match between two nucleotide or amino acid sequences would occur by chance. BLAST searches assume that proteins may be modeled as random sequences. However, many real proteins comprise regions of nonrandom sequences, which may be homopolymeric tracts, short-period repeats, or regions enriched in one or more amino acids. Such low-complexity regions may be aligned between unrelated proteins even though other regions of the protein are entirely dissimilar. A number of low-complexity filter programs may be employed to reduce such low-complexity alignments. For example, the SEG (Wooten and Federhen, Comput. Chem., 1993, 17:149-163) and XNU (Claverie and States, Comput. Chem., 1993, 17:191-201) low-complexity filters may be employed alone or in combination.

As used herein, "sequence identity" or "identity" in the context of two nucleic acid or polypeptide sequences refers to the residues in the two sequences which are the same when aligned for maximum correspondence over a specified comparison window. When percentage of sequence identity is used in reference to proteins it is recognized that residue positions that are not identical often differ by conservative amino acid substitutions, i.e., where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, Computer Applic. Biol. Sci., 1988, 4:11-17, e.g., as implemented in the program PC/GENE (Intelligenetics, Mountain View, Calif., USA).

As used herein, "percentage of sequence identity" means the value determined by comparing two optimally aligned sequences over a comparison window, wherein the portion of the polynucleotide sequence in the comparison window may comprise additions or deletions (i.e., gaps) relative to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The term "substantial identity" of polynucleotide sequences means that a polynucleotide comprises a sequence that has at least 70% sequence identity, at least 80% sequence identity, at least 90% sequence identity and at least 95% sequence identity, compared to a reference sequence using one of the alignment programs described using standard parameters. One of skill will recognize that these values may be adjusted appropriately to determine corresponding identity of proteins encoded by two nucleotide sequences by taking into account codon degeneracy, amino acid similarity, reading frame positioning and the like. Substantial identity of amino acid sequences for these purposes normally means sequence identity of at least 60%, or at least 70%, at least 80%, at least 90%, or at least 95%. Another indication that nucleotide sequences are substantially identical is if two molecules hybridize to each other under stringent conditions. However, nucleic acids that do not hybridize to each other under stringent conditions are still substantially identical if the polypeptides that they encode are substantially identical. This may occur, e.g., when a copy of a nucleic acid is created using the maximum codon degeneracy permitted by the genetic code. One indication that two nucleic acid sequences are substantially identical is that the polypeptide that the first nucleic acid encodes is immunologically cross reactive with the polypeptide encoded by the second nucleic acid.

The terms "substantial identity" in the context of a peptide indicates that a peptide comprises a sequence with at least 70% sequence identity to a reference sequence, at least 80%, at least 85%, at least 90% or 95% sequence identity to the reference sequence over a specified comparison window. Optionally, optimal alignment is conducted using the homology alignment algorithm of Needleman and Wunsch, J. Mol. Biol. 48:443 (1970). An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides which are "substantially similar" share sequences as noted above except that residue positions that are not identical may differ by conservative amino acid changes.

The term "PDGFRβ" as used herein refers to platelet derived growth factor receptor beta.

The term "peptidomimetic" refers to a small protein-like chain designed to mimic or imitate a peptide. A peptidomimetic may comprise non-peptidic structural elements capable of mimicking (meaning imitating) or antagonizing (meaning neutralizing or counteracting) the biological action(s) of a natural parent peptide.

The term "pericytes" as used herein refer to perivascular cells (cells situated or occurring around a blood vessel) that wrap around capillaries. Pericytes are also known as mural cells, Rouget cells, or, because of their contractile fibers, as vascular smooth muscle cells. Pericytes have roles in angiogenesis, and blood vessel maintenance (Bergers & Song. Neuro Oncol. 2005 October; 7(4): 452-64).

The term "phenotype" as used herein refers to the observable characteristics of a cell, for example, expression of a protein.

The term "podoplanin" (PDPN or T1α) as used herein refers to a well-conserved mucin-type transmembrane protein widely distributed in human tissues that plays a critical role in development of the heart, lungs and lymphatic system. It is widely used as a marker for lymphatic endothelial cells and fibroblastic reticular cells of lymphoid organs and for lymphatics in the skin and tumor microenvironment. Tumor cells often upregulate PDPN as they undergo EMT; this upregulation is correlated with increased motility and metastasis (Astarita J L, et al. Front Immunol. 2012 Sep. 12; 3: 283).

The term "polynucleotide" refers to a deoxyribopolynucleotide, ribopolynucleotide, or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide(s). A polynucleotide may be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides.

The terms "polypeptide", "peptide" and "protein" are used interchangeably herein to refer to a polymer formed from the linking together, in a defined order, of amino acid residues. The link between one amino acid residue and the next is known as an amide or peptide bond. The term "polypeptide" as used herein refers to a single chain of amino acids, and a "protein" refers to one or more polypeptides. The terms apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein that protein is specifically reactive to antibodies elicited to the same protein but consisting entirely of naturally occurring amino acids. The terms "peptide", "polypeptide" and "protein" also apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein that protein is specifically reactive to antibodies elicited to the same protein but consisting entirely of naturally occurring amino acids. The terms "polypeptide", "peptide" and "protein" also are inclusive of modifications including, but not limited to, glycosylation, lipid attachment, sulfation, gamma-carboxylation of glutamic acid residues, hydroxylation and ADP-ribosylation. It will be appreciated, as is well known and as noted above, that polypeptides may not be entirely linear. For instance, polypeptides may be branched as a result of ubiquitination, and they may be circular, with or without branching, generally as a result of posttranslational events, including natural processing event and events brought about by human manipulation which do not occur naturally. Circular, branched and branched circular polypeptides may be synthesized by non-translation natural process and by entirely synthetic methods, as well.

The term "primer" refers to a nucleic acid which, when hybridized to a strand of DNA, is capable of initiating the synthesis of an extension product in the presence of a suitable polymerization agent. The primer is sufficiently long to uniquely hybridize to a specific region of the DNA strand. A primer also may be used on RNA, for example, to synthesize the first strand of cDNA.

The term "proliferate" and its other grammatical forms as used herein means multiplying or increasing in number.

The term "progression" as used herein refers to the course of a disease, such as pulmonary fibrosis, as it becomes worse. The term "progression-free survival" as used herein refers to the length of time during and after treatment of a disease that a patient lives with the disease but it does not get worse.

The term "promoter" as used herein refers to a region of DNA upstream, whether downstream, proximal, or distal, from the start of transcription, which is involved in recognition and binding of RNA polymerase and other proteins to initiate transcription. A given promoter may work in concert with other regulatory regions (enhancers, silencers, boundary elements/insulators) in order to direct the level of transcription of a given gene.

The term "inducible promoter" as used herein refers to a promoter whose downstream transcriptional activity is controlled by the presence of a molecule (i.e., inducer).

The term "constitutive promoter" refers to a promoter whose transcriptional activity is maintained at a relatively constant level in all cells of an organism without regard to cell environmental conditions.

The term "quantitative real-time reverse transcription PCR" or "real-time quantitative reverse transcription PCR" (Real-Time qRT-PCR) refers a PCR technology that enables reliable detection and measurement of products generated during each cycle of the PCR process. RNA is used as the starting material, which is transcribed into complementary DNA (cDNA) by reverse transcriptase; the cDNA is used as the template for the quantitative PCR reaction.

The term "reduce" and its various grammatical forms as used herein refer to a diminution, a decrease, an attenuation or abatement of the degree, intensity, extent, size, amount, density or number of occurrences, events or characteristics.

The term "RFP" as used herein refers to red fluorescent protein, which can be excited by the 488 nm or 532 nm laser line and is optimally detected at 588 nm.

RNA interference (RNAi), or Post-Transcriptional Gene Silencing (PTGS) is a conserved biological response to double-stranded RNA that mediates resistance to both endogenous parasitic and exogenous pathogenic nucleic acids, and regulates the expression of protein-coding genes. It is a natural process by which double-stranded RNAs initiate the degradation of homologous RNA; researchers can take advantage of this process to study gene expression. A simplified model for the RNAi pathway is based on two steps, each involving ribonuclease enzyme. In the first step, the trigger RNA (either dsRNA or miRNA primary transcript) is processed into a short, interfering RNA (siRNA) by the RNase II enzymes Dicer and Drosha. In the second step, siRNAs are loaded into the effector complex RNA-induced silencing complex (RISC). The siRNA is unwound during RISC assembly and the single-stranded RNA hybridizes with a mRNA target. Gene silencing is a result of nucleolytic degradation of the targeted mRNA by the RNase H enzyme Argonaute (Slicer).

Gene silencing, however, can also occur not via siRNA-mediated cleavage of targeted mRNA, but rather, via translational inhibition. If the siRNA/mRNA duplex contains mismatches the mRNA is not cleaved; in these cases, direct translational inhibition may occur, especially when high concentrations of siRNA are present. The mechanism of this translation inhibition is not known.

As a result, siRNA can elicit two distinct modes of post-transcriptional repression. Because the requirement for target complementarity is less stringent for direct translational inhibition than for target mRNA cleavage, siRNAs designed for the latter may inadvertently trigger the former in another gene. Therefore, siRNAs designed against one gene may trigger silencing of an unrelated gene.

The term "Rosa26" as used herein refers to a locus widely used for achieving general expression in mice.

The term "Scgb1a1" as used herein refers to secretoglobin, family 1a, member 1, or uteroglobin, an evolutionary conserved, steroid-inducible secreted protein that has anti-inflammatory and immunomodulatory properties. Mucosal epithelia of virtually all organs that communicate with the external environment express Scgb1a1, and Scgb1a1 is present in blood, urine, and other body fluids (Mukherjee et al. Endocr Rev. 2007 December; 28(7): 707-25).

The term "Sftpc" or "SPC" as used herein refers to pulmonary-associated surfactant protein C, an extremely hydrophobic surfactant protein essential for lung function and homeostasis after birth. It is produced exclusively by AEC2s in the lung. Pulmonary surfactant is a lipid-rich material comprising phosopholipids and other surfactant-associated proteins, and prevents lung collapse by reducing surface tension at the air-liquid interface in the alveoli of the lung (Clark & Clark. Semin Fetal Neonatal Med. 2005 June; 10(3): 271-82).

shRNA (short hairpin RNA) sequences offer the possibility of prolonged gene silencing. shRNAs are usually encoded in a DNA vector that can be introduced into cells via plasmid transfection or viral transduction. There are two main categories of shRNA molecules based on their design: simple stem-loop and microRNA-adapted shRNA. A simple stem-loop shRNA is often transcribed under the control of an RNA Polymerase III (Pol III) promoter [Bartel, DP, MicroRNAs: genomics, biogenesis, mechanism, and function. Cell 116(2):281-297 (2004), Kim, V. N. MicroRNA biogenesis: coordinated cropping and dicing. Nature Reviews, Molecular Cell Biology 6(5):376-385 (2005)]. The 50-70 nucleotide transcript forms a stem-loop structure consisting of a 19 to 29 bp region of double stranded RNA (the stem) bridged by a region of predominantly single-stranded RNA (the loop) and a dinucleotide 3' overhang [Brummelkamp, T. R. et al. (2002) A system for stable expression of short interfering RNAs in mammalian cells. Science 296(5567):550-553; Paddison, P. J. et al. (2002) Stable suppression of gene expression by RNAi in mammalian cells. PNAS 99(3):1443-1448; Paul, C. P. et al. (2002) Effective expression of small interfering RNA in human cells. Nature Biotechnology 20(5):505-508]. The simple stem-loop shRNA is transcribed in the nucleus and enters the RNAi pathway similar to a pre-microRNA. The longer (>250 nucleotide) microRNA-adapted shRNA is a design that more closely resembles native pri-microRNA molecules, and consists of a shRNA stem structure which may include microRNA-like mismatches, bridged by a loop and flanked by 5' and 3' endogenous microRNA sequences [Silva, J. M. et al. (2005) Second-generation shRNA libraries covering the mouse and human genomes. Nature Genetics 37(11):1281-1288.]. The microRNA-adapted shRNA, like the simple stem-loop hairpin, is also transcribed in the nucleus but is thought to enter the RNAi pathway earlier similar to an endogenous pri-microRNA.

The term "small interfering RNAs," which comprises both microRNA (miRNA) and small interfering RNA (siRNA), are small noncoding RNA molecules that play a role in RNA interference. siRNAs are synthesized from double-stranded segments of matched mRNA via RNA-dependent RNA polymerase., and siRNAs regulate the degradation of mRNA molecules identical in sequence to that of the corresponding siRNA, resulting in the silencing of the corresponding gene and the shutting down of protein synthesis. The main mechanism of action of siRNA is the mRNA cleavage function. There are no genes that encode for siRNAs. siRNAs can also silence gene expression by triggering promoter gene methylation and chromatin condensation. miRNAs are synthesized from an unmatched segment of RNA precursor featuring a hairpin turn, and miRNAs are encoded by specific miRNA genes as short hairpin pri-miRNAs in the nucleus. miRNAS are also small noncoding RNAs, but they seem to require only a 7- to 8-base-pair "seed" match between the 5' region of the miRNA and the 3'UTR of the target. While the majority of miRNA targets are translationally repressed, degradation of the target mRNA can also occur. The main mechanism of action of miRNA may be the inhibition of mRNA translation, although the cleavage of mRNA is also an important role (Ross et al. Am J Clin Pathol. 2007; 128(5): 830-36).

The term "αSMA" as used herein refers to alpha-smooth muscle actin, an actin isoform typical of vascular smooth muscle cells, which has been found to play a role in fibroblast contractile activity (Hinz et al. Mol Biol Cell. 2001 September; 12(9): 2730-41).

The term "specifically hybridizes" as used herein refers to the process whereby a nucleic acid distinctively or definitively forms base pairs with complementary regions of at least one strand of the nucleic acid target sequence that was not originally paired to the nucleic acid. A nucleic acid that selectively hybridizes undergoes hybridization, under stringent hybridization conditions, of the nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 80% sequence identity, at least 85% sequence identity, at least 90% sequence identity, at least 95% sequence identity, or at least 100% sequence identity (i.e., complementary) with each other. The term "survival rate" as used herein refers to the percentage of a population that are still alive for a certain period of time after treatment.

The term "T-box" as used herein refers to the family refers to the family of transcription factors that play roles throughout development. T-box genes are expressed in highly specific manners, and are involved in all of the major developmental signaling pathways. Common to all T-box proteins is a 180-200 amino acid DNA-binding motif, or T-box domain, which binds DNA in a sequence-specific manner (Papaioannou V E. Development. 2014 October; 141(20): 3819-33).

There are at least five subfamilies of T-box proteins: 1) the T subfamily, comprising T and Tbx19; 2) the Tbx1 subfamily, comprising Tbx1, Tbx10, Tbx15, Tbx18, Tbx20, and Tbx22; 3) the Tbx2 subfamily, comprising Tbx2, Tbx3, Tbx4, and Tbx5; 4) the Tbx6 subfamily, comprising Tbx6, Drtbx6, Drtbx16, and Mga; and 5) the Tbr1 subfamily, comprising Tbr1, Tbr2, and Tbx21 (Id.).

The term "tdTomato" as used herein refers to the tdTomato fluorescent protein, with an excitation maximum at 554 nm, and an emission maximum at 581 nm.

The term "transcription factor" as used herein refers to a protein that binds to and controls the activity of other genes.

The term "transgenic" as used herein refers to an organism that contains genetic material into which DNA from an unrelated organism has been artificially introduced.

The term "tumor suppressor gene" as used herein refers to a gene whose encoded protein directly or indirectly inhibits progression through the cell cycle and in which a loss-of-function mutation is oncogenic.

A "variant" of a gene or nucleic acid sequence is a sequence having at least 65% identity with the referenced gene or nucleic acid sequence, and can include one or more base deletions, additions, or substitutions with respect to the referenced sequence. The differences in the sequences may by the result of changes, either naturally or by design, in sequence or structure. Natural changes may arise during the course of normal replication or duplication in nature of the particular nucleic acid sequence. Designed changes may be specifically designed and introduced into the sequence for specific purposes. Such specific changes may be made in vitro using a variety of mutagenesis techniques. Such sequence variants generated specifically may be referred to as "mutants" of the original sequence.

A "variant" of a peptide or protein is a peptide or protein sequence that varies at one or more amino acid positions with respect to the reference peptide or protein. A variant can be a naturally-occurring variant or can be the result of spontaneous, induced, or genetically engineered mutation(s) to the nucleic acid molecule encoding the variant peptide or protein. A variant peptide can also be a chemically synthesized variant.

A skilled artisan likewise can produce polypeptide variants having single or multiple amino acid substitutions, deletions, additions or replacements. These variants may include inter alia: (a) variants in which one or more amino acid residues are substituted with conservative or non-conservative amino acids; (b) variants in which one or more amino acids are added; (c) variants in which at least one amino acid includes a substituent group; (d) variants in which amino acid residues from one species are substituted for the corresponding residue in another species, either at conserved or non-conserved positions; and (d) variants in which a target protein is fused with another peptide or polypeptide such as a fusion partner, a protein tag or other chemical moiety, that may confer useful properties to the target protein, such as, for example, an epitope for an antibody. The techniques for obtaining such variants, including genetic (suppressions, deletions, mutations, etc), chemical, and enzymatic techniques are known to the skilled artisan. As used herein, the term "mutation" refers to a change of the DNA sequence within a gene or chromosome of an organism resulting in the creation of a new character or trait not found in the parental type, or the process by which such a change occurs in a chromosome, either through an alteration in the nucleotide sequence of the DNA coding for a gene or through a change in the physical arrangement of a chromosome. Three mechanisms of mutation include substitution (exchange of one base pair for another), addition (the insertion of one or more bases into a sequence), and deletion (loss of one or more base pairs).

The term "von Willebrand factor" (vWF) as used herein refers to a glycoprotein produced uniquely by endothelial cells. Among other process, vWF is involved in the coagulation process. This glycoprotein is used as an endothelial cell marker.

The term "XFP" as used herein refers to a general acronym for fluorescent proteins, wherein the "X" is one letter stating the color of the emission.

The term "YFP" as used herein refers to red fluorescent protein, which can be excited by the 514 nm laser line and is optimally detected at 527 nm.

According to one aspect, the described invention provides a method for reducing progression of lung fibrosis after a lung injury comprising administering a therapeutic amount of a therapeutic agent, wherein the therapeutic amount is effective (i) to modulate expression of a T-box transcription factor in a population of cells in lung; and (ii). to reduce proliferation of the population of cells in lung expressing the T-box transcription factor.

According to some embodiments, the T box transcription factor is a Tbox 2 transcription factor.

According to some embodiments, therein the Tbox 2 transcription factor is T-box protein 4 (Tbx4).

According to some embodiments, the therapeutic agent is a small molecule inhibitor, a peptide inhibitor or a nucleic acid inhibitor.

According to some embodiments, the therapeutic agent is a peptide inhibitor. Exemplary peptide inhibitors include peptides that are effective to target one or more domains of Tbx-4. According to some embodiments, the peptide inhibitor comprises a nuclear localization signal peptide.

According to some embodiments, the therapeutic agent is a nucleic acid inhibitor. According to some embodiments, the nucleic acid inhibitor is one or more of a siRNA, a DNAzyme, an antisense oligonucleotide, an aptamer or an oligodeoxynucleotide decoy.

According to some embodiments, the nucleic acid inhibitor is a siRNA. According to some embodiments, the siRNA can be modified to increase stability of the RNA. According to some embodiments, the siRNA is an LNA™-modified siRNA to increase its thermal stability. According to some embodiments, the siRNA is 2'O-methyl modified to improve its stability. According to some embodiments, the therapeutic agent is a siRNA of amino acid sequence 5'-rGrCrAr-CrUrGrCrArArArGrArArArCrArUrGrGrArArArGGT-3' (SEQ ID NO: 1). According to some embodiments, the therapeutic agent is a siRNA of amino acid sequence 5'-rU-rGrCrArArUrUrArUrCrUrArArGrArArGrUrGrArCrU-rUTG-3' (SEQ ID NO: 2). According to some embodiments, knockdown of Tbx4 with the siRNA is effective to reduce invasiveness of the myofibroblasts.

According to some embodiments, the nucleic acid inhibitor is a DNAzyme that is effective to cleave and inactivate TBX4 mRNA. Generally, DNAzymes are catalytically active DNA molecules (see, e.g., Sterna Biologicals, GmbH & Co. KG, www.sterna-biologicals.com). DNAzymes of the so-called 10-23 family are specifically characterized by their capability to cleave RNA molecules after appropriate binding. Thus, they directly exert RNA endonuclease activity. 10-23 DNAzymes are single-stranded DNA molecules that consist of two binding domains flanking a central catalytic domain. The latter is composed of 15 deoxynucleotides, the sequence of which is conserved throughout all molecules within this specific DNAzyme class. In contrast, the binding domains are variable and are designed to specifically bind the corresponding target mRNA of interest by Watson-Crick base-pairing.

After binding of a DNAzyme to the corresponding sequence in the target mRNA via the binding domains (step 1), the catalytic domain becomes active and directly cleaves the target mRNA molecule (step 2). After successful cleavage of a target mRNA molecule, the DNAzyme-RNA-complex dissociates and the RNA cleavage products are further degraded by endogenous, intracellular enzymes. The DNAzyme molecule is then available for subsequent binding and cleavage of additional mRNA molecules (step 3).

According to some embodiments, the DNAzyme is modified with a 3'-3' inverted nucleotide at the 3' terminus to prevent exonuclease degradation.

According to some embodiments, the nucleic acid inhibitor is an antisense oligonucleotide. An antisense oligonucleotide (ASO) is a short strand of deoxyribonucleotide analogue that hybridizes with the complementary mRNA in a sequence-specific manner via Watson-Crick base pairing. Formation of the ASO-mRNA heteroduplex either triggers RNase H activity, leading to mRNA degradation, induces translational arrest by steric hindrance of ribosomal activity, interferes with mRNA maturation by inhibiting splicing, or destabilizes pre-mRNA in the nucleus, resulting in downregulation of target protein expression. Chan, J H, Wong, L S, "Clin. Exp. Pharmacol. Physiol. 2006, 33 (5-6): 533-40. According to some embodiments, the antisense oligonucleotide is a DNA antisense oligonucleotide. According to some embodiments, the antisense oligonucleotide is an RNA antisense oligonucleotide. According to some embodiments, the RNA antisense oligonucleotide is phosphorothioate modified to increase its stability and half-life.

According to some embodiments, the nucleic acid inhibitor is an aptamer. Aptamers are a class of small nucleic acid ligands that are composed of RNA or single-stranded DNA oligonucleotides that have high specificity and affinity for their targets. Similar to antibodies, aptamers interact with their targets by recognizing a specific three-dimensional structure. Sun, H. et al., Molec. Therapy Nucleic Acids 2014, 3: e182; doi: 10.1038/mbna.2014.32. According to some embodiments the aptamer is modified with polyethylene glycol to increase its half-life.

According to some embodiment, the nucleic acid inhibitor is an oligodeoxynucleotide (ODN) decoy. A decoy oligonucleotide is a synthesized short DNA sequence that has the same sequence as that found on the portion of the promoter region of a gene where a transcription factor lands. Normally when a transcription factor lands on the promoter region of a gene, transcription of the gene is switched on leading to its expression. However, the decoy oligonucleotide acts as the promoter's "lure", binds with the specific transcription factor in the cell so that the transcription factor cannot land on the genome, and the gene expression is suppressed. According to some embodiments, the gene is TBX4.

According to some embodiments, the lung injury induces proliferation of cells expressing Tbx4 in lung.

According to some embodiments of the method, in (a) the modulating expression of a T-box transcription factor in a population of cells in lung is effective to reduce the proliferation of cells expressing Tbx4 following the injury.

According to some embodiments, the population of cells in lung in which Tbx4 is expressed is heterogeneous.

According to some embodiments, the population of cells in lung in which Tbx4 is expressed comprises one or more of a population of pericytes, a population of lipofibroblasts, a population of endothelial cells, or a population of myofibroblasts. According to some embodiments, the proliferating cells that express cells are characterized by expression of one or more markers selected from α-smooth muscle actin (αSMA), Col1a1, desmin, vimentin, NG2, and PDGFRB.

According to some embodiments, the population of myofibroblasts in lung expressing Tbx4 in lung also express αSMA.

According to some embodiments, the proliferating cells that express Tbx4 comprise a population of fibroblasts resident in the lung of the subject.

According to some embodiments, inhibition of expression of Tbx4 is effective to modulate expression of Has-2.

According to some embodiments, the therapeutic amount of the Tbx4 siRNA is effective to decrease TGFβ-induced release of hyaluronic acid (HA).

According to some embodiments, the therapeutic agent is effective to reduce symptoms of pulmonary fibrosis.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, exemplary methods and materials have been described. All publications mentioned herein are incorporated herein by reference to disclose and described the methods and/or materials in connection with which the publications are cited.

It must be noted that as used herein and in the appended claims, the singular forms "a", "and", and "the" include plural references unless the context clearly dictates otherwise.

The publications discussed herein are provided solely for their disclosure prior to the filing date of the present application and each is incorporated by reference in its entirety. Nothing herein is to be construed as an admission that the present invention is not entitled to antedate such publication by virtue of prior invention. Further, the dates of publication provided may be different from the actual publication dates which may need to be independently confirmed.

EXAMPLES

The following examples are put forth so as to provide those with ordinary skill in the art with a complete disclosure and description of how to make and use the described invention, and are not intended to limit the scope of what the inventors regards as their invention nor are they intended to represent that the experiments below are all or the only experiments performed. Efforts have been made to ensure accuracy with respect to numbers used (e.g., amounts, temperatures, etc.) but some experimental errors and deviation should be accounted for. Unless otherwise indicated, parts are by weight, molecular weight is weight average molecular weight, temperature is in degrees Centigrade, and pressure is at or near atmospheric.

All mouse studies were approved by the Institutional Animal Care and Use Committee at Cedars-Sinai Medical Center. Tbx4 lung enhancer-Cre transgenic mice (Tbx4$^{LME}$-Cre or Tbx4-Cre$^{Tg}$) and Tbx4$^{LME}$-CreER transgenic mice were recently described (Kumar et al. Science. 2014 Nov. 14; 346(6211): 1258810). Tbx4-Cre knockin (Tbx4-Cre$^{Ki}$) mice were reported (Naiche et al. Dev Dyn. 2011 October; 240(10): 2290-300). Tbx4-Cre Rosa26-tdTomato mouse lines were obtained by crossing Tbx4-Cre knock-in (Tbx4-Cre$^{Ki}$) mice or transgenic mice with lineage reporter Rosa26-tdTomato mice (Madisen et al. Nat Neurosci. 2010 January; 13(1): 133-40).

To obtain Tbx4-CreER Rosa26-tdTomato, Tbx4-CreER mice were crossed to Rosa26-tdTomato mice. Tbx4-CreER Confetti mice were obtained by crossing Tbx4-CreER mice with Rosa26-Confetti mice (Livet et al. Nature. 2007 Nov. 1; 450(7166): 56-62) (Jackson Labs). Triple heterozygous αSMA-GFP Tbx4-Cre Rosa26-tdTomato mice were created by crossing Tbx4-Cre Rosa26-tdTomato mice with αSMA-GFP (a.k.a. Acta2-GFP) mice (Condren et al. PLoS One. 2013; 8(1): e53386) (Robert N. Fariss, National Eye Institute). Triple heterozygous Tbx4-Cre Rosa26-tdTomato mice were bred with Col1a1-GFP mice (Iwaisako et al. Proc Natl Acad Sci USA. 2014 Aug. 12; 111(32): E3297-305) (David A. Brenner, University of California, San Diego) to generate COL1a1-GFP-Tbx4-Cre Rosa26-tdTomato mice. Tbx4-Cre Rosa26-tdTomato mice were bred with NG2-YFP mice (LeBleu et al. Nat Med. 2013 August; 19(8): 1047-53) (Raghu Kalluri, University of Texas MD Anderson Cancer Center) to create the Ng2-YFP Tbx4-Cre Rosa26-tdTomato triple heterozygous mice. Tbx4-CreER mice were bred with Rosa26-DTA mice (Voehringer et al. J Immunol. 2008 Apr. 1; 180(7): 4742-53) (Jackson Labs) to generate Tbx4-CreER Rosa26-DTA mice.

Tbx4$^{flox/flox}$ mice were described previously (Arora et al. PLoS Genet. 2012; 8(8): e1002866). αSMA-CreER mice (Wendling et al. Genesis. 2009 January; 47(1): 14-8) were crossed with Tbx4$^{flox/flox}$ mice to create the αSMA-CreER Tbx4$^{flox/flox}$ mice. Col1a2-CreER Tbx4$^{flox/flox}$ mice were generated by breeding Col1a2-CreER mice (Zheng et al. Am J Pathol. 2002 May; 160(5): 1609-17) (Jackson Labs) with Tbx4$^{flox/flox}$ mice. Conditional NG2 cell-specific Tbx4 knockout mice (Ng2-CreER Tbx4$^{flox/flox}$) were generated by breeding Ng2-CreER (a.k.a. Cspg4-CreER) mice (Zhu et al. Development. 2011 February; 138(4): 745-53) (Jackson Labs) with Tbx4$^{flox/flox}$ mice. Tamoxifen (Sigma-Aldrich) dissolved in corn oil was injected intraperitoneally (i.p.) at 1 to 5 doses of 10 µl/g or 20 µg/g body weight to induce Cre-mediated recombination. All mice were on a C57Bl/6 background.

Example 1: Identification of Fibroblast Origin

Murine Lung Fibrosis Model

To determine whether Tbx4+ cells expanded during injury, adult (8 to 16 weeks old) Tbx4-Cre$^{Tg}$;Rosa26-tdTomato and Tbx4-Cre$^{Ki}$;Rosa26-tdTomato mice (both male and female), were subjected to bleomycin induced lung injury (Li et al. J Exp Med. 2011 Jul. 4; 208(7): 1459-71; Lovgren et al. Sci Transl Med. 2011 Mar. 16; 3(74): 74ra23). Bleomycin at 2.5 U/Kg was injected intratracheally. Mouse lungs were harvested on day 14 or day 21 for examination via histology, hydroxyproline assay, and single cell isolation.

5-Bromo-2-Deoxyuridine (BrdU) Incorporation Assay

Cell proliferation was quantified by BrdU labeling. BrdU (5 mg/ml, Sigma B-9285) was injected intraperitoneally into bleomycin treated Tbx4-CreER; Rosa26-tdTomato mice at a dose of 10 µl/g body weight at day 21. After 3 h, lungs were collected and fixed by 10% formaldehyde. Lungs were embedded with O.C.T. compound (Sakura Finetek). Frozen sections were processed for antigen retrieval by applying 1.5 N HCl to the section for 30-45 min. The sections were subsequently processed for immunofluorescent staining with anti-BrdU antibody (1:250; Accurate Chemicals), followed by Alexa Fluor 488-conjugated secondary antibody (1:500; Invitrogen). The number of BrdU-positive cells was counted in 5 random fields under 60× magnification and the average number of labeled cells per field was calculated.

Scale Processing and Imaging

Tbx4-CreER Confetti mouse lungs were fixed with 10% formalin for 4-16 hrs and washing with PBS overnight. Tissue was transferred to Scale A2 (an aqueous solution used for making biological tissue samples transparent prepared by dissolving, in pure water, 4M urea, 0.1% (w/v) Triton X-100, and 10% w/v glycerol) and kept on a rocker at 4° C. for 1-2 weeks until maximal tissue clearing occurred. Whole-mount samples immersed in Scale A2 were imaged on the inverted Zeiss 780 confocal microscope in a 35-mm glass-bottom microwell dish with a 20× objective. Z-stack and tiled images were acquired from large areas and volumes of tissue. Images were processed by Zen software.

Histology, Immunofluorescence, and Confocal Imaging

Immunofluorescence staining on frozen sections (5 µm or 12 µm) was performed using primary antibodies to αSMA (A2547, Sigma), Desmin (RB9014-P0, Thermo Scientific), NG2 (AB5320, Millipore), Vimentin (sc-7557, Santa Cruz), Col1a1 (NB600-408, Novus Biologicals), PDGFRB (04-397, Millipore), von Willebrand factor (Ab6994, Abcam), lipid acid (a lipophilic stain used to identify lipofibroblasts; Vybrant® DiO Cell-Labeling Solution, v22886, Life Technology), surfactant protein C (SPC) (AB3786, Millipore), clara cell 10 protein (CC10) (Stripp lab), podoplanin (PDPN) (8.1.1-c, Developmental Studies Hybridoma Bank), secretoglobin family 1A member 1 (Scgb1a1) (Cedars-Sinai Medical Center, Los Angeles, Calif.), bromodeoxyuridine (BrdU) (OBT0030, Accurate Chemical and Scientific), biotinylated recombinant human aggrecan (staining for HA, custom order from R&D Systems Inc., lot PQP051505A) and associated Alexa Fluor 488 conjugated secondary antibodies (Life Technology). Paraffin lung sections were stained with RFP (600-401-379, Rockland). Stained sections were imaged using a Zeiss 780 reverse Laser Scanning Confocal Microscope (Zeiss). The following protocol was implemented:

Preparation of Slides and Samples:

For frozen sections, fresh tissue is snap frozen in liquid nitrogen or isopentane pre-cooled in liquid nitrogen, and stored at −80° C. Sections (4-8 µm thick) are cut and mounted on superfrost or gelatin coated slides. The slide can be stored at −80° C. until needed. Prior to fixation, the slides are warmed to room temperature for 30 minutes.

For paraffin-embedded sections, paraffin is removed from the sections via treatment in xylene for 2×5 minutes. The sections are hydrated with 100% ethanol for 2×3 minutes; with 95% ethanol for 1 minute; and rinsed in distilled water prior to fixation.

The samples are fixed either in ice-cold methanol, acetone (1-10 minutes) or in 3-4% paraformaldehyde in 0.01M phosphate-buffered saline (PBS), pH 7.4 for 15 minutes at room temperature, and washed twice with ice cold PBS.

If the target protein is expressed intracellularly, it is important to permeabilize the cells. Acetone fixed samples do not require permeabilization. The samples are incubated for 10 minutes with PBS containing 0.25% Triton X-100. For analysis of membrane-associated antigens, 100 μM digitonin or 0.5% saponin is used in place of Triton X-100. Cells are washed in PBS three times for 5 mins.

The cells are incubated with 1% bovine serum albumin (BSA) in PBS with 0.05% Tween-20 detergent (PBS-T) for 30 min to block nonspecific binding of the antibodies; alternative blocking solutions are 1% gelatin or 10% serum from the species in which the secondary antibody was raised, or other commercially available blocking solutions.

The cells are incubated with a primary incubation solution comprising one or a mixture of primary antibodies in 1% BSA in PBS-T in a humidified chamber for 1 hour at room temperature or overnight at 4° C. The primary incubation solution is decanted and the cells are washed three times with PBS (5 minutes per wash). The cells are incubated with a secondary incubation solution comprising associated Alexa Fluor 488 conjugated secondary antibodies (for frozen sections) or RFP (for paraffin lung sections) in 1% BSA for 1 hour at room temperature under dark conditions. The secondary incubation solution is decanted and the cells are washed three times with PBS (5 minutes per wash) in the dark.

For counter-staining, cells are incubated with: 0.1-1 μg/ml of counter stain for 1 min, and then rinsed with PBS. A coverslip is mounted with a drop of mounting medium, sealed with nail polish to prevent drying and movement under the microscope, and stored in the dark at −20° C. or 4° C.

The excitation and optimal detection wavelengths of the Alexa Fluor 488, RFP, and Vybrant Dyes are as follows:

| Dye | Excitation (nm) | Detection (nm) |
| --- | --- | --- |
| Alexa Fluor 488 | 488 | 519 |
| RFP | 488 or 532 | 588 |
| Vybrant DiO | 484 | 501 |

Hydroxyproline Assay

A hydroxyproline assay for quantitatively measuring hydroxyproline resulting from the hydrolysis of collagen in tissue and protein/peptide hydrolysates was used to measure collagen content in lung tissue from 7-17 mice per group. The ability of the assay to completely hydrolyze and recover hydroxyproline from collagen was confirmed using samples containing known amounts of purified collagen.

An exemplary hydroxyproline assay kit is available from Sigma-Aldrich (Cat. No. MAK008). Vials are briefly centrifuged before opening. To maintain reagent integrity, repeated freeze/thaw cycles are avoided. Oxidation buffer is allowed to come to room temperature before use. DMAB Concentrate is warmed to room temperature prior to use, and stored protected from light and moisture at 2-8° C.

All samples and standards are run in duplicate. Ultrapure water is used for the preparation of standards and samples.

10 μL of the 1 mg/mL Hydroxyproline Standard Solution is diluted with 90 mL of water to prepare a 0.1 mg/mL standard solution. 0, 2, 4, 6, 8, and 10 μL of the 0.1 mg/mL hydroxyproline standard solution is added into a 96 well plate, generating 0 (blank), 0.2, 0.4, 0.6, 0.8, and 1.0 μg/well standards. Because endogenous compounds may interfere with the reaction, a sample spiked with 0.4 μg of the hydroxyproline standard is included as a spiked sample control to ensure the accurate determination of Hydroxyproline in the test samples, 10 mg tissue or cells are homogenized in 100 μL of water and transferred to a container, e.g., a pressure-tight vial with PTFE-lined cap or to 2.0 mL polypropylene tube. 100 μL of concentrated hydrochloric acid (HCl, ~12 M) is added, the container is capped tightly, and hydrolysis allowed to take place at 120° C. for 3 hours. 10-50 μL of supernatant is transferred to a 96 well plate.

All wells are evaporated to dryness under vacuum or the plates are placed in a 60° C. oven to dry the samples.

Chloramine T/Oxidation Buffer Mixture and Diluted DMAB Reagent are stable for 2-3 hours after preparation, and should be prepared after sample preparation, just prior to the start of the assay.

100 μL Chloramine T/Oxidation Buffer Mixture is required for each reaction well. For each well, 6 μL of Chloramine T Concentrate is added to 94 μL of Oxidation Buffer and mix well.

100 μL Diluted DMAB Reagent is required for each reaction well. For each well, 50 μL of DMAB Concentrate is added to 50 μL of Perchloric Acid/Isopropanol Solution and mix well.

100 μL of the Chloramine T/Oxidation Buffer Mixture is added to each sample and standard well and incubated at room temperature for 5 minutes. 100 μL of the Diluted DMAB Reagent is added to each sample and standard well, and incubated for 90 minutes at 60° C. Absorbance at 560 nm (A560) is measured.

The background for the assay is the value obtained for the 0 (blank) hydroxyproline standard and is subtracted from all readings. A standard curve is plotted from the values obtained from the appropriate hydroxyproline standards. The amount of hydroxyproline present in the samples may be determined from the standard curve. The concentration of Hydroxyproline in a sample (C)=$S_a/S_v$, where $S_a$=Amount of hydroxyproline in unknown sample (μg) from standard curve; and $S_v$=Sample volume (μL) added into the wells. For spiked samples, any sample interference is corrected for by subtracting the sample reading from the spiked sample reading according to the following formula:

$$S_a = \frac{(A_{560})_{sample}}{(A_{560})_{spiked\ control} - (A_{560})_{sample}} \times 0.4\ \mu g$$

Fibroblast Isolation and Culture

Primary fibroblasts were derived from mouse lungs as described previously (Tager A M, et al. Am J Respir Cell Mol Biol. 2004 October; 31(4): 395-404). Briefly, lungs from unchallenged C57Bl/6 mice, and mice 5 and 14 d after bleomycin challenge, were digested for 45 min at 37° C. in Roswell Park Memorial Institute medium (RPMI) with 0.28 U/ml Liberase™ Research Grade (Roche, enzyme blend comprising collagenases I and II and thermolysin, for the dissociation of tissues) and 60 Um' DNase I, passed through a 70 μm filter, centrifuged at 540×g at 4° C., and plated in tissue culture flasks in Dulbecco's modified Eagle's medium (DMEM) with 15% fetal bovine serum (FBS); cells were passaged when subconfluent after harvest with trypsin-EDTA (Cellgro, Herndon, Va.) (Id.). The cells were used from three to six generations. Human lung fibroblasts were isolated from surgical lung biopsies or lung transplant explants obtained from patients with idiopathic pulmonary fibrosis (IPF) (Meltzer et al. BMC Med Genomics. 2011 Oct. 5; 4:70). Pathological confirmation was obtained for every case. IPF was confirmed by the identification of a usual interstitial pneumonia under the light microscope. Patient demographics were as follows: 2 females and 2 males; ages between 51 and 78 with median age 67; percentage forced vital capacity (FVC %) 51-78, median 57; and percentage diffusing capacity factor of the lung for carbon monoxide (DLCO %) 18-42, median 30.75. Samples of whole lung tissue were obtained at the time during orthotopic lung transplantation surgery. Samples were immediately processed following removal from the body. The specimens were cut into small pieces (~1 mm in diameter), and were cultured in DMEM supplemented with 15% FBS, 100 U/ml penicillin, 100 µg/ml streptomycin, 5 µg/ml gentamicin, and 0.25 µg/ml amphotericin B. The cells of passages 5-7 were used for invasion assays, siRNA interference assays, and HA amount measurements.

Matrigel Invasion Assay

The invasive behavior of Tbx4 positive and negative fibroblasts isolated from Tbx4-Cre Rosa26-tdTomato mouse lungs was performed essentially as described previously (Li et al. J Exp Med. 2011 Jul. 4; 208(7): 1459-71). Briefly, equal numbers of fibroblasts ($5 \times 10^4$) in 500 µl of 10% FBS complete medium were plated onto BioCoat Matrigel Invasion Chambers (Corning) containing polyethylene terephthalate (PET) filter-inserts containing 8 µm pores. 750 µl of 10% FBS complete medium with 10 ng/ml PDGF (R & D 120-HD-001) were added to the bottom of wells. After 24 hours of incubation in a $CO_2$ incubator, media were removed, and the filter inserts with the invaded cells washed once with PBS followed by fixing and staining with a Protocol Hema 3 stain set (Fisher Scientific). Matrigel matrix and non-invading cells on the upper surface of the filter were removed by wiping with a cotton swab; the filters were removed from the insert by a scalpel blade and mounted onto glass slides. The invading cells of each sample were counted in nine randomly selected fields of duplicate filters under a microscope at 400× magnification. Tbx4 siRNA effects on 3T3 cell line and human IPF lung fibroblast invasion were assessed using 30 nM of the siRNA shown in Table 1 below:

TABLE 1 siRNA Sequences

| Name | Sequence | SEQ ID No: |
|---|---|---|
| mTbx4 siRNA | 5'-rGrCrArCrUrGrCrCrArArGrArAr ArCrArUrGrArArArGGT-3' | 1 |
| hTbx4 siRNA | 5'-rUrGrCrArArUrUrArUrCrUrArAr GrArArGrUrGrArCrUrUTG-3' | 2 |

Trilencer-27 universal scrambled negative control siRNA duplex (SR30004, OriGene Technologies, Inc.) was used as a negative control. The cells were transfected with siRNAs for 48 hours before performing the invasion assay.

Mouse Embryonic Fibroblast (MEF) Isolation and Culture

Mouse embryonic fibroblast (MEF) cells were derived from E14 embryos of CMV-Cre Tbx4$^{f/w}$ or control (CMV-Cre only or Tbx4$^{f/w}$ only) mice as described previously (Jozefczuk J, Drews K, Adjaye J. Preparation of mouse embryonic fibroblast cells suitable for culturing human embryonic and induced pluripotent stem cells. J Vis Exp. 2012; (64):3854).

Briefly, mouse embryonic fibroblasts are isolated as follows. A pregnant mouse is sacrificed at 13 or 14 days post-coitum by cervical dislocation. The uterine horns are dissected out, briefly rinsed in 70% (v/v) ethanol, and placed into a falcon tube containing PBS without $Ca^{2+}Mg^{2+}$ (Gibco, Invitrogen). The uterine horns are placed into a Petri dish and each embryo separated from its placenta and embryonic sac. The head and red organs are dissected, washed in PBS and all embryos placed in a clean Petri dish. The tissue is finely minced using a sterile razor blade until it becomes possible to pipette, and 1 ml of 0.05% trypsin/EDTA (Gibco, Invitrogen), including 100 Kunitz units of DNase I (USB), is added per embryo. The tissue is transferred into a 50 ml falcon tube and incubated for 15 min at 37° C. After each 5 min of incubation, the cells are dissociated by pipetting up and down thoroughly. The trypsin is inactivated by adding about 1 volume of freshly prepared MEF medium containing 450 ml of DMEM, 50 ml of FBS (10% (v/v)), 5 ml of 200 mM L-glutamine (1/100 (v/v)), 5 ml of Penicillin-streptomycin (1/100 (v/v)). The cells are centrifuged at low-speed (300×g), 5 min, the supernatant carefully removed, and the cell pellet then resuspended in warm MEF medium.

A number of cells which is approximately equivalent to 3-4 embryos is plated in each T150 (TPP) flask coated with 0.2% gelatine (Gelatine from bovine skin, Type B, Sigma) for 2 hr. The fibroblasts (P0, passage 0) are the only cells that have the ability to attach to the gelatine-coated flasks. Ideally, cells are 80-90% confluent after 24 hr and at this stage a major part of P0 cells is frozen for future usage.

The remaining T150 flask(s) of P0 cells is expanded until passage 3(P3) or passage 4 (P4), inactivated and used as feeders to replate hESCs or to produce conditioned medium (CM) (Jozefczuk et al. J Vis Exp. 2012 Jun. 21; (68): 3854).

The cells were used from three to six generations. MEFs were treated with 5 ng/ml TGF-β1 overnight. RNA was isolated for RT-PCR and supernatant was collected for HA ELISA.

Flow Cytometry

Mouse lung or bone marrow was isolated from Tbx4-Cre Rosa26-tdTomato mice, αSMAGFP Tbx4-Cre Rosa26-tdTomato mice, Col1a1-GFP Tbx4LME-Cre Rosa26-tdTomato mice and NG2-YFP Tbx4LME-Cre Rosa26-tdTomato mice after perfusion. Single mouse lung cells were dissociated by using mouse lung dissociation kit and gentleMACS dissociator (Miltenyi Biotec). Single bone marrow cells from Tbx4-Cre;Rosa26-tdTomato mice were dissociated by using pipette, followed by red blood cell lysis. Cells were analyzed with Fortessa (BD Biosciences). Fluorescence intensity is expressed in arbitrary units on a logarithmic scale or on a linear scale for forward scatter.

Cultured passage 3 fibroblasts from non-treated Tbx4-Cre Rosa26-tdTomato mice were sorted for tdTomato positive and tdTomato negative cells with FACS Aria 3 (BD Biosciences) to 95-98% purity.

Quantitative Real-Time (RT PCR

Real-time RT-PCR was used to quantify the relative mRNA levels of HAS2 in CMV-Cre Tbx4$^{f/w}$ or control MEF cells with or without human recombinant TGF-β1 treatment using gene-specific primers. In brief, total RNA was purified using RNAqueous-4PCR kit (Life Technology) and was reversed to cDNA using High-Capacity cDNA Reverse Transcription Kit (Life Technology) according to the manufacturer's instructions. HAS2 gene levels in the resultant cDNAs were examined using the ABI 7500 Fast Detection system (Applied Biosystems) with SYBR green as fluorescent dye enabling real-time detection of PCR products according to the manufacturer's protocol (Power SYBR green PCR Master Mix; Applied Biosystems). The relative expression levels of the gene were determined against GAPDH levels in the samples. The RT-PCR primers in listed in Table 2 were used.

TABLE 2

RT-PCR Primers

| Name | Sequence | SEQ ID No: |
|---|---|---|
| Mouse HAS2 Forward (GenBank accession no. NM_008216) | 5'-ACGACGACCTTTACATGATGGA-3' | 3 |
| Mouse HAS2 Reverse | 5'-GATGTACGTGGCCGATTTGCT-3' | 4 |

TABLE 2-continued

RT-PCR Primers

| Name | Sequence | SEQ ID No: |
|---|---|---|
| Mouse Tbx4 Forward (GenBank accession no. NM_011536.2) | 5'-TCACTGGATGCGGCAGTTGGTCTCT-3' | 5 |
| Mouse Tbx4 Reverse | 5'-CACGTGGGTGCAAAAGGCTGTGTTT-3' | 6 |
| Mouse GAPDH Forward | 5'-ATCATCTCCGCCCCTTCTG-3' | 7 |
| Mouse GAPDH Reverse | 5'-GGTCATGAGCCCTTCCACAAC-3' | 8 |

Affymetrix cDNA Microarray

Cultured passage 3 fibroblasts from (untreated) Tbx4-Cre Rosa26-tdTomato mice were sorted for tdTomato positive and tdTomato negative cells with FACS Aria 3 (BD Biosciences) to 95-98% purity. Total RNA was assessed for quality with an Agilent 2100 Bioanalyzer G2939A (Agilent Technologies, Santa Clara, Calif.) and a Nanodrop 8000 spectrophotometer (Thermo Scientific/Nanodrop, Wilmington, Del.). Hybridization targets were prepared with the Ovation Pico WT Amp V2 kit (NuGen, San Carlos, Calif.) and the Encore Biotin Module (NuGen, San Carlos, Calif.) from total RNA, hybridized to GeneChip® Mouse 430 2.0 arrays in Affymetrix GeneChip® hybridization oven 645, washed in Affymetrix GeneChip® Fluidics Station 450 and scanned with Affymetrix GeneChip® Scanner 7G according to standard Affymetrix GeneChip® Hybridization, Wash, and Stain protocols. (Affymetrix, Santa Clara, Calif.).

Table 3 lists the necessary amount of cRNA required for the specific probe array format used.

TABLE 3

Hybridization Cocktail for Single Probe Arrays

| Component | 49 Format (Standard)/64 Format Array | 100 Format (Midi Array) | 169 Format (Mini) Array/ 400 Format (Micro) Array | Final Dilution |
|---|---|---|---|---|
| Fragmented and Labeled cRNA | 15 µg | 10 µg | 5 µg | 0.05 µg/µL |
| Control Oligonucleotide B2 (3 nM) | 5 µL | 3.3 µL | 1.7 µL | 50 pM |
| 20X Eukaryotic Hybridization Controls (bioB, bioC, bioD, cre) | 15 µL | 10 µL | 5 µL | 1.5, 5, 25, and 100 pM respectively |
| 2X Hybridization Mix | 150 µL | 100 µL | 50 µL | 1X |
| DMSO | 30 µL | 20 µL | 10 µL | 10% |
| Nuclease-free Water | to final volume of 300 µL | to final volume of 200 µL | to final volume of 100 µL | |
| Total Volume | 300 µL | 200 µL | 100 | |

For each target, the following are mixed, scaling up volumes if necessary for hybridization to multiple probe arrays. Probe arrays are equilibrated to room temperature immediately before use, the hybridization cocktail is heated to 99° C. for 5 minutes in a heat block, and the array is wet with an appropriate volume of Pre-Hybridization Mix by filling it through one of the septa. The probe array filled with Pre-Hybridization Mix is incubated at 45° C. for 10 minutes with rotation; the hybridization cocktail that has been heated at 99° C., is transferred, to a 45° C. heat block for 5 minutes; and the hybridization cocktail is spun at maximum speed in a microcentrifuge for 5 minutes to collect any insoluble material from the hybridization mixture.

The array is removed from the hybridization oven, vented with a clean pipette tip, and the Pre-Hybridization Mix extracted from the array with a micropipettor. The array is refilled with an appropriate volume of the clarified hybridization cocktail, avoiding any insoluble matter at the bottom of the tube. The probe array is placed into the hybridization oven, set to 45° C., rotated at 60 rpm, and allowed to hybridize for 16 hours.

After 16 hours of hybridization, the array is removed from the hybridization oven, vented by inserting a clean pipette tip into one of the septa, and the hybridization cocktail extracted with a pipettor through the remaining septum. The probe array is refilled completely with the appropriate volume of Wash Buffer A. The stain reagents are prepared, and the probe array washed and stained.

Data were background subtracted and normalized within the array using the LOESS normalization by Genespring GX 11 software.

Hyaluronan (HA) Quantification

The HA content of cultured media of human lung fibroblasts, of 3T3 cell lines, or in the bronchioalveolar lavage fluid from Col-Cre;Tbx4$^{f/f}$ mice was quantified using a Hyaluronan DuoSet ELISA (DY3614, R&D).

Capture Antibody was diluted to the working concentration in PBS without carrier protein. A 96-well microplate was coated with 100 µL per well of the diluted Capture Antibody, and the plate sealed and incubated overnight at room temperature. Each well was aspirated and washed with Wash Buffer; the process was repeated two times for a total of three washes. Each well was filled with Wash Buffer (400 µL) using a squirt bottle, manifold dispenser, or autowasher. After the last wash, any remaining Wash Buffer was removed by aspirating or by inverting the plate and blotting it against clean paper towels. Plates were blocked plates by adding 300 µL of Reagent Diluent to each well, and incubated at room temperature for a minimum of 1 hour, after which each well was aspirated and washed as above.

100 µL of sample or standards in Reagent Diluent, or an appropriate diluent was added per well; the plate was covered with an adhesive strip and incubated 2 hours at room temperature. Each well was aspirated and washed as above. 100 µL of the Detection Antibody, diluted in Reagent Diluent, was added to each well; the plate was covered with a new adhesive strip and incubated 2 hours at room temperature. Each well was aspirated and washed as above. 100 µL of the working dilution of Streptavidin-HRP was added to each well; the plate was covered and incubated for 20 minutes at room temperature. Each well was aspirated and washed as above. 100 µL of Substrate Solution was added to each well; the plate was incubated for 20 minutes at room temperature. 50 µL of Stop Solution was added to each well, and the plate gently tapped to ensure thorough mixing.

The optical density of each well was determined immediately, using a microplate reader set to 450 nm.

RNA Interference

Tbx4 siRNA effects on 3T3 cell line and human IPF lung fibroblasts HA production were assessed with siRNA specific to Tbx4 (mTbx4 siRNA: 5'-rGrCrArCrUrGrCrCrArA-rGrArArArCrArUrGrGrArArArGGT-3' (SEQ ID NO: 1), hTbx4 siRNA: 5'-rUrGrCrArArUrUrArUrCrUrArArGrA-rArGrUrGrArCrUrUTG-3' (SEQ ID NO: 2), and Universal scrambled negative control siRNA duplex, SR30004, OriGene Technologies). The cells were transfected with 30 nM siRNAs for 48 hrs, and then treated with 5 mg/ml TGF-β for overnight. The supernatants were collected thereafter for HA measurement. Invasion assays were performed using 48 hr transfected cells.

Promotor Luciferase Assay

A 2880 bp Has2 promoter luciferase reporter plasmid was provided by Dr. Chin Chiang (Liu et al. Dev Biol. 2013 Mar. 15; 375(2): 160-71) (Vanderbilt University Medical Center). The plasmid contains a sequence from −2326 to exon1 of Has2 in pGL3 Basic plasmid (Promega, WI). The 901 bp (Chromosome 15—NC_000081.6:-436 to exon 1) and 664 bp (−112 to exon 1) Has2 promoter luciferase reporter plasmid was generated by PCR and cloned upstream of pGL3 Basic plasmid. Primers listed in Table 4 were used. CMV promoter driven GFP-tagged Tbx4 expression plasmid is purchased from GeneCopoeia (Rockville, Md.).

TABLE 4

Primers for Luciferase Assay

| Name | Sequence | SEQ ID No: |
|---|---|---|
| Forward 1 | 5'-CAAGCTCGAGGGAATCCTTGTAACG-3' | 9 |
| Forward 2 | 5'-CCGCCTCGAGTCCCGCCCAGTCCCT-3' | 10 |
| Reverse | 5'-TGCCAAGCTTCTTGTTCAGCTCCTGCTCATAGA-3' | 11 |

Luciferase assays were performed essentially as previously (Liu et al., 2013), using the Promega Dual Luciferase Reporter (DLR™) assay system (Promega, WI). In brief, growth media was removed from cultured cells, the cells rinsed in 1×PBS, and all rinse solution removed. The recommended volume of 1×Passive Lysis Buffer (PLB) was dispensed into each culture vessel, which then was gently rocked/shaken for 15 minutes at room temperature. The lysate was transferred to a tube or vial. 100 µl of Luciferase Assay Reagent II (LAR II) was dispensed: into the appropriate number of luminometer tubes to complete the desired number of assays. Up to 20 µl of cell lysate was transferred into a sample tube containing LAR II; the sample was mixed by pipetting 2 or 3 times, and firefly luciferase activity measurement was recorded. 100 µl of Stop & Glo® Reagent was dispensed and the sample tube vortexed briefly to mix. Firefly luciferase activity measurement was recorded.

To determine the effect of Tbx4 on different length of the Has2 promoter activity, 293HEK cells co-transfected with Has2 promoter or pGL3 Basic plasmid and Tbx4 expressing plasmid for 48 hours prior to the luciferase assay. All reporter assays were normalized using *Renilla* luciferase as an internal control. Each data point represents the mean of triplicate wells with error bar representing the Standard Error of the Mean.

Calculation of the Internal Surface of a Lung

To ensure consistent and reproducible results, all (left and right) lungs were fixed by 10% formalin and with the same pressure, degassed, and embedded in OCT. Step sectioning was performed on each block of lung. For the slides of each step section, more than 5 lung images were sampled randomly under Zeiss AXIO microscopy (×10 objective). Lung morphometric analysis was performed on the images of the lung parenchymal area for uninjured and injured lung without severe fibrotic lesion. Mean linear intercept, also known as mean chord length (Campbell H, Tomkeieff S I. Calculation of the internal surface of a lung. *Nature.* 1952; 170(4316):116-117), was calculated by point and intersection counting using a grid line system (Foronjy R F, Mercer B A, Maxfield M W, Powell C A, D'Armiento J, Okada Y. Structural emphysema does not correlate with lung compliance: lessons from the mouse smoking model. Exp Lung Res. 2005; 31(6):547-562.).

Western Blot

To detect αSMA and p-actin expression, 25 µg of cell lysate was separated through 10% SDS-PAGE electrophoresis, blotted onto a nitrocellulose membrane (Life Technologies), and incubated with mAbs against αSMA (1:1,000; F3777, Sigma Chemical Co.) and p-actin (1:1,000;

12620, Cell Signaling Technology). The bands were visualized using the ECL system (Bio-Rad).

Collagen 1a1 ELISA

The collagen 1a1 content in cultured media of human lung fibroblasts was quantified using a collagen 1a1 direct ELISA. A standard curve for the assay was generated using collagen type I solution (C3867, Sigma-Aldrich) and collagen 1a1 antibody (ab21286, Abcam). The concentration of the collagen 1a1 in the cell supernatants was determined by extrapolation from the standard curve.

Caspase-3 Activity Assay

IPF fibroblasts were cultured on 96-well plates. Caspase-3 activity assay was performed 48 hours after Tbx4 siRNA transfection. The amount of protein in cell lysates was determined using a BCA protein assay kit (Pierce Chemical Co.). Caspase-3 activity was determined using a Caspase3/CPP32 Fluorometric Assay Kit (BioVision) according to manufacturer's protocol.

Calcein AM Cell Viability Assay

The viability of IPF fibroblasts 48 hours after Tbx4 siRNA transfection was analyzed by Calcein AM Cell Viability Assay Kit (Trevigen) according to manufacturer's protocol.

Statistics

Data are expressed as the mean±SEM. Differences in measured variables between experimental and control groups were assessed by Student's t tests (2-tailed) or Wilcoxon rank-sum test with nonparametric data. One-way ANOVA with Bonferroni test was used for multiple comparisons. The survival curves were compared using the log-rank test. Results were considered statistically significant at $P<0.05$. GraphPad Prism software was used for statistical analysis.

Results

Tbx4+ Cells Give Rise to Fibroblasts, Smooth Muscle, and Some Endothelial Cells in the Lung To label Tbx4+ cells in the lung, the Tbx4 lung enhancer-Cre transgenic mice (Tbx4$^{LME}$-Cre or Tbx4-Cre$^{Tg}$) and Tbx4-Cre knock-in mice (Tbx4-Cre$^{Ki}$) were respectively crossed with Rosa26-stop-tdTomato reporter mice to permanently mark any cells that previously or currently express Tbx4. At embryonic (E) day 15.5 and 8 weeks after birth, the fidelity of the genetic system was assessed in the lungs of both Tbx4-Cre$^{Tg}$;Rosa26-tdTomato and Tbx4-Cre$^{Ki}$ Rosa26-tdTomato mice.

Figure 8:
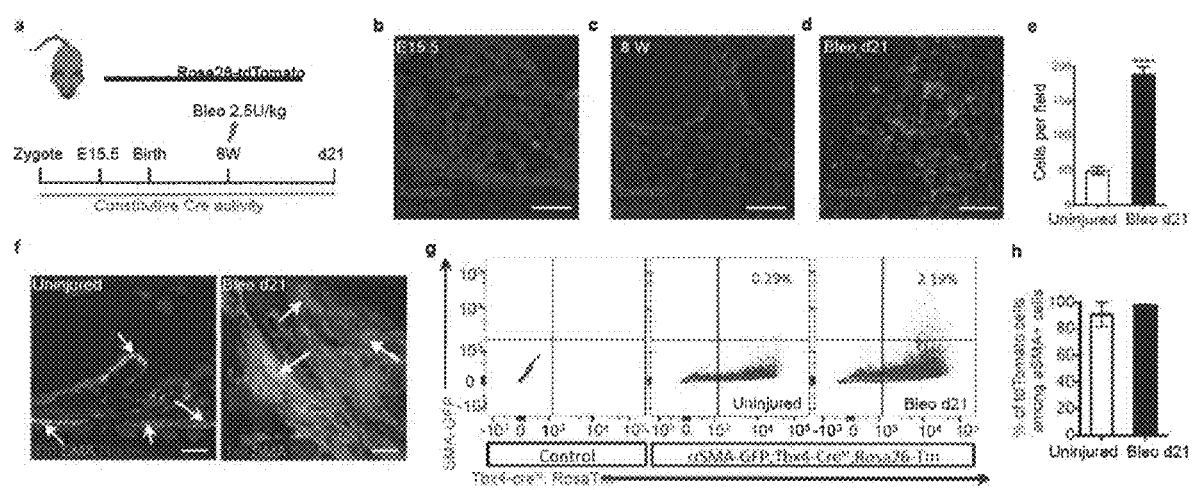
FIG. 8 shows that Tbx lineage cells are the major source of αSMA+ myofibroblasts. (a) Shows a schematic depicting lineage analysis methodology. Tbx4-Cre$^{tg}$; Rosa26-Tm or Tbx4-Cre$^{ki}$;rosa26-Tm mice were used for all experiments in FIG. 8. (b)-(d) Show representative histological sections of mouse lungs at embryonic stage (E15.5) (panel b), uninjured adult stage (8W) (panel c), and bleomycin treated D21 (panel d) adult Tbx4-Cre Rosa26-Tm, with Tbx4 lineage cells in red, and nuclei in blue (scale bar 100 μm). (e) Shows quantification of Tbx4 lineage tracing, expressed as cells counted in b (n=9 in each group of Tbx4-Cre$^{tg}$; Rosa26Tm mice.****p<0.001 by t test; mean±SEM). (f) Shows representative immunofluorescent images of lung histological sections of adult Tbx4-Cre$^{tg}$;Rosa26-Tm mice from uninjured or bleomycin treated d21 stained with αSMA antibody. Arrows show cells with overlaps in staining (n=9 lungs examined; scale bar: 10 μm). (g) Shows representative FACS plots of mouse lung single cells isolated from uninjured or bleomycin treated d21 αSMA-GFP; Tbx4-Cre$^{ki}$;Rosa26-Tm mice. (h) Shows quantification of tdTomato+ cells among αSMA-GFP+ cells in g (n=3 mice analyzed, mean±SEM).
Figure 22:
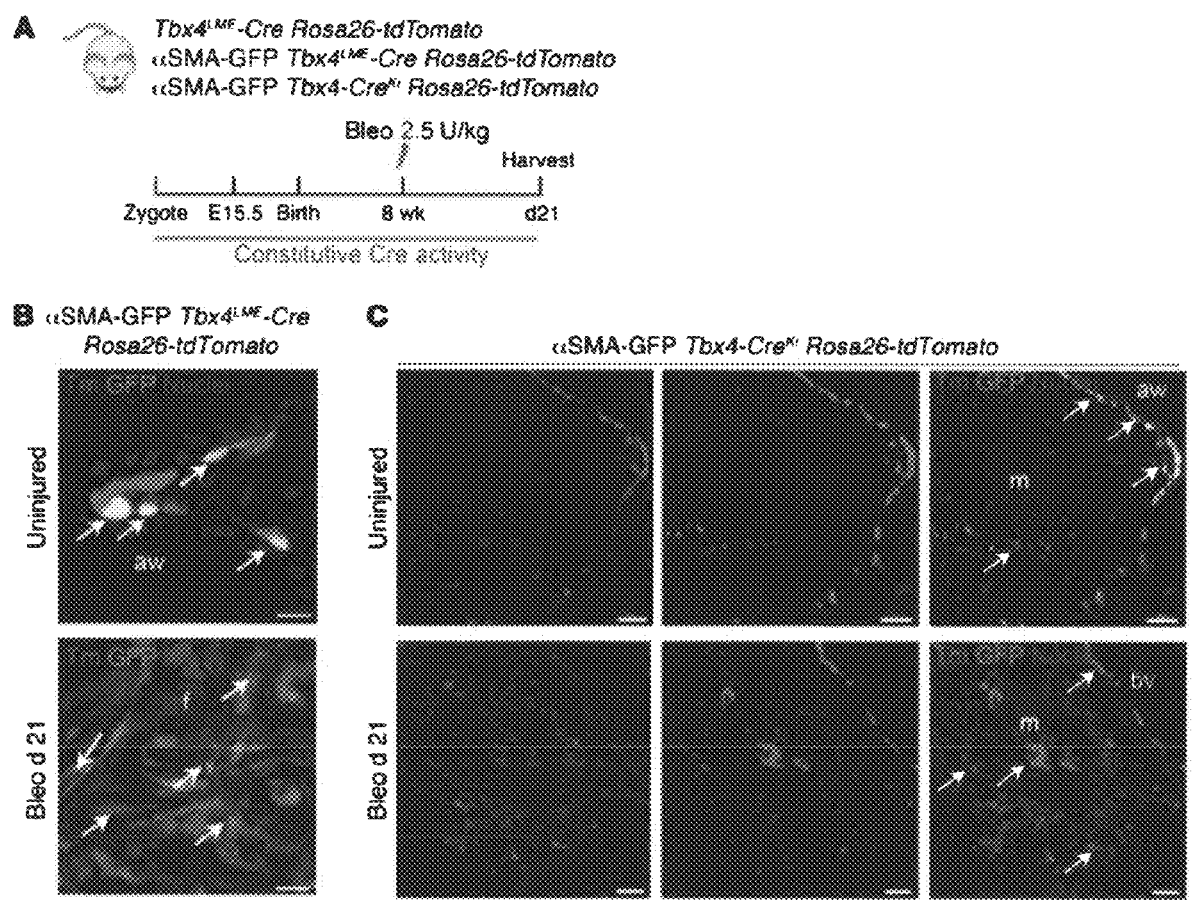
FIG. 22 shows that Tbx4-lineage cells in the lung are the major source of myofibroblasts. Tbx4-Cre$^{LME}$ Rosa26-tdTomato, αSMA-GFP Tbx4$^{LME}$-Cre Rosa26-tdTomato and αSMA-GFP Tbx4-Cre$^{Ki}$ Rosa26-tdTomato mice were used for all experiments in this figure. (a) Shows a schematic depicting lineage analysis methodology. (b) Shows representative histology images of uninjured or bleomycin-treated (d21) adult αSMA-GFP Tbx4$^{LME}$-Cre Rosa26-tdTomato mouse lung. (c) Shows representative histology images of uninjured or bleomycin-treated (d21) adult αSMA-GFP Tbx4-Cre$^{Ki}$ Rosa26-tdTomato mouse lung.

FIGS. 8 and 22 show that Tbx lineage cells are the major source of αSMA+ myofibroblasts. FIG. 8 (a) shows a schematic depicting lineage analysis methodology. Tbx4-Cre$^{tg}$;Rosa26-Tm or Tbx4-Cre$^{ki}$;rosa26-Tm mice were used for all experiments in FIG. 8. FIG. 8 panels (b)-(d) show representative histological sections of mouse lungs at embryonic stage (E15.5) (panel b), uninjured adult stage (8W) (panel c), and bleomycin treated D21 (panel d) adult Tbx4-Cre;Rosa26-Tm, with Tbx4 lineage cells in red, and nuclei in blue (scale bar 100 μm). FIG. 8 (e) shows quantification of Tbx4 lineage tracing, expressed as cells counted in b (n=9 in each group of Tbx4-Cre$^{tg}$;Rosa26Tm mice.****$p<0.001$ by t test; mean±SEM. FIG. 8 (f) shows representative immunofluorescent images of lung histological sections of adult Tbx4-Cre$^{tg}$; Rosa26-Tm mice from uninjured or bleomycin treated d21 stained with αSMA antibody. Arrows show cells with overlaps in staining (n=9 lungs examined; scale bar: 10 μm). FIG. 8 (g) shows representative FACS plots of mouse lung single cells isolated from uninjured or bleomycin treated d21 αSMA-GFP; Tbx4-Cre$^{ki}$;Rosa26-Tm mice. FIG. 8 (h) shows quantification of tdTomato+ cells among αSMA-GFP+ cells in g (n=3 mice analyzed, mean±SEM). FIG. 22 (a) shows a schematic depicting lineage analysis methodology. Tbx4-Cre$^{LME}$ Rosa26-tdTomato, αSMA-GFP Tbx4$^{LME}$-Cre Rosa26-tdTomato and αSMA-GFP Tbx4-Cre$^{Ki}$ Rosa26-tdTomato mice were used for all experiments in FIG. 22. FIG. 22 (b) shows representative histology images of uninjured or bleomycin-treated (d21) adult αSMA-GFP Tbx4$^{LME}$-Cre Rosa26-tdTomato mouse lung. FIG. 22 (c) shows representative histology images of uninjured or bleomycin-treated (d21) adult αSMA-GFP Tbx4-Cre$^{Ki}$ Rosa26-tdTomato mouse lung.

The labeled Tbx4 lineage cells reside in blood vessels, underneath the bronchioles, and in interstitial mesenchyme at both the embryonic (E15.5) and adult stage (8W) (FIG. 8b-d). These results are consistent with the recent observations that Tbx4-Cre labels virtually all lung mesenchyme and its derivatives including undifferentiated mesenchyme, airway smooth muscle, vascular smooth muscle, and mesothelium (Kumar et al. Science. 2014 Nov. 14; 346(6211): 1258810; Zhang et al. BMC Biol. 2013 Nov. 13; 11: 111).

To determine whether Tbx4+ cells expanded during injury, adult (8-12 weeks old) Tbx4-Cre$^{Tg}$;Rosa26-tdTomato and Tbx4-Cre$^{Ki}$;Rosa26-tdTomato mice were intracheally administered with 2.5 U/kg bleomycin solution. The mouse lungs were examined 21 days after bleomycin injury (FIG. 8(a)). Extensive expansion of tdTomato+ cells were found on day 21 when compared with non-treated lung (FIG. 8d, 8e). The tdTomato cellular labeling was identical in the lungs of both types of mice.

In order to address which subpopulations of cell types the Tbx4+ cells represent, immunofluorescence and confocal microscopy were used to localize stromal markers in the lungs of both Tbx4-Cre$^{Tg}$;Rosa26-tdTomato and Tbx4-Cre$^{Ki}$ Rosa26-tdTomato mice.

Figure 12:
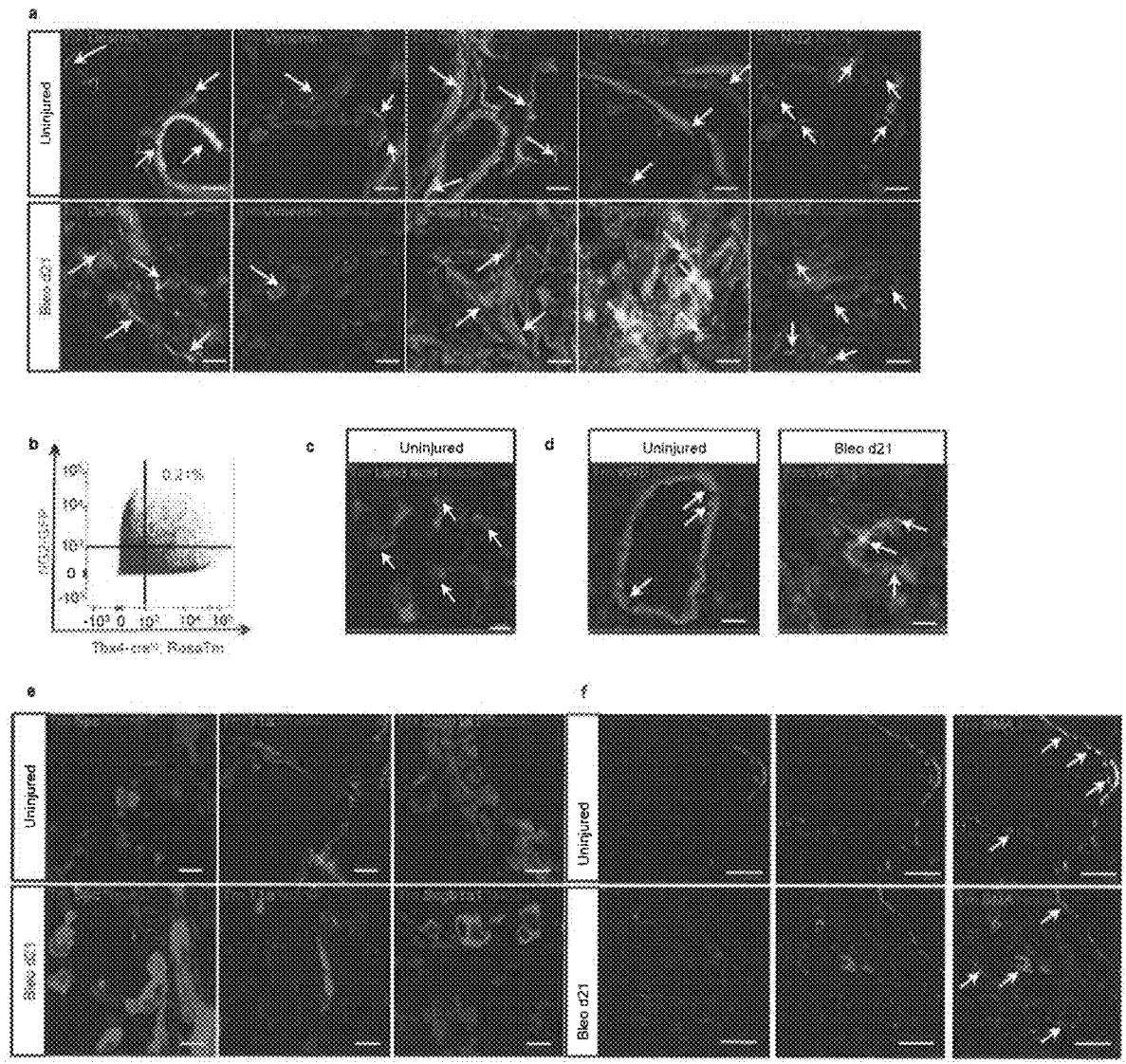
FIG. 12 shows that Tbx4 lineage cells give rise to fibroblasts, smooth muscle and some endothelial cells in the lung. (a), Tbx4-Cre$^{Tg}$ Rosa26-Tm adult mice at 8-12 weeks of age were challenged with bleomycin. Representative immunofluorescent images of lung histological sections from uninjured or bleomycin treated (d21) antibody stained with (from left to right) Desmin, Vimentin, Col1a1, PDGFRβ, and NG2 are shown in FIG. 12(a). Arrows show cells with overlap in staining (n=9 lungs examined, scale bar: 10 μm). (b) Shows a representative FACS plot of mouse lung single cells isolated from bleomycin treated (d21) NG2-YFP;Tbx4-Cre$^{Ki}$;Rosa26-Tm mice. (c) Shows representative lipid acid immunofluorescent staining of lung histological sections from uninjured Tbx4-Cre$^{Tg}$;Rosa26-Tm adult mice at 8-12 weeks of age. Arrows show cells with overlap in staining (n=9 lungs examined, scale bar: 10 μm). (d) Shows representative vWF staining of lung histological sections from uninjured Tbx4-Cre$^{Tg}$;Rosa26-Tm adult mice at 8-12 weeks of age. Arrows show cells with overlap in staining (n=9 lungs examined, scale bar: 10 μm). (e) Shows representative immunofluorescent images of lung histological sections from uninjured or bleomycin treated (d21) Tbx4-Cre$^{Tg}$;Rosa26-Tm mice at 8-12 weeks of age stained with (from left to right) Spc, T1α, and Scgb1a1 (n=9 lungs examined, scale bar: 10 μm). (f) Shows representative immunofluorescent images of lung histological sections from uninjured or bleomycin treated d21 αSMA-GFP;Tbx4-Cre$^{Tg}$;Rosa26-Tm mice. Arrows show cells with overlap in staining (n=3 lungs examined, scale bars: 100 μm).

FIG. 12 shows that Tbx4 lineage cells give rise to fibroblasts, smooth muscle and some endothelial cells in the lung. In panel (a), Tbx4-CreTg Rosa26-Tm adult mice at 8-12 weeks of age were challenged with bleomycin. Representative immunofluorescent images of lung histological sections from uninjured or bleomycin treated (d21) antibody stained with (from left to right) Desmin, Vimentin, Col1a1, PDGFRB, and NG2 are shown in FIG. 12(a). Arrows show cells with overlap in staining (n=9 lungs examined, scale bar: 10 μm). (b) Shows a representative FACS plot of mouse lung single cells isolated from bleomycin treated (d21) NG2-YFP Tbx4-CreKi;Rosa26-Tm mice. (c) Shows representative lipid acid immunofluorescent staining of lung histological sections from uninjured Tbx4-CreTg Rosa26-Tm adult mice at 8-12 weeks of age. Arrows show cells with overlap in staining (n=9 lungs examined, scale bar: 10 μm). (d) Shows representative vWF staining of lung histological sections from uninjured Tbx4-CreTg;Rosa26-Tm adult mice at 8-12 weeks of age. Arrows show cells with overlap in staining (n=9 lungs examined, scale bar: 10 μm). (e) Shows representative immunofluorescent images of lung histological sections from uninjured or bleomycin treated (d21) Tbx4-CreTg;Rosa26-Tm mice at 8-12 weeks of age stained with (from left to right) Spc, T1a, and Scgb1a1 (n=9 lungs examined, scale bar: 10 μm). (f) Shows representative immunofluorescent images of lung histological sections from uninjured or bleomycin treated d21 αSMA-GFP; Tbx4-CreTg;Rosa26-Tm mice. Arrows show cells with overlap in staining (n=3 lungs examined, scale bars: 100 μm).

Antibody staining of the frozen sections of mouse lung revealed co-staining of the Tbx4 cells with several well-known stromal cell markers, including αSMA (FIG. 8O, collagen 1 (Col1a1), desmin, vimentin, and NG2 (FIG. 12).

Overlap of Tbx4+ labeling and αSMA staining can be easily seen in airway smooth muscle, vascular smooth muscle, and interstitial fibroblasts (FIG. 8f). Overlap of Tbx4+ labeling and staining of fibroblast markers (Col1a1, desmin, and vimentin) can also readily be identified, especially in the lungs 21 days post bleomycin injury (FIG. 12 a, b). The antibody staining results were similar in the lungs of both Tbx4-CreTg;Rosa26-tdTomato and Tbx4-CreKi;Rosa26-tdTomato mice.

To further confirm the antibody staining results, reporter mice were used including αSMA-GFP, Col1a1-GFP, and NG2-YFP mice, respectively, to cross with either Tbx4-Cre$^{Tg}$ Rosa26-tdTomato or Tbx4-Cre$^{Ki}$ Rosa26-tdTomato mice. In untreated SMA-GFP Tbx4-Cre$^{Ki}$;Rosa26-tdTomato triple heterozygous mice, 0.29% of total cells in lung single cell digests were αSMA+Tbx4+ double positive cells by flow cytometric analysis (FIG. 8(g)). The αSMA+Tbx4+ double positive cells increased to 2.19% in the lungs 21 days after bleomycin (FIG. 8 (g)). Within αSMA+ cells, Tbx4+ cells were around 90.6% in untreated mice, and increase to 97.6% in mice 21 days after bleomycin (FIG. 8(h)). The histology image of SMA-GFP;Tbx4-Cre$^{Ki}$;Rosa26-tdTomato mouse frozen section are consistent with the FACS results (FIG. 12(f)).

Figure 19:
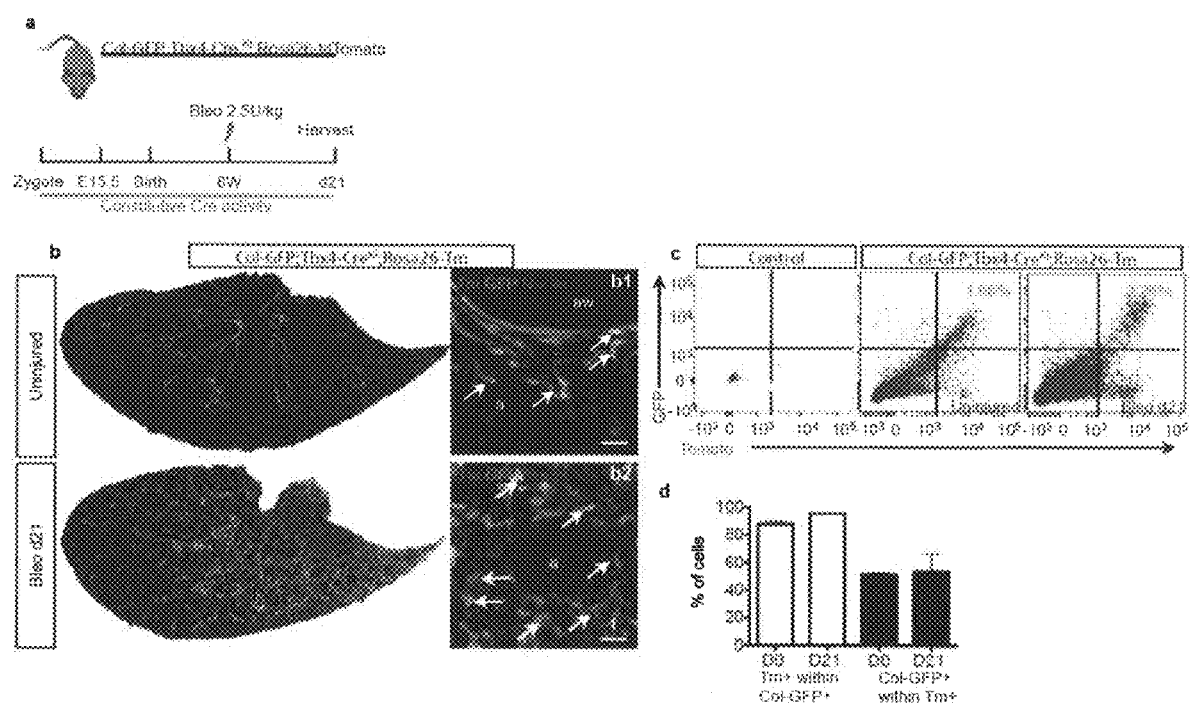
FIG. 19 shows that Tbx4 lineage cells in the lung are the major source of Col1a1+ fibroblasts. Col-GFP; Tbx4-Cre$^{Ki}$; Rosa26-Tm mice were used for all experiments in this figure. (a) Shows a schematic depicting the lineage analysis methodology. (b) Shows representative histology images of uninjured or bleomycin treated (d21) adult Col-GFP; Tbx4cre$^{Ki}$;Rosa26-Tm mouse lung. (c) Shows representative FACS plots of mouse lung single cells isolated from uninjured or bleomycin treated (d21) Col-GFP;Tbx4-Cre$^{ki}$; Rosa26-Tm mice. (d) Shows quantification of tdTomato_ cells among Col-GFP+ cells, and Col-GFP+ cells within tdTomato+ cells in panel b. Arrows show cells with overlaps. Scale bars, 10 μm (b1, b2); a=alveoli; aw=airway.

FIG. 19 shows that Tbx4 lineage cells in the lung are the major source of Col1a1+ fibroblasts. (a) Shows a schematic depicting the lineage analysis methodology. (b) Shows representative histology images of uninjured or bleomycin treated (d21) adult Col-GFP;Tbx4cre$^{Ki}$;Rosa26-Tm mouse lung. (c) Shows representative FACS plots of mouse lung single cells isolated from uninjured or bleomycin treated (d21) Col-GFP;Tbx4-Cre$^{Ki}$;Rosa26-Tm mice. (d) Shows quantification of tdTomato cells among Col-GFP+ cells, and Col-GFP+ cells within tdTomato+ cells in panel b. Arrows show cells with overlaps. Scale bars, 10 μm (b1, b2); a=alveoli; aw=airway. These data are consistent with a previous report that targeting TGF-β receptor II in resident collagen-expressing cells attenuated lung fibrosis (Hoyles et al. Am J Respir Crit Care Med. 2011 Jan. 15; 183(2): 249-6).

Pericytes have been implicated in tissue fibrosis and suggested to be a source of fibrotic fibroblasts (Humphreys et al., 2010; Hung et al., 2013; Lin et al., 2008). PDGFRB, chondroitin sulfate proteoglycan 4 (CSPG4, or NG2), along with FoxD1 and FoxJ1 have been used as pericyte markers [Hung et al. Am J Respir. Crit Care Med. 2013 Oct. 1; 188(7): 820-30; Rock et al. Proc Natl Acad Sci USA. 2011 Dec. 27; 108(52): E1475-83) REFS]. As shown in FIG. 12(a), some NG2+ cells are Tbx4+. In NG2-YFP;Tbx4-Cre$^{tg}$;Rosa26-tdTomato triple heterozygous mice 21 days after bleomycin, there was about 0.21% NG2+Tbx4+ cells within total cells in lung single cell digests (FIG. 12(b)). Within the NG2+ cells, about 15.22% were Tbx4+ cells (FIG. 12(b)). In Ng2-YFP Tbx4-Cre$^{Ki}$ Rosa26-tdTomato triple-heterozygous mice, there were 0.40% and 0.88% NG2/tdT double-positive cells within total cells in uninjured and bleomycin-injured (day 21) lung single-cell homogenates, respectively. A few NG2+ cells are of Tbx4 lineage in both bleomycin-injured (22%) and uninjured (10%) Ng2-YFP Tbx4-Cre$^{Ki}$ Rosa26-tdTomato mouse lungs (FIG. 22 (c)). Within tdT+ cells (progeny of TDX4 cells), 10% were NG2+ in both uninjured and bleomycin-injured lungs (data not shown).

Considering that the majority of αSMA+ cells are Tbx4+ cells, NG2+ cells may represent only a small population of αSMA+ cells, which is consistent with previous studies using NG2-CreER mice, showing that NG2 positive cells do not express high levels of αSMA in fibrotic lungs (Rock et al. Proc Natl Acad Sci USA. 2011 Dec. 27; 108(52): E1475-83). Recent research does not support NG2 as a reliable marker for all pericytes (Duffield. J Clin. Invest. 2014 June; 124(6): 2299-306; Hung et al. Am J Respir. Crit Care Med. 2013 Oct. 1; 188(7): 820-30; LeBleu et al. Nat Med. 2013 August; 19(8): 1047-53). Antibody staining with PDGFRB, another pericyte marker, exhibited much more co-localization than NG2 staining in Tbx4+ cells (FIG. 12(a)). This is consistent with a recent report that in fibrotic liver, immunostaining results showed that virtually all of αSMA positive cells were PDGFRB lineage cells. Desmin antibody staining in PDGFRB knock-in eGFP reporter mice was observed in virtually all eGFP expressing cells. In bleomycin injured mT/mG;PDGFRB-Cre mice, most PDGFRB lineage cells express αSMA (Henderson et al. Nat Med. 2013 December; 19(12): 1617-24). Therefore, staining with anti-PDGFRB antibodies may show more pericytes than NG2 staining.

It was recently reported that lipofibroblasts may contribute to a stem cell niche in the murine lung (Barkauskas et al. J Clin Invest. 2013 July; 123(7): 3025-36). To determine whether Tbx4 contributed to lipofibroblasts, Tbx4-Cre$^{tg}$;Rosa26-tdTomato lung sections were stained by Vybrant DiO staining. It was found that some Tbx4+ cells were identified as lipofibroblasts.

A minor population of Tbx4+ cells staining positive for von Willebrand factor (vWF) were found in both injured and normal adult mouse lung (FIG. 8(d)). Since some Tbx4+ cells can be identified as endothelial cells by von Willebrand factor staining, this result indicates that Tbx4+ cells may contain some endothelial cells. This finding is consistent with a previous report using platelet endothelial cell adhesion molecule (PECAM) immunostaining in embryonic mouse lungs (Zhang et al. BMC Biol. 2013 Nov. 13; 11: 111). However, an increase of the double positive (Tbx4+, vWF+) cells was not observed during fibrogenesis, implying that the endothelial cells are not contributing much, if at all, to fibrotic fibroblasts.

Figure 15:
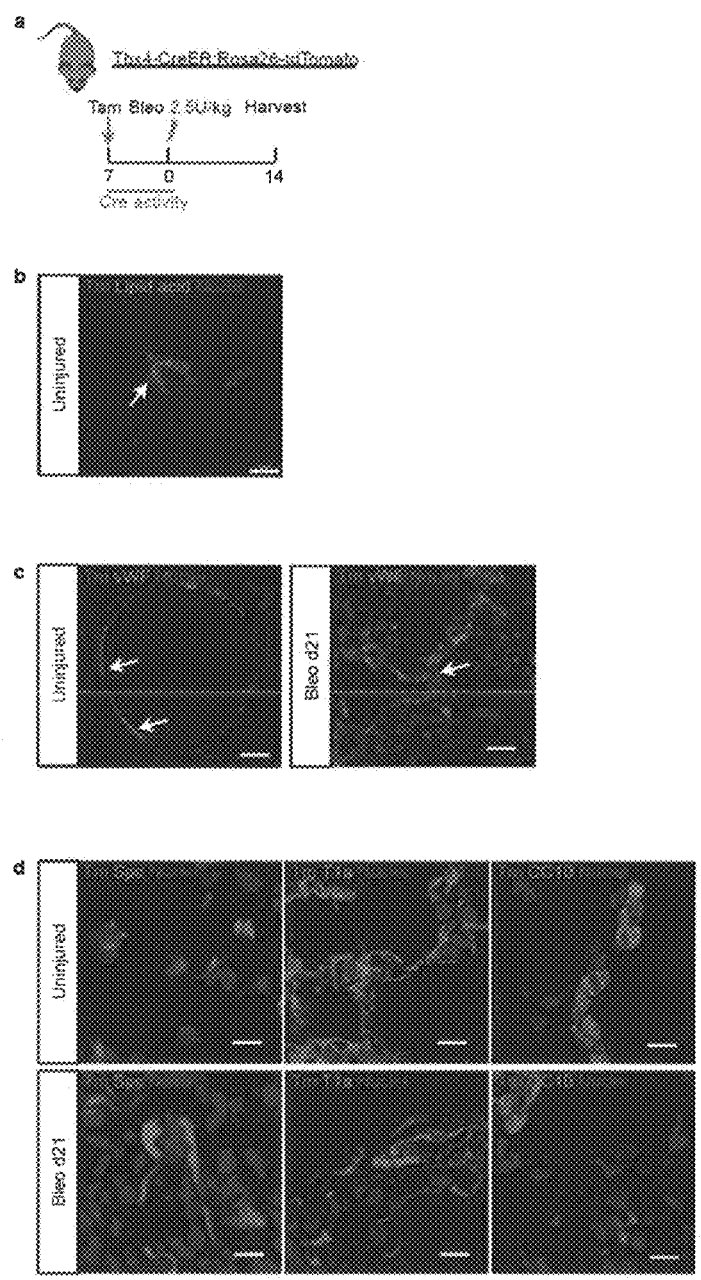
FIG. 15 shows that adult Tbx4+ cells include lipofibroblasts and endothelial cells but not epithelial cells. The experimental scheme is shown in (a) Tbx4-CreER;Rosa26-Tm mice were injected with 1 dose of tamoxifen, followed with bleomycin injury, and lungs were harvested on d14. (b) Shows a representative histological section stained for lipid acid (n=6 lungs examined, scale bar: 5 μm). (c) Shows a representative histological section stained with von Willebrand Factor (vWF) (n=6 lungs examined, scale bar: 10 μm). (d) Shows a representative histological section stained with (from left to right) Spc, T1a, and CC10, (n=6 lungs examined, scale bar: 10 μm).

FIG. 15 shows that adult Tbx4+ cells include lipofibroblasts and endothelial cells but not epithelial cells. The experimental scheme is shown in panel (a) Tbx4-CreER; Rosa26-Tm mice were injected with 1 dose of tamoxifen, followed with bleomycin injury, and lungs were harvested on d14. Panel (b) shows a representative histological section stained for lipid acid (n=6 lungs examined, scale bar: 5 μm). Panel (c) shows a representative histological section stained with von Willebrand Factor (vWF) (n=6 lungs examined, scale bar: 10 μm). Panel (d) shows a representative histological section stained with CC10, SPC, and T1a (n=6 lungs examined, scale bar: 10 μm).

Tbx4+ lineage cells did not contain any epithelial cells, since Tbx4+ cells had no overlap with any lung epithelial cell markers including AEC2 marker surfactant protein C (SFTPC or SPC), AEC1 marker podoplanin (PDPN; or T1a), and club cell marker CC10 (FIG. 12(e)). No Tbx4+ cells were found to co-express E-cadherin (data not shown). This is in tune with studies in embryonic lungs (Kumar et al. Science. 2014 Nov. 14; 346(6211): 1258810; Naiche et al. Dev Dyn. 2011 October; 240(10): 2290-300). Since Tbx4+ cells are the origin of fibrotic fibroblasts, the possibility that epithelial cells become any fibrotic fibroblasts is unlikely.

Tbx4+ cells, if any, were rare in extrapulmonary locations in both strains of mice (Tbx4-Cre$^{Tg}$;Rosa26-tdTomato and Tbx4-Cre$^{Ki}$;Rosa26-tdTomato). In bone marrow, a small portion (less than 0.03%) of total live cells showing tdTomato color was found in Tbx4-Cre$^{Ki}$;Rosa26-tdTomato mice, while none were observed in Tbx4-Cre$^{Tg}$;Rosa26-tdTomato mice (FIG. 13(a)).

Figure 13:
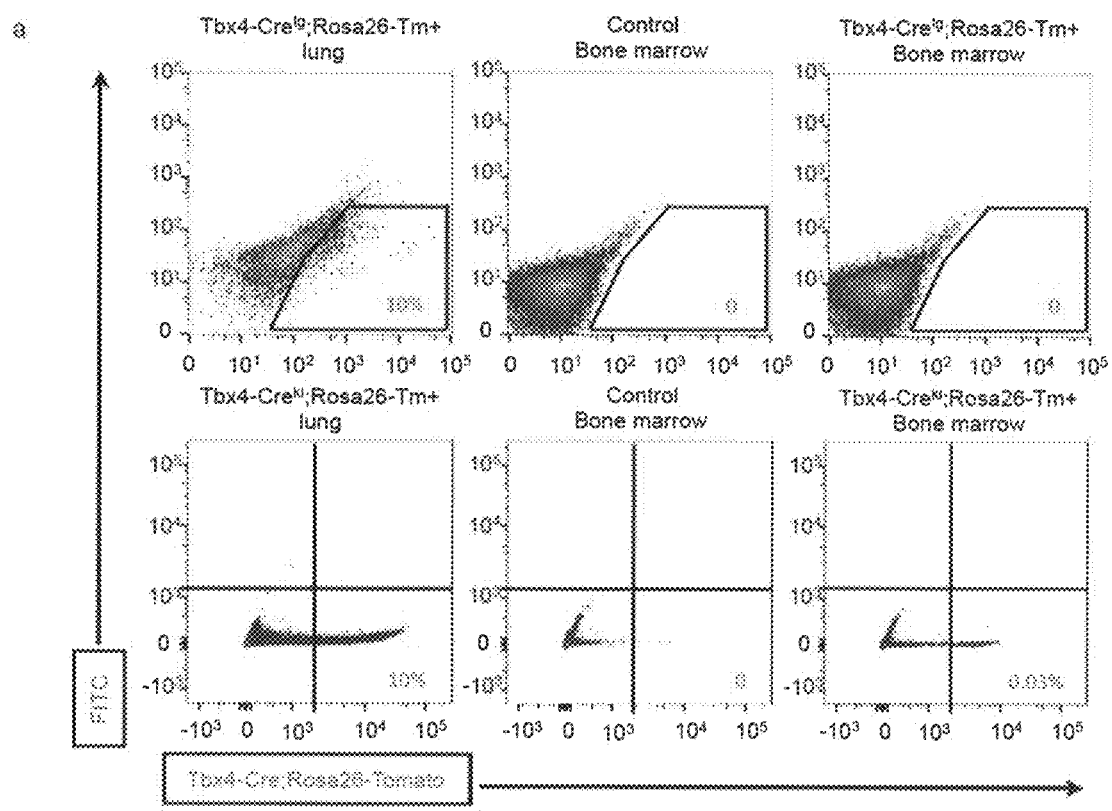
FIG. 13 shows Tbx4 lineage in bone marrow (a) FACS analysis of bone marrow and lung single cells from Tbx4-Cretg;Rosa26-Tm or Tbx4-Creki;Rosa26-Tm mice. There are around 10% of Tbx4+ cells within the lung single cells from Tbx4-Cretg;Rosa26-Tm or Tbx4-Creki;Rosa26-Tm mice. Bone marrow from Tbx4− Cretg;Rosa26-Tm and control mice shows no labeling of tdTomato, while bone marrow from Tbx4creki;Rosa26-Tm mice includes very small amounts (around 0.03%) of tdTomato labeled cells compared with control mice.

FIG. 13 shows Tbx4 lineage in bone marrow (a) FACS analysis of bone marrow and lung single cells from Tbx4-Cretg;Rosa26-Tm or Tbx4-Creki;Rosa26-Tm mice. There is around 10% of Tbx4+ cells within the lung single cells from Tbx4− Cretg;Rosa26-Tm or Tbx4-Creki;Rosa26-Tm mice. Bone marrow from Tbx4− Cretg;Rosa26-Tm and control mice show no labeling of tdTomato, while bone marrow from Tbx4creki;Rosa26-Tm mice included very small amounts (around 0.03%) of tdTomato labeled cells compared with control mice.

Other organs such as hearts, livers, kidneys, spleens, and intestines of normal 8 week old Tbx4cre$^{Ki}$;Rosa26-tdTomato mice also were examined, but none had any tdTomato cellular labeling (data not shown).

Together, these data indicate that Tbx4+ cells are heterogeneous cell types including smooth muscle cells, and fibroblasts, as well as some pericytes and endothelial cells. Tbx4+ fibroblasts are expanded during pulmonary fibrosis, and the majority of αSMA+ myofibroblasts are Tbx4+ cells.

Tbx4+ Cells were Proliferative and Induced De Novo Upon Bleomycin Injury in the Lung To address the question of the source of the expanded Tbx4+ cells, and whether Tbx4+ cells labeled prior to or after injury contribute to the expansion of Tbx4+ cells, tamoxifen induced cell fate mapping experiments were carried out. Tbx4-CreER transgenic mice (Kumar, M E et al, 2014, Science 346: 1258810) were bred with Rosa26-tdTomato mice. In these double transgenic mice, tdTomato labeling of the Tbx4+ cells is controlled in time by the administration of tamoxifen, which activates Cre, allowing for the distinct fate mapping of adult Tbx4+ cells, as well as of injury-induced Tbx4+ cells (FIG. 9a, f).

Figure 9:
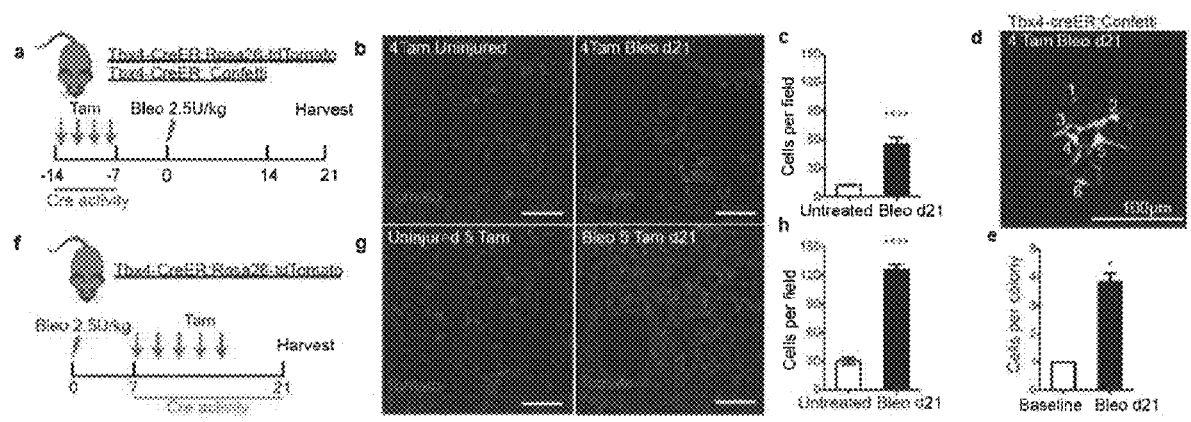
FIG. 9 shows that Tbx cells proliferate and are induced de novo upon bleomycin injury in the lung. Tbx4-CreER; Rosa26-Tm and Tbx4-CreER;Confetti were used for all experiments in this figure (a) Shows the experimental design for inducible Tbx4 cell labeling using tamoxifen one week before bleomycin injury for Tbx4-CreER;Rosa26-Tm mice. Four doses of Tam (tamoxifen) were given to the mice every other day. Lungs were harvested on d21. (b) Shows representative lung sections from Tbx4-CreER;Rosa26-Tm mice in a showing Tbx4 lineage cells in red and nuclei in blue (Scale bar: 100 μm). (c) Shows quantification of Tbx4 cells counted in b (from 2 lobes/mouse, n=9 mice. ****p<0.001 by t test; mean±SEM). (d) Shows that Tbx4 cells were marked in Tbx4-CreER Confetti mice using 4 doses of Tamoxifen. Representative confocal images of a typical colony of Tbx4 cells. Cells in clone are numbered. (e) Shows Tbx4 colony size at baseline and d21 after bleomycin injury. *p<0.001 by t test; mean±SEM. In (f), five doses of tamoxifen were given to Tbx4– CreER;Rosa26-Tm every other day starting from d7 after bleomycin treatment. Lungs were harvested for histology on d21 after bleomycin. (g) Shows representative lung sections from Tbx4-CreER;Rosa26-Tm mice in f showing Tbx4 lineage cells in red and nuclei in blue (Scale bar: 100 μm). (h) Shows quantification of Tbx4 cells in g (from 2 lobes/mouse, n=9 mice. ****p<0.001 by t test; mean±SEM).
Figure 23:
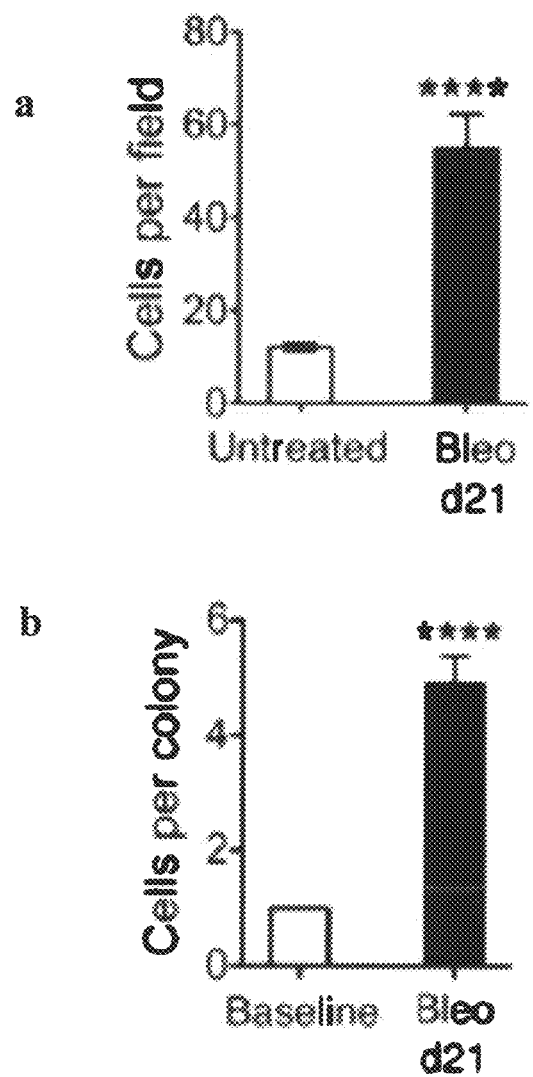
FIG. 23 shows Tbx4-lineage cells are highly proliferative upon bleomycin injury in the lung. (a) Shows quantification of Tbx4 cells counted in lung sections from Tbx4LME-CreER Rosa26-tdTomato mice with four doses of tamoxifen injection (2 lobes per mouse, n=9 mice, **p≤0.0001 by 2-tailed Student's t test, mean_+SEM). (b) Shows Tbx4 colony size at baseline and d21 after bleomycin injury (n=9 lungs examined, **p≤0.0001 by 2-tailed Student's t test, mean_+SEM).

FIGS. 9 and 23 show that Tbx cells proliferate and are induced de novo upon bleomycin injury in the lung. FIG. 9 (a) shows the experimental design for inducible Tbx4 cell labeling using tamoxifen one week before bleomycin injury for Tbx4-CreER;Rosa26-Tm mice. Four doses of Tam (tamoxifen) were given to the mice every other day. Lungs were harvested on d21. Tbx4-CreER;Rosa26-Tm and Tbx4-CreER;Confetti were used for all experiments in this figure. FIG. 9 (b) shows representative lung sections from Tbx4-CreER;Rosa26-Tm mice in a showing Tbx4 lineage cells in red and nuclei in blue (Scale bar: 100 µm). FIG. 9 (c) shows quantification of Tbx4 cells counted in b (from 2 lobes/mouse, n=9 mice. ****p<0.001 by t test; mean±SEM). FIG. 9 (d) shows that Tbx4 cells were marked in Tbx4-CreER;Confetti mice using 4 doses of Tamoxifen. Representative confocal images of a typical colony of Tbx4 cells. Cells in clone are numbered. FIG. 9 (e) shows Tbx4 colony size at baseline and d21 after bleomycin injury. *p<0.001 by t test; mean±SEM. In FIG. 9 (f), five doses of tamoxifen were given to Tbx4− CreER;Rosa26-Tm every other day starting from d7 after bleomycin treatment. Lungs were harvested for histology on d21 after bleomycin. FIG. 9 (g) shows representative lung sections from Tbx4-CreER;Rosa26-Tm mice in f showing Tbx4 lineage cells in red and nuclei in blue (Scale bar: 100 µm). FIG. 9 (h) shows quantification of Tbx4 cells in g (from 2 lobes/mouse, n=9 mice. **p<0.001 by t test; mean±SEM). FIG. 23 (a) shows quantification of Tbx4 cells counted in lung sections from Tbx4LME-CreER Rosa26-tdTomato mice with four doses of tamoxifen injection (2 lobes per mouse, n=9 mice, p≤0.0001 by 2-tailed Student's t test, mean_+SEM). FIG. 23 (b) shows Tbx4 colony size at baseline and d21 after bleomycin injury (n=9 lungs examined, **p≤0.0001 by 2-tailed Student's t test, mean_+SEM).

Figure 14:
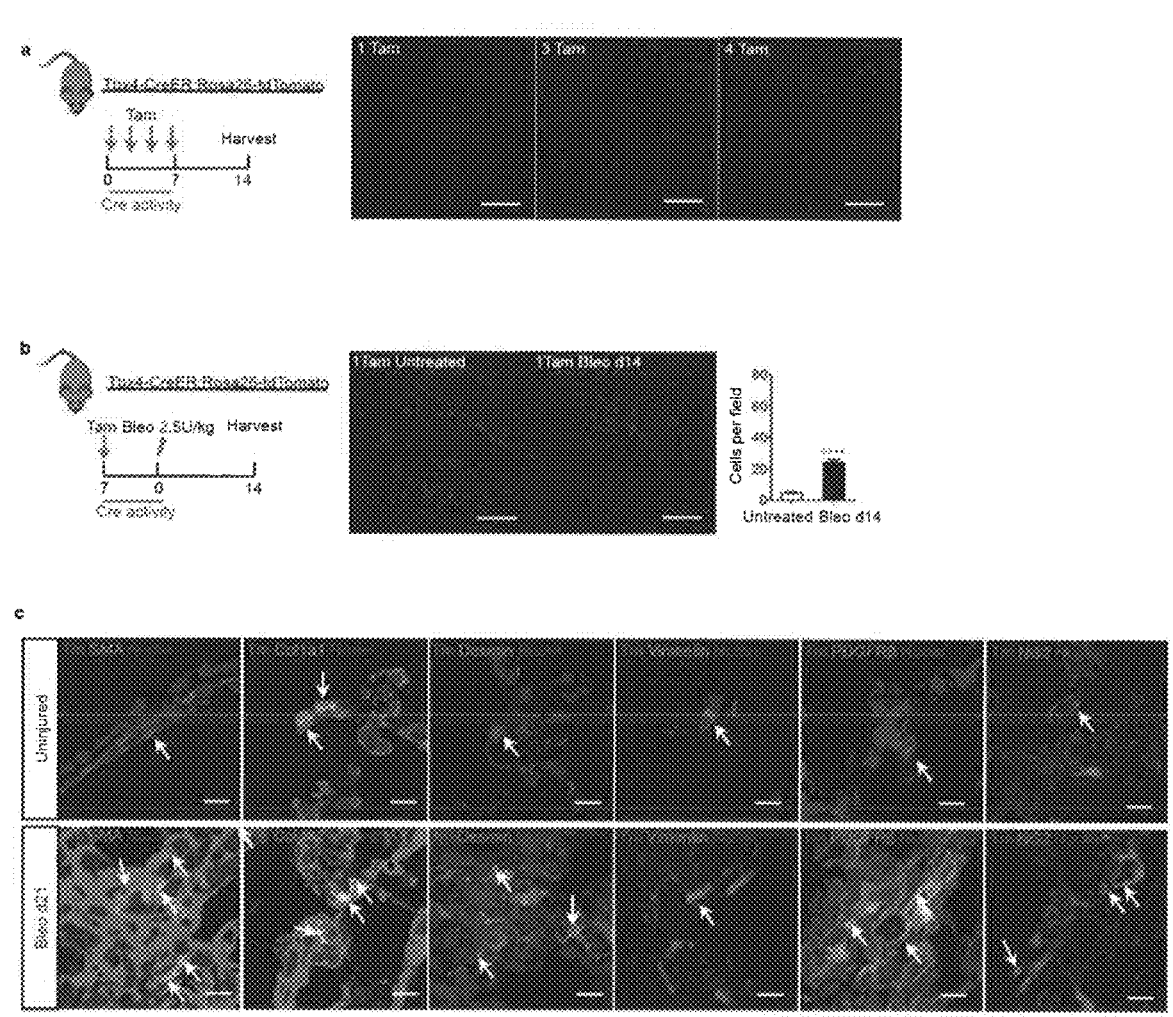
FIG. 14 shows Tbx lineage tracing in adult lung. (a) Shows the experimental design. Adult Tbx4-CreER;Rosa26-Tm mice were injected with 1, 3, or 4 doses of tamoxifen to label Tbx4 expressing cells. Tbx4 cell labeling was increased in a dose dependent pattern of Tamoxifen injection (n=6 lungs examined, scale bar: 100 μm). (b), Tbx4-CreER;Rosa26-Tm mice were injected with 1 dose of tamoxifen, followed with bleomycin injury, and lungs were harvested on d14. Representative histology images of uninjured and d14 mouse lung are presented. Quantification of Tbx4+ cells per area was counted (n=6 lungs examined, scale bar: 100 μm). (c) Shows representative immunofluorescence images of mice from b staining with (from left to right) αSMA, Col1a1, Desmin, Vimentin, PDGFRβ, and NG2. Arrows show cells with overlap in staining (n=6 lungs examined, scale bar: 10 μm).

FIG. 14 shows Tbx lineage tracing in adult lung. Panel (a) shows the experimental design. Adult Tbx4-CreER;Rosa26-Tm mice were injected with 1, 3, or 4 doses of tamoxifen to label Tbx4 expressing cells. Tbx4 cell labeling was increased in a dose dependent pattern of Tamoxifen injection (n=6 lungs examined, scale bar: 100 µm). For panel (b), Tbx4-CreER;Rosa26-Tm mice were injected with 1 dose of tamoxifen, followed with bleomycin injury, and lungs were harvested on d14. Representative histology images of uninjured and d14 mouse lung are presented. Quantification of Tbx4+ cells per area was counted (n=6 lungs examined, scale bar: 100 µm). Panel (c) shows representative immunofluorescence images of mice from b staining with (from left to right) αSMA, Col1a1, Desmin, Vimentin, PDGFRβ, and NG2. Arrows show cells with overlap in staining (n=6 lungs examined, scale bar: 10 µm).

One, three, or four doses of tamoxifen were administered one week before harvest. As shown in FIG. 14(a), increased labeling of Tbx4+ cells in adult mice was detected.

One dose or four doses of tamoxifen then were tested one week before bleomycin-induced injury. Fourteen or 21 d after bleomycin treatment, mouse lungs were harvested for frozen section. A significant increase of Tbx4+ cells was detected in mouse lungs 14 and 21 days after bleomycin treatment when compared with untreated lungs (FIG. 9(a)-(c), FIG. 14(b), FIG. 23 (a)). Tracing labeled Tbx4+ cells were co-stained with (from left to right) αSMA, Col1a1, Desmin, Vimentin, PDGFRβ and NG2 antibodies, as well as lipid acid and vWF antibodies (FIG. 14 c and FIG. 15b-c). The tracing labeled Tbx4+ cells did not co-stain with SPC, PDPN, and CC10. (FIG. 15d)

Figure 16:
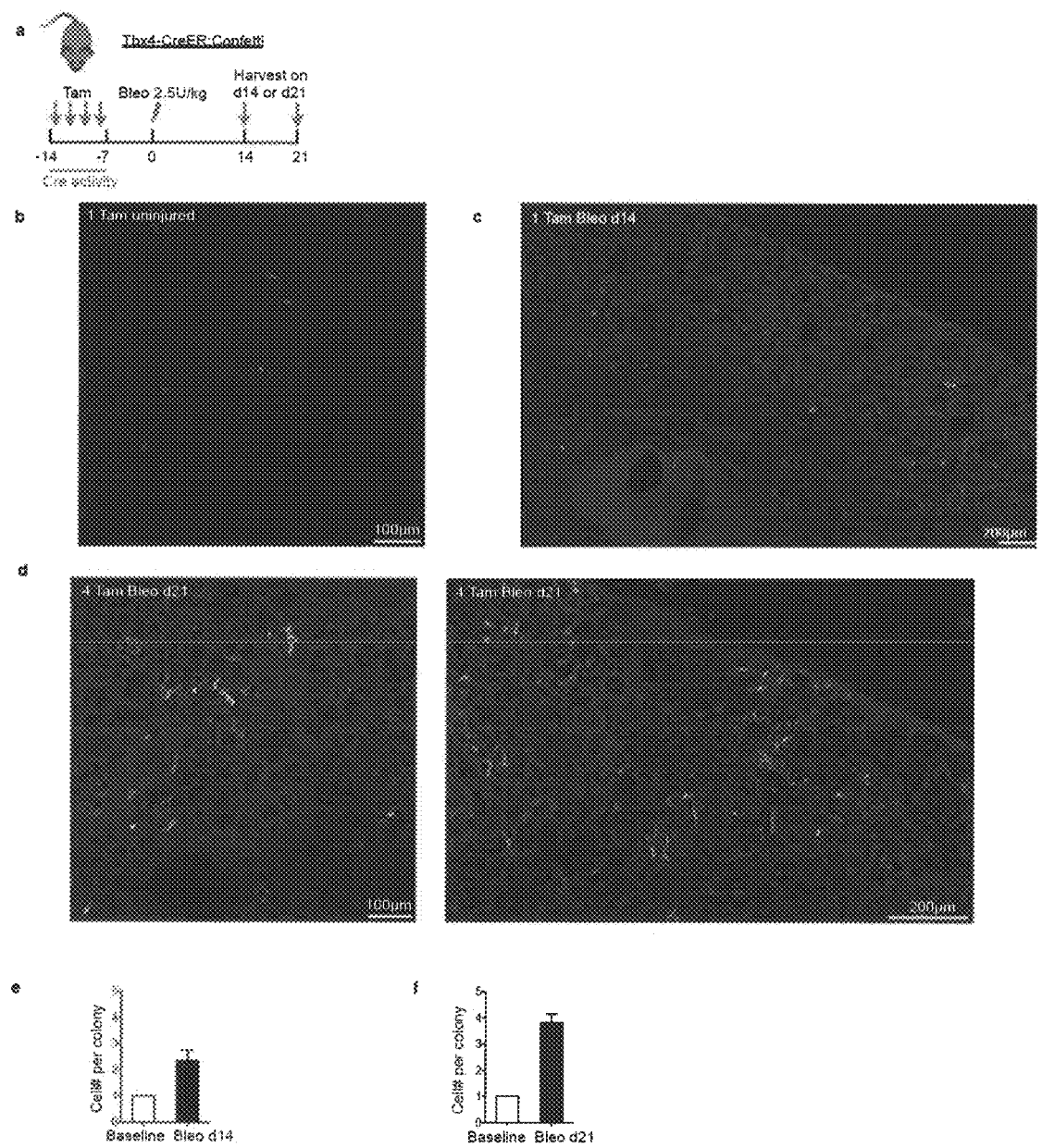
FIG. 16 shows clonal-like expansion of Tbx4+ fibroblasts during fibrosis. (a) Shows the experiment scheme: Tbx4+ cells were marked in Tbx4-CreER;Confetti mice using one or four doses of tamoxifen (12.5 μg/g/dose). Bleomycin injury was performed intratracheally one week after the last dose of tamoxifen. Mouse lungs were harvested at d14 and d21 for frozen section and confocal imaging. (b) Shows that preceeding bleomycin injury, single Tbx4+ cells were marked. (c) Shows that bleomycin injury induced Tbx4+ cell replication, producing clones of one or two identically marked cells. (d) Shows that bleomycin induced Tbx4+ cells self-renewal or clonal expansion. (e) Shows a histogram of Tbx4+ colony size in b and c. (f) Shows a histogram of Tbx4+ colony size in d (n=9 lungs examined in all experiment group, scale bar as indicated in figures).

Tbx4-CreER mice were crossed with confetti mice to determine if Tbx4 lineage cells are clonally expanded (FIG. 9(a)) (Livet et al. Nature. 2007 Nov. 1; 450(7166): 56-62). Cre-mediated recombination within the floxed (meaning located in between two lox P sites) reporter locus randomly activates one of its four colored reporters and indelibly marks the recombined cell and its progeny for their entire lifespan. Around 4 cells were found within one Tbx4+ clonal patch on d21 after bleomycin injury, which was significantly increased, compared to uninjured lung (FIG. 9d, e). The data also were confirmed by analyzing the lung on day 14; about 2-3 cells were found in one clonal patch. (FIG. 16 a-f). Analysis of clone size as a function of time following bleomycin exposure indicated that Tbx4-lineage cells underwent progressive clonal expansion after bleomycin exposure (FIG. 23 (b)).

FIG. 16 shows clonal-like expansion of Tbx4+ fibroblasts during fibrosis. Panel (a) shows the experiment scheme: Tbx4+ cells were marked in Tbx4-CreER;Confetti mice using one or four doses of tamoxifen (12.5 µg/g/dose). Bleomycin injury was performed intratracheally one week after the last dose of tamoxifen. Mouse lungs were harvested at d14 and d21 for frozen section and confocal imaging. Panel (b) shows that proceeding bleomycin injury, single Tbx4+ cells were marked. Panel (c) shows that Bleomycin injury induced Tbx4+ cell replication, producing clones of one or two identically marked cells. Panel (d) shows that bleomycin induced Tbx4+ cells self-renewal or clonal expansion. Panel (e) is a histogram of Tbx4+ colony size in b and c. Panel (f) is a histogram of Tbx4+ colony size in d (n=9 lungs examined in all experiment group, scale bar as indicated in figures).

These data demonstrated that Tbx4 lineage fibroblasts undergo clonal-like expansion during lung injury and fibrosis.

Figure 17:
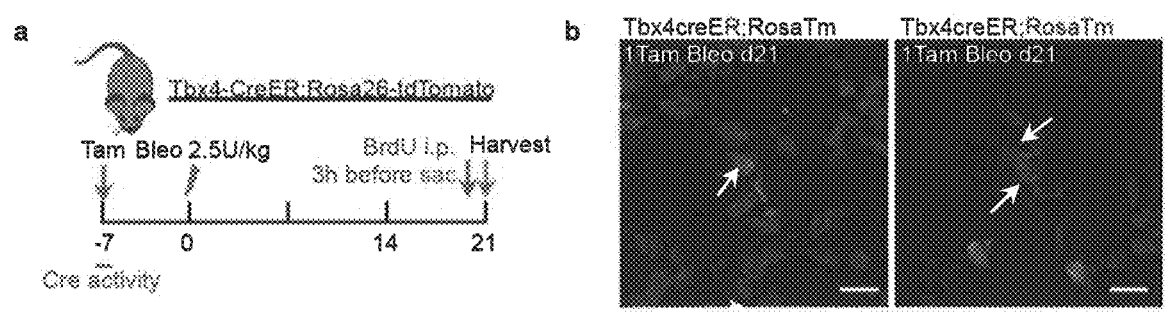
FIG. 17 shows that injury induces Tbx4+ cell proliferation. (a) Shows the BrdU labeling experiment scheme: Tbx4+ cells were marked in Tbx4-CreER;Rosa-Tm mice using one dose of tamoxifen (20 μg/g/dose). Bleomycin injury was performed intratracheally one week after tamoxifen administration. On bleomycin injured d21, BrdU was injected intraperitoneally 3 hrs before lung harvesting. Frozen section and confocal imaging were performed thereafter. (b) Shows representative images showing the Tbx4+ cells are incorporated with BrdU (arrowheads, n=3 mice examined, scale bar=10 μm).

BrdU labeling also indicated that Tbx4+ cells labeled before injury were proliferating in Tbx4-CreER;Rosa26-tdTomato mice 21 days after bleomycin treatment (FIG. 17, a, b).

FIG. 17 shows that injury induces Tbx4+ cell proliferation. Panel (a) shows the BrdU labeling experiment scheme: Tbx4+ cells were marked in Tbx4-CreER;Rosa-Tm mice using one dose of tamoxifen (20 µg/g/dose). Bleomycin injury was performed intratracheally one week after tamoxifen administration. On bleomycin injured d21, BrdU was injected intraperitoneally 3 hrs before lung harvesting. Frozen section and confocal imaging were performed thereafter. Panel (b) shows representative images showing that the Tbx4+ cells are incorporated with BrdU (arrowheads, n=3 mice examined, scale bar=10 µm).

In order to label Tbx4+ cells after injury, five doses of tamoxifen were administered every other day beginning one week following bleomycin injection in Tbx4-CreER; Rosa26-tdTomato mice and the lungs were harvested on d21 (FIG. 9(f)). A significant increase of Tbx4+ cells was observed in the bleomycin treated mice when compared with un-treated mice (FIG. 9 g, h). Those Tbx4+ cells in bleomycin treated mice co-stained with αSMA, Desmin, Vimentin, Col1a1, NG2, and PDGFRβ (FIG. 18 a, b).

Figure 18:
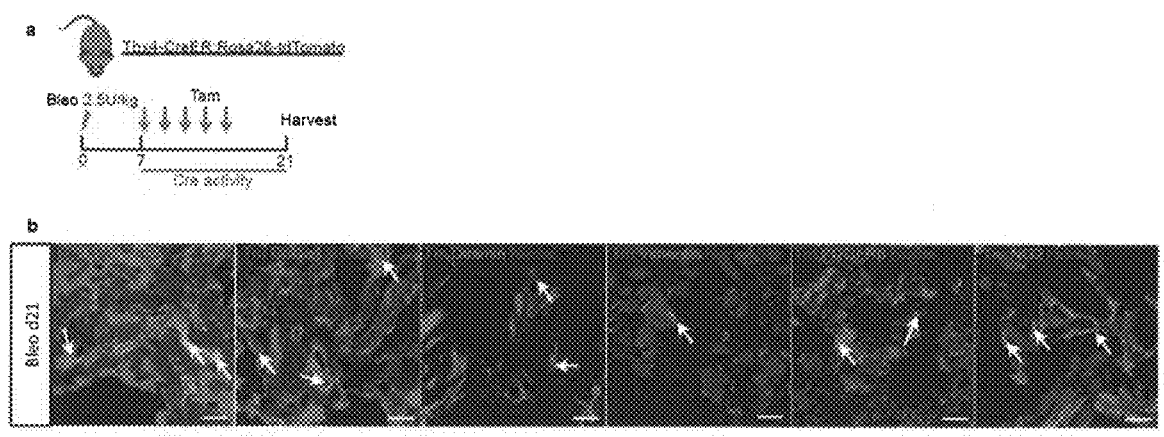
FIG. 18 shows that injury induced Tbx4+ cells were co-expressed with stromal cell markers. (a) Shows the experimental design. In order to label Tbx4+ cells after injury, Tbx4− CreER;Rosa26-Tm mice were injured with intratracheal bleomycin (2.5 U/kg), followed by 5 doses of tamoxifen beginning at d7. Lungs were harvested for frozen section and immunofluorescence staining. (b) Representative images of (from left to right) SMA, Col1a1, Desmin, Vimentin, PDGFRβ, and NG2 immunofluorescence staining. Arrows showing the overlap cells (n=9 mice examined, scale bar: 10 μm).

FIG. 18 shows that injury induced Tbx4+ cells were co-expressed with stromal cell markers. Panel (a) shows the experimental design. In order to label Tbx4+ cells after injury, Tbx4− CreER;Rosa26-Tm mice were injured with intratracheal bleomycin (2.5 U/kg), followed by 5 doses of tamoxifen beginning at d7. Lungs were harvested for frozen section and immunofluorescence staining. (b) Representative images of (from left to right) αSMA, Col1a1, Desmin, Vimentin, PDGFRβ, and NG2 immunofluorescence staining. Arrows showing the overlap cells (n=9 mice examined, scale bar: 10 µm).

The data indicate that Tbx4+ cells labeled before and after injury both proliferated and contributed to the expansion of Tbx4+ cells.

Ablation of Tbx4 Cells or Signaling Inhibits Pulmonary Fibrosis

To directly demonstrate the functional role of Tbx4+ fibroblasts and their cellular progeny in lung fibrosis, Tbx4-CreER mice were crossed with Rosa26-Stop-DTA mice, which express diphtheria toxin fragment A (DTA) under control of the Tbx4 locus, or Rosa260tdTomato Rosa26-Stop-DTA mice. The tamoxifen-inducible, Cre-mediated combination results in deletion of Tbx4-expressing cells. These mice were given five injections of tamoxifen for 1 week after bleomycin treatment to induce ablation of Tbx4+ cells (FIG. 10 and FIG. 24 (a)).

Figure 10:
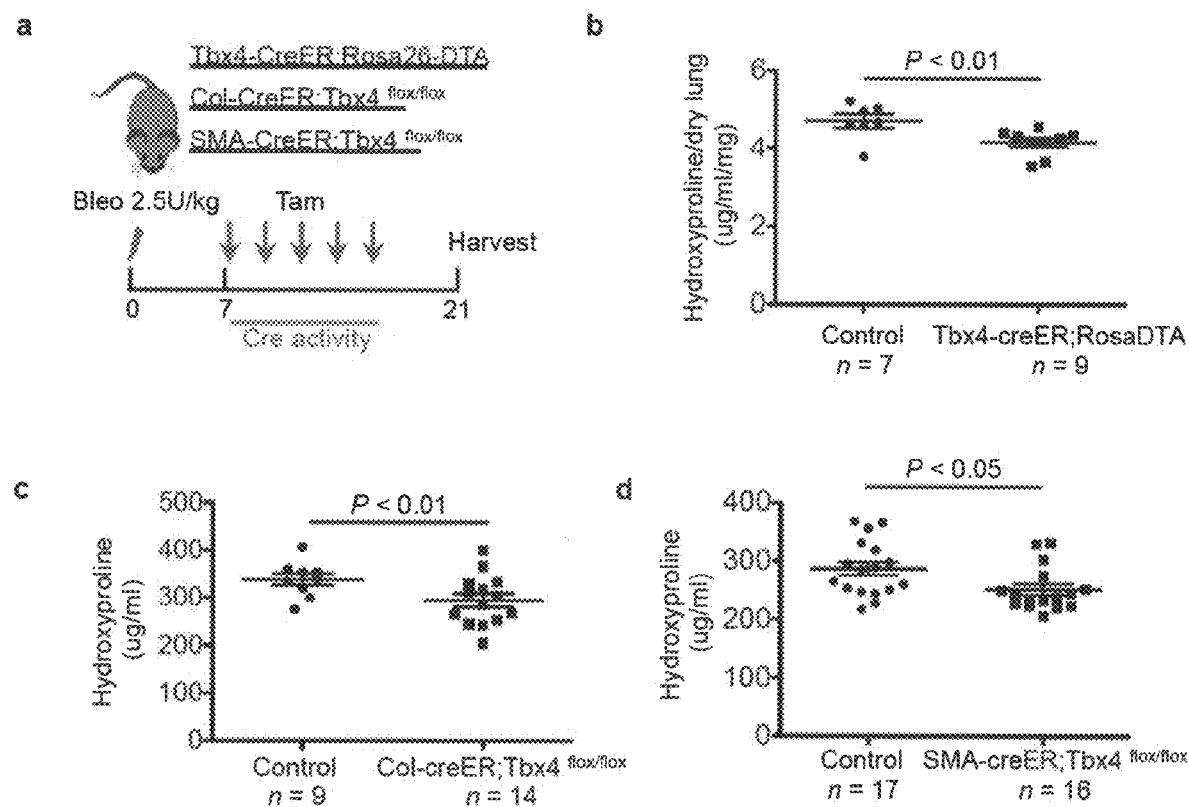
FIG. 10 shows that ablation of Tbx cells or loss of Tbx4 expression inhibits pulmonary fibrosis. (a) Shows the experimental strategy for inducible ablation of Tbx4 cells or Tbx4 expression in Col1a2+ and αSMA+ cells. Tbx4-CreER;Rosa26-DTA, Col1a2-CreER;Tbx4$^{flox/flox}$, and SMA-CreER;Tbx4$^{flox/flox}$ mice were used in these experiments. The above mentioned transgenic mice and their WT littermates (8-16 weeks old) were treated with bleomycin (2.5 U/kg), followed by 5 doses of tamoxifen (20 μg/g/dose) every other day starting on d7. The lungs were collected for hydroxyproline content determination on d21. DTA, diphtheria toxin fragment A. (b) Shows that targeting Tbx4 cells reduced lung fibrosis. The data in (b) are presented as means±SEM. (p<0.01, Student's t-test; Tbx4-CreER;Rosa-DTA, n=7, control, n=9). (c) Shows that knock down Tbx4 in Col1a2 expressing cells decrease hydroxyproline. The data in (c) are presented as means±SEM. (p<0.01, Student's t-test; Col-CreER;Tbx4flox/flox, n=9, control, n=14). (d) Shows the result of inhibiting Tbx4 in αSMA+ cells. The data in (d) are presented as means±SEM. (p<0.05, Student's t-test; SMA-CreER;Tbx4 flox/flox, n=17, control, n=16).

FIG. 10 shows that ablation of Tbx cells or loss of Tbx4 expression inhibits pulmonary fibrosis. Panel (a) shows the experimental strategy for inducible ablation of Tbx4 cells or Tbx4 expression in Col1a2+ and αSMA+ cells. Tbx4-CreER;Rosa26-DTA, Col1a2-CreER;Tbx4flox/flox, and SMA-CreER;Tbx4 flox/flox mice were used in these experiments. The above mentioned transgenic mice and their WT littermates (8-16 weeks old) were treated with bleomycin (2.5 U/kg), followed by 5 doses of tamoxifen (20 µg/g/dose) every other day starting on d7. The lungs were collected for hydroxyproline content determination on d21. DTA, diphtheria toxin fragment A. Panel (b) shows that targeting Tbx4 cells reduced lung fibrosis. The data in (b) are presented as means±SEM. (p<0.01, Student's t-test; Tbx4-CreER;Rosa-DTA, n=7, control, n=9). Panel (c) shows that knock down Tbx4 in Col1a2 expressing cells decrease hydroxyproline. The data in (c) are presented as means±SEM. (p<0.01, Student's t-test; Col-CreER;Tbx4flox/flox, n=9, control, n=14). Panel (d) shows the result of inhibiting Tbx4 in αSMA+ cells. The data in (d) are presented as means±SEM. (p<0.05, Student's t-test; SMA-CreER;Tbx4 flox/flox, n=17, control, n=16).

Figure 25:
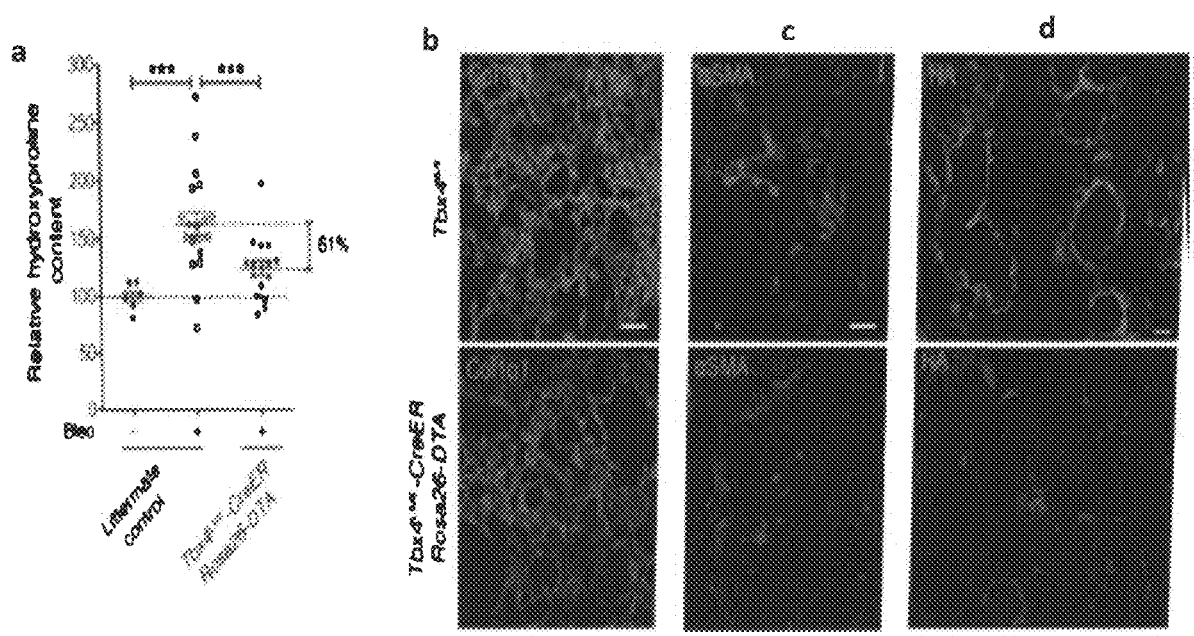
FIG. 25 shows that ablation of TBX4 cells attenuates pulmonary fibrosis. (a) Shows targetingTBX4 cells reduced lung fibrosis (means±SEM, ***p<0.001,1-way ANOVA with Bonferroni test; uninjured littermate control, n=S; bleomycin [Bleo] littermate control, n=20; Tbx4$^{LME}$-CreER Rosa26-DTA, n=16). (b-d) shows representative images of COL1a1 (b), αSMA (c), and HA (d) immunofluorescence staining of d21 Tbx4$^{LME}$-CreER Rosa26-DTA mouse lung. n=6 mice per group examined. Scale bars: 100 nm (b-d).

A significant decrease in collagen content was detected in tamoxifen injected Tbx4-CreER;Rosa26-DTA mouse lungs 21 days after bleomycin treatment (FIG. 10 b) and hydroxyproline assay (FIG. 25 (a)), although the survival of Tbx4-CreER;Rosa26-DTA mice was not significantly different from that of the control group (FIG. 17 a, b). Immunfluorescence analysis also revealed decreasing COL1a1, αSMA and HA expression (FIGS. 25 (b)-(d)).

Figure 24:
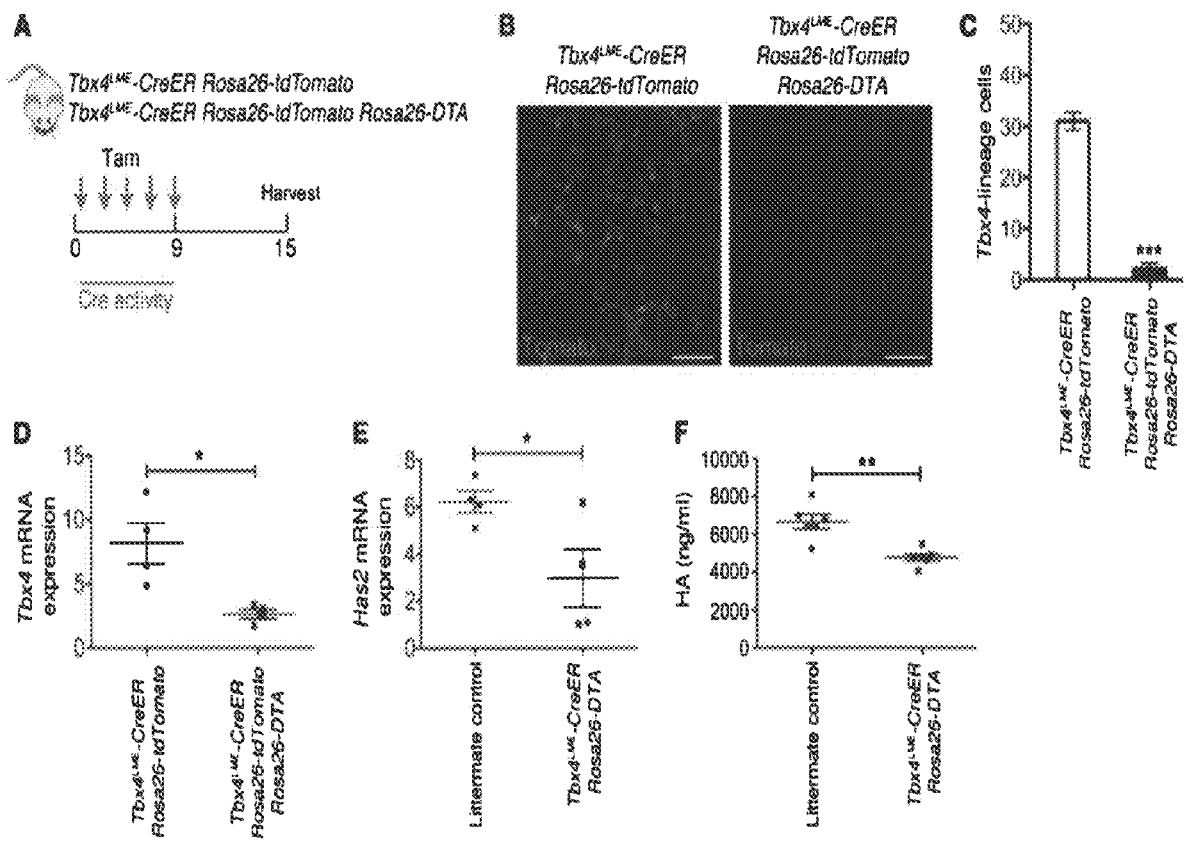
FIG. 24 shows that ablation of TBX4 cells decreases HAS2 and HA expression. (a) Shows verification of ablation of Tbx4-lineage cells using Tbx4$^{LME}$-CreER Rosa26-tdTomato and Tbx4$^{LME}$-CreER Rosa26-tdTomato Rosa26-DTA mice. Five doses of tamoxifen were injected, and lungs were harvested 1 week later. (b) Shows representative images taken from Tbx4$^{LME}$-CreER Rosa26-tdTomato and Tbx4$^{LME}$-CreER Rosa26-tdTomato Rosa26-DTA mouse lung (n=4 lungs examined). (c) shows quantification of Tbx4 lineage tracing and ablation, expressed as cells counted in B (n=4 in each group of mice). (d and e) shows Tbx4 mRNA (d) and Has2 mRNA (e) expression of lung fibroblasts from Tbx4$^{LME}$-CreER Rosa26-tdTomato and Tbx4$^{LME}$-CreER Rosa26-tdTomato Rosa26-DTA analyzed by quantitative RT-PCR, and normalized by GAPDH (n=4 mice per group examined). (f) Shows HA contents in conditioned media of lung fibroblasts from Tbx4$^{LME}$-CreER Rosa26-tdTomato and littermate controls analyzed by HA ELISA. n=6 mice per group examined. *P<0.05, P<0.01, *P<0.001 by 2-tailed Student's t test, mean±SEM.

Injection of tamoxifen induced a marked reduction of progeny of TBX4 cells (tdT+ cells) (FIGS. 24 (b) and (c)), of Tbx4 and Has2 mRNA and of HA production in lung fibroblasts (FIG. 24 (d)-(f)).

Figure 20:
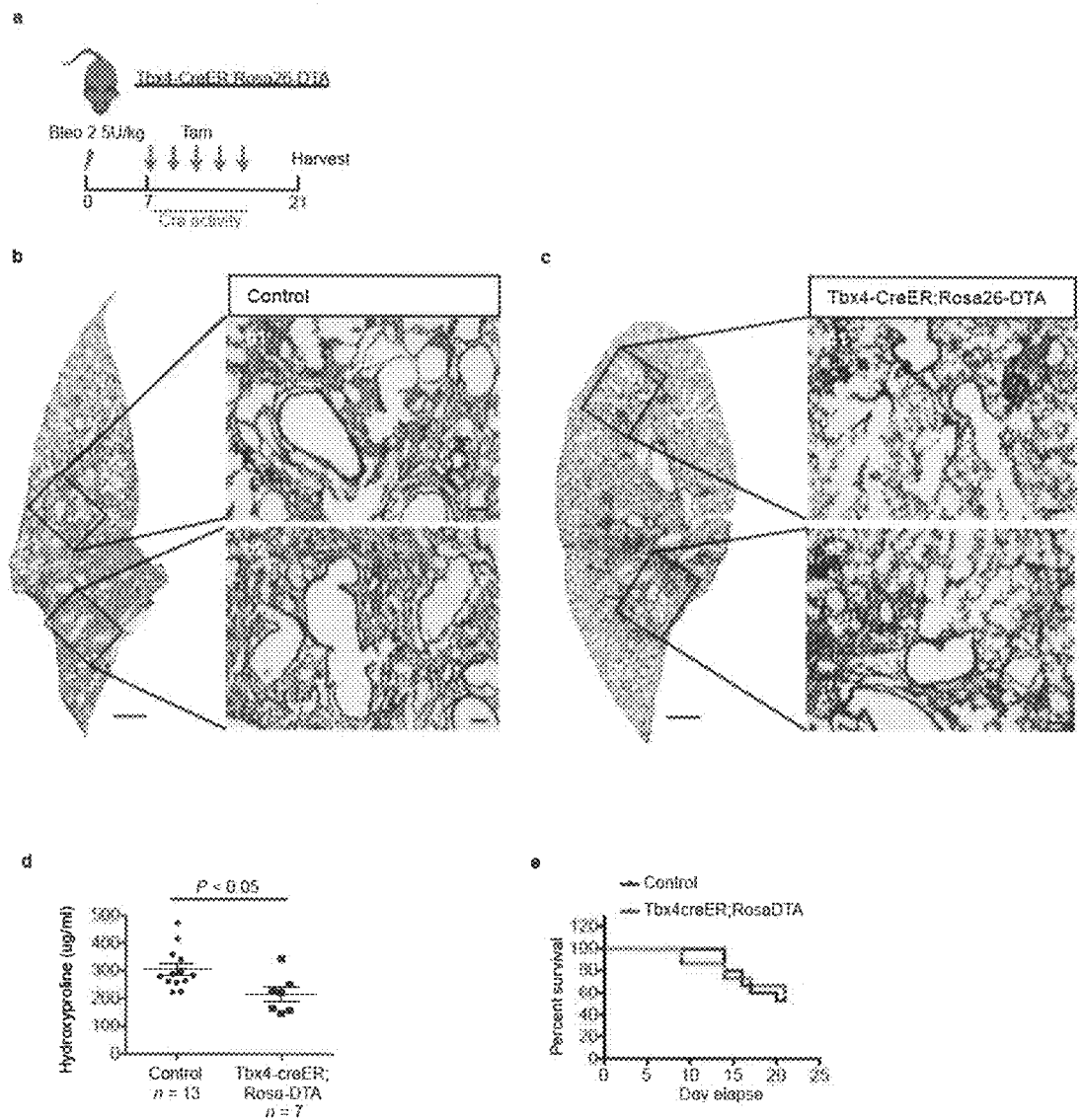
FIG. 20 shows that depletion of Tbx4+ cells reduced collagen but did not affect survival after bleomycin injury. (a) Shows the strategy for inducible ablation of Tbx4 cells. Tbx4-CreER;Rosa26-DTA mice and their WT littermates (8-16 weeks old) were administered with bleomycin (2.5 U/kg) intratracheally. Seven days later, mice were injected with 5 doses of tamoxifen (20 ng/g/dose) for every other day (day 7~15). (b~c) Show representative Masson's trichrome staining for control (b, b1, b2) and Tbx4-CreER;RosaDTA (c, c1, c2) mice. Scale Bars: indicate 1 mm (b and c) and 100 μm (b1, b2, c1, c2). (d) Shows that ablation of Tbx4 cells decrease hydroxyproline concentration in whole lung. (e) Shows survival curves of Tbx4-CreER;Rosa-DTA mice and their WT littermates.

FIG. 20 shows that depletion of Tbx4+ cells reduces collagen but did not affect survival after bleomycin injury. Panel (a) shows the strategy for inducible ablation of Tbx4 cells. Tbx4-CreER;Rosa26-DTA mice and their WT littermates (8-16 weeks old) were administered with bleomycin (2.5 U/kg) intratracheally. Seven days later, mice were injected with 5 doses of tamoxifen (20 ng/g/dose) for every other day (day 7~15). Panels (b~c) show representative Masson's trichrome staining for control (b, b1, b2) and Tbx4-CreER;RosaDTA (c, c1, c2) mice. Scale Bars: indicate 1 mm (b and c) and 100 µm (b1, b2, c1, c2). Panel (d) shows that ablation of Tbx4 cells decrease hydroxyproline concentration in whole lung. Panel (e) shows survival curves of Tbx4-CreER;Rosa-DTA mice and their WT littermates.

Thus, the loss of Tbx4+ cells and their progeny attenuated interstitial fibrosis.

Figure 26:
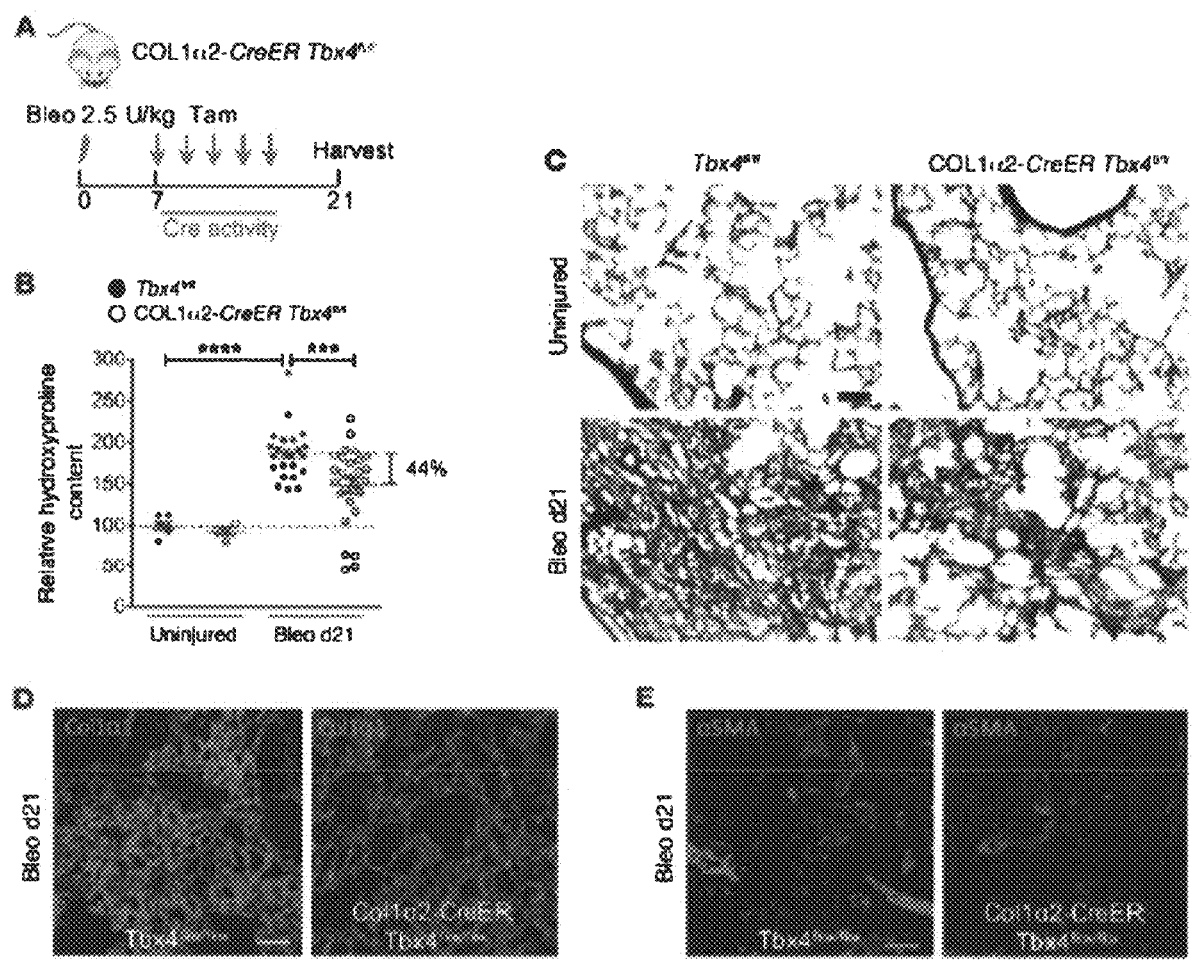
FIG. 26 shows that loss of TBX4 expression in COL1a2-expressing cells attenuates pulmonary fibrosis. (a) Shows a schematic depicting the strategy for inducible knockout of TBX4 expression in COL1a2+ cells. Col1a2-CreER Tbx4$^{fl/fl}$ mice were used in these experiments. The above-mentioned mice and their WT littermates (8-16 weeks old) were treated with bleomycin (2.5 U/kg), followed by 5 doses of tamoxifen (20 mg/g/injection) every other day starting on d7. The lungs were collected for hydroxyproline content determination on d21 after bleomycin. (b) shows knockdown of Tbx4 in COL1a2-expressing cells decreased hydroxyproline content (means±SEM, *P<0.001, **P<0.0001, n=6 in uninjured Tbx4$^{fl/fl}$ group, n=4 in uninjured Col1a2-CreER Tbx4fl/flgroup, n=23 in bleo Tbx4$^{fl/fl}$ group, n=27 in bleo Col1a2-CreER Tbx4$^{fl/fl}$ group). (c) Shows representative Masson's trichrome staining from lungs at d21 after bleomycin injection, showing decreased collagen deposition (blue) in Col1a2-CreER Tbx4$^{fl/fl}$. (d and e) Show images of COL1a1 (d) and αSMA (e) antibody staining for bleo d21 Col1a2-CreER Tbx4$^{fl/fl}$ mouse lung. n=6 mice per group examined. Scale bars: 100 μm (c-e).

To elucidate the role of Tbx4 signaling in lung fibrosis, the impact of deletion of Tbx4 signaling in fibroblasts or myofibroblasts was evaluated. Col1a2-CreER transgenic mice were crossed with Tbx4$^{flox/flox}$ mice (Arora et al. PLoS Genet. 2012; 8(8): e1002866), resulting in Tbx4 gene deletion in collagen-expressing cells (FIG. 10(a) and FIG. 26 (a)). Five doses of tamoxifen were administered 1 week following bleomycin treatment. Hydroxyproline content in Col1a2-CreER;Tbx4$^{flox/flox}$ mouse lungs was significantly decreased (~44%) compared to control mice 21 days after bleomycin treatment (FIG. 10(c) and FIG. 26 (b)). Masson's trichrome and immunofluorescence staining of the lung for collagen, COL1a1 and αSMA also showed similar results (FIGS. 26 (c)-(e)).

Figure 27:
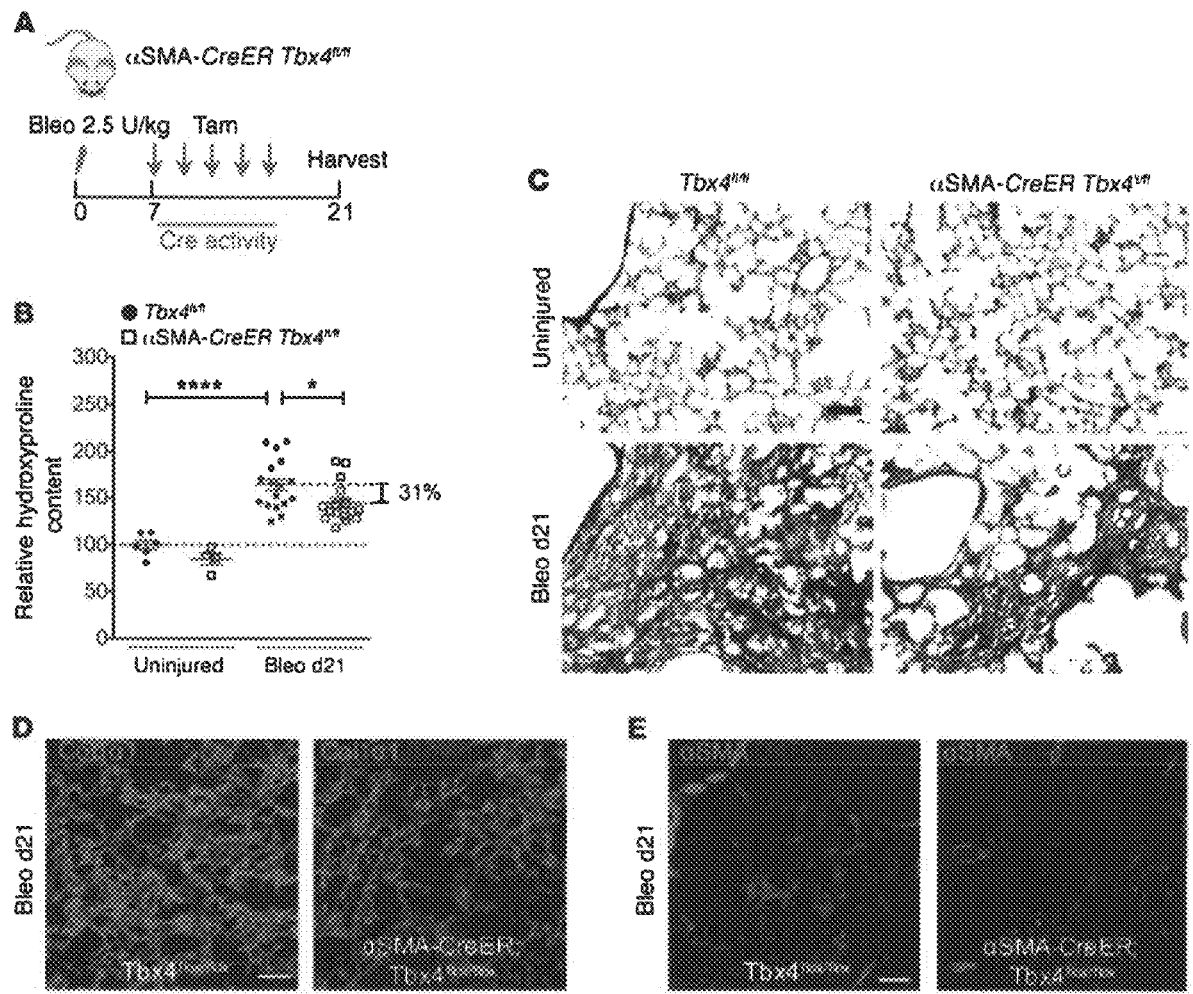
FIG. 27 shows Inhibition of Tbx4 in αSMA+ cells attenuates lung fibrosis. (a) Shows a schematic depicting the strategy for inducible knockout of Tbx4 expression in αSMA+ cells. Acta2-CreER Tbx4$^{fl/fl}$ mice were used in these experiments. The above-mentioned mice and their WT littermates (8-16 weeks old) were treated with bleomycin (2.5 U/kg), followed by 5 doses of tamoxifen (20 mg/g/ injection) every other day starting on d7. The lungs were collected for hydroxyproline content determination on d21 after bleomycin. (b) Shows knockdown of Tbx4 in αSMA-expressing cells decreased hydroxyproline content (means±SEM, *P<0.05, ****P<0.0001, n=6 in uninjured Tbx4fl/fl group, n=4 in uninjured Acta2-CreER Tbx4$^{fl/fl}$ group, n=17 in bleo Tbx4$^{fl/fl}$ group, n=16 in bleo Acta2-CreER Tbx4$^{fl/fl}$ group). Hydroxyproline content values were expressed as percentage of control Tbx4$^{fl/fl}$ group, which is set to 100%. One-way ANOVA with Bonferroni test was used. (c) Shows representative Masson's trichrome staining from lungs at d21 after bleomycin injection, showing decreased collagen deposition (blue) in Acta2-CreER Tbx4$^{fl/fl}$ mice. (d and e) shows representative images of COL1a1 (d) and αSMA (e) antibody staining for bleo d21 Acta2-CreER Tbx4$^{fl/fl}$ mouse lung. n=6 mice per group examined. Scale bars: 100 μm (c-e).

In addition, Tbx4$^{flox/flox}$ mice were crossed with SMA-CreER mice in order to delete the Tbx4 gene in αSMA-expressing myofibroblasts when tamoxifen was administered (FIG. 10(a) and FIG. 27 (a)). Tbx4 knock-out in αSMA+ cells with five injections of tamoxifen 1 week following bleomycin treatment was found to reduce collagen content and aSMA expression compared to control mice 21 days after bleomycin treatment as determined by hydroxyproline assay (~31%) and Masson's trichrome staining and immunofluorescence (FIG. 10 d and FIGS. 27 (b)-(e)).

These data indicate that Tbx4-lineage cells play a role in regulating fibrosis in the bleomycin-induced lung injury model and that the loss of TBX4-expressing cells and their progeny attenuated interstitial lung fibrosis.

Tbx4 Regulates Fibroblast Invasion Through HAS2

A fraction of lung fibroblasts are invasive in patients with IPF (Li et al. J Exp Med. 2011 Jul. 4; 208(7): 1459-71;

White, E S et al., 2003, J. Pathol. 201: 343-354) and the fibroblast invasion phenotype determines fibrosis progression (Li et al., 2011). It was previously shown that hyaluronan synthase 2 (HAS2), hyaluronan (HA) receptor CD44, and beta-arrestins regulate fibroblast invasion in vitro and in vivo (Li et al. J Exp Med. 2011 Jul. 4; 208(7): 1459-71; Lovgren et al. Sci Transl Med. 2011 Mar. 16; 3(74): 74ra23).

The differences in invasiveness behavior between Tbx4+ fibroblasts and Tbx4− fibroblasts were evaluated. Tbx4− fibroblasts were isolated from Tbx4-Cre$^{Tg}$;Rosa26-tdTomato mouse lungs, cultured in vitro for 3 passages, and the tdTomato+ and tdTomato− cells were flow sorted.

Figure 21:
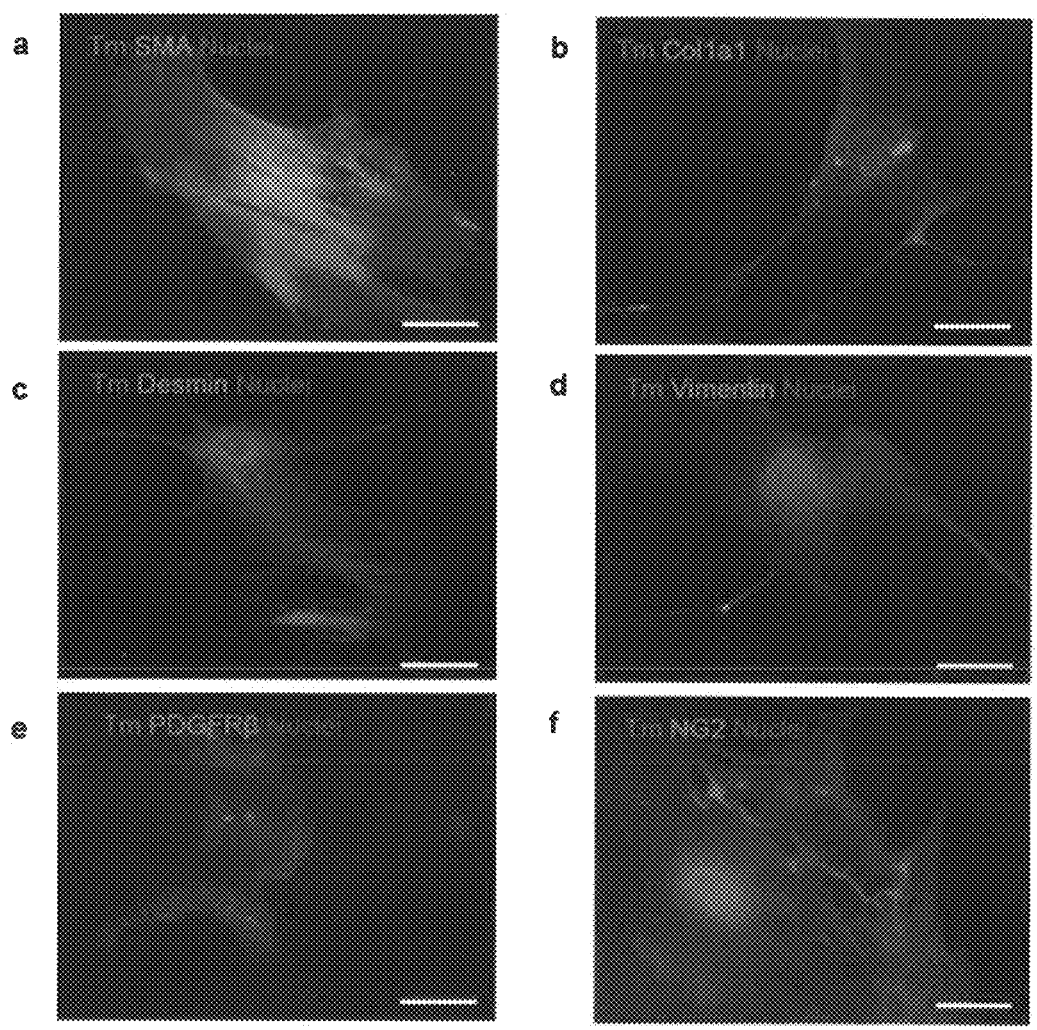
FIG. 21 shows that Tm+ cells express stromal cell markers in culture. Lung fibroblasts were cultured from uninjured Tbx4-Cre:Rosa26-Tm mice. TdTomato positive cells were sorted with flow cytometry and cultured for immunofluorescence staining. Representative images for αSMA (a), Col1a1 (b), Desmin (c), Vimentin (d), PDGFRβ (e), and NG2 (f) (n=3 mice examined, scale bar: 10 μm).

FIG. 21 shows that Tm+ cells express stromal cell markers in culture. Lung fibroblasts were cultured from uninjured Tbx4-Cre:Rosa26-Tm mice. TdTomato positive cells were sorted with flow cytometry and cultured for immunofluorescence staining. Representative images for αSMA (a), Col1a1 (b), Desmin (c), Vimentin (d), PDGFRβ (e), and NG2 (f) (n=3 mice examined, scale bar: 10 µm). Immunofluorescence staining for the sorted tdTomato cells revealed co-staining with αSMA, Desmin, Vimentin, Col1a1, NG2, and PDGFRβ (FIG. 21).

Microarrays were performed by using the RNAs isolated from sorted tdTomato+ and tdTomato− cells, and the tdTomato+ cells were found to have more than a 2 fold increase of Tbx4 transcript expression over the tdTomato− cells.

Figure 11:
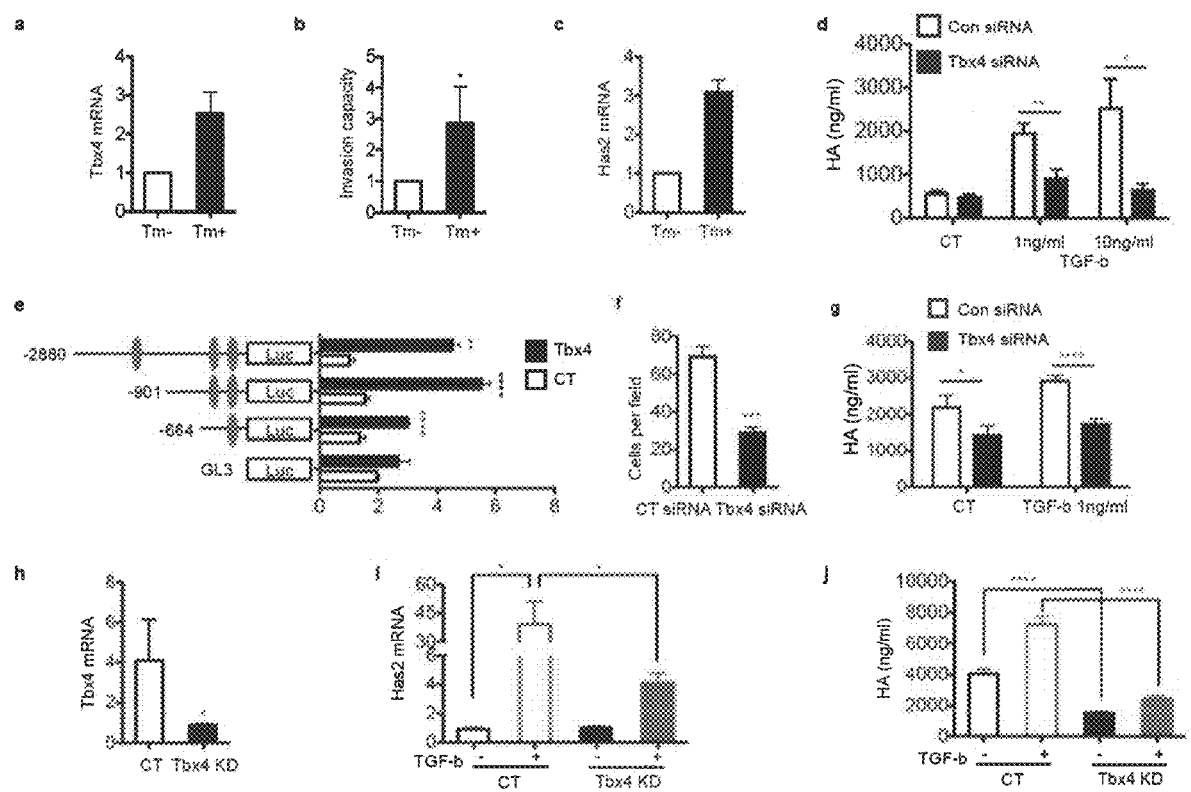
FIG. 11 shows that Tbx4 regulates fibroblast invasion through regulation of Has2. (a) Shows that Tbx4 mRNA expression is increased in sorted tdTomato positive cells from Tbx4-Cretg;Rosa26-Tm mice. (b) Shows that Tm+ fibroblasts are more invasive. Mean of 3 biological replicates ±SEM, *p<0.05, Student's t-test. (c) Shows that the level of Has2 mRNA is elevated in Tm+ fibroblasts. (d) Shows that Tbx4 siRNA reduced TGF-β-induced HA release by mouse fibroblast 3T3 cells. Mean of three biological replicates ±SEM, *p<0.05, **p<0.01 by one-way ANOVA. (e) Shows Tbx4 enhanced Has2 promoter activity. All Has2 promoter constructs show increased activity over the promoter-less vector pGL3 when co-transfected with Tbx4-expressing vector. For panel (f), an invasion assay for IPF fibroblasts was performed 48 hrs after transfection of control and Tbx4 siRNA. (f) Shows that knocking down Tbx4 with siRNA can reduce the invasiveness of IPF fibroblasts. (g) Shows that knocking down Tbx4 with siRNA reduced HA production of primary fibroblasts from IPF patient with or without 1 ng/ml TGF-β treatment after 48 hrs (*p<0.05, ****p<0.001 by one-way ANOVA; mean of 3 biological replicates ±SEM). (h-j) MEF cells were isolated and cultured from E14 embryo of CMV-Cre;Tbx4f/w and WT mice. MEF cells at passage 3 were used for experiments. (h) Tbx4 mRNA levels were compared between Tbx4-deficient and WT MEFs. (i) MEF cells were treated with or without TGF-β 5 ng/ml for overnight. Has2 mRNA expression was analyzed using RT-PCR. (j) HA in supernatants was measured with HA ELISA. All results are the mean of triplicate experiments ±SEM. *p<0.05, ****p<0.0001, as analyzed by one-way ANOVA.

FIG. 11 shows that Tbx4 regulates fibroblast invasion through regulation of Has2. Panel (a) shows that Tbx4 mRNA expression is increased in sorted tdTomato positive cells from Tbx4-Cretg;Rosa26-Tm mice. Panel (b) shows that Tm+ fibroblasts are more invasive. Mean of 3 biological replicates ±SEM, *p<0.05, Student's t-test. Panel (c) shows that the level of Has2 mRNA is elevated in Tm+ fibroblasts. Panel (d) shows that Tbx4 siRNA reduced TGF-β-induced HA release by mouse fibroblast 3T3 cells. Mean of three biological replicates ±SEM, *p<0.05, **p<0.01 by one-way ANOVA. Panel (e) shows Tbx4 enhanced Has2 promoter activity. All Has2 promoter constructs show increased activity over the promoter-less vector pGL3 when co-transfected with Tbx4-expressing vector. For panel (f), an invasion assay for IPF fibroblasts was performed 48 hrs after transfection of control and Tbx4 siRNA. Panel (f) shows that knocking down Tbx4 with siRNA can reduce the invasiveness of IPF fibroblasts. Panel (g) shows that knocking down Tbx4 with siRNA reduced HA production of primary fibroblasts from IPF patient with or without 1 ng/ml TGF-β treatment after 48 hrs (*p<0.05, ****p<0.001 by one-way ANOVA; mean of 3 biological replicates ±SEM). (h-j) MEF cells were isolated and cultured from E14 embryo of CMV-Cre;Tbx4f/w and WT mice. MEF cells at passage 3 were used for experiments. (h) Tbx4 mRNA levels were compared between Tbx4-deficient and WT MEFs. (i) MEF cells were treated with or without TGF-β 5 ng/ml for overnight. Has2 mRNA expression was analyzed using RT-PCR. (j) HA in supernatants was measured with HA ELISA. All results are the mean of triplicate experiments ±SEM. *p<0.05, ****p<0.0001, as analyzed by one-way ANOVA.

Tbx4+ cells were found to be more invasive compared with Tbx4-cells in a Matrigel invasion assay (FIG. 11b).

To determine if the invasiveness of Tbx4+ fibroblasts was due to expression of HAS2, the expression levels of HAS2 between Tbx4+ fibroblasts and Tbx4-fibroblasts were compared. More Has2 mRNA was in Tbx4+ fibroblasts when compared to Tbx4− cells (FIG. 11c). Furthermore, knock down of Tbx4 with specific siRNA decreased TGF-β-induced HA production in 3T3 mouse fibroblasts, suggesting HAS2 may be regulated by Tbx4 (FIG. 11d).

Figure 28:
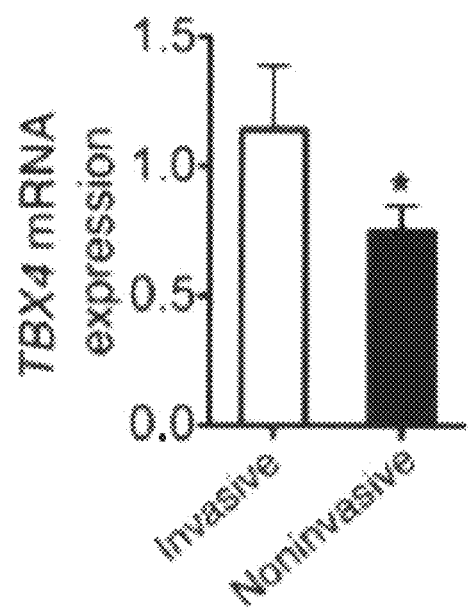
FIG. 28 shows a graph of invasion assay results for idiopathic pulmonary fibrosis (IPF) fibroblasts performed 48 hours after transfection of control and TBX4 siRNA.

There are three putative T box response elements in Has2 promoter (Arora et al., 2012a). Luciferase promoter assay showed that Tbx4 could significantly induce luciferase activity of luciferase vectors containing the Has2 promoters (FIG. 11e), suggesting Tbx4 regulates Has2 through transcription regulation. In addition, we obtained MEF cells from CMV-Cre;Tbx4f/w mice, designated Tbx4KD cells. Tbx4 mRNA expression in Tbx4KD MEF cells was significantly less than that of control MEF cells (FIG. 11(h)). TGF-β-induced Has2 mRNA expression was decreased in Tbx4KD MEF cells (FIG. 11(i)). HA production in Tbx4$^{KD}$ MEF was dramatically reduced when treated with or without TGF-β (FIG. 11(j)). Furthermore, in lung fibroblasts from IPF patients, Tbx4 siRNA transfection inhibited the invasiveness and HA production when treated with or without TGF-β (FIGS. 11 (f) and (g)). TBX4 gene expression also was elevated in invasive human fibroblasts from IPF patients when compared to non-invasive human fibroblasts (FIG. 28). Taken together, these data show that TBX4 mediates fibroblast invasion through HAS2.

Discussion

This study has identified a TBX4-driven fibrogenic cell population as a heterogeneous mesenchymal population, containing interstitial fibroblasts, vascular and airway smooth muscle cells, some pericytes, and a few endothelial cells in the adult mouse lung in normal and disease states. TBX4-labeled cells did not give rise to any lung cells expressing epithelial cell markers. More importantly, Tbx4-lineage cells expanded, proliferated, and formed organized clonal patches during lung fibrosis in mice in vivo. Almost all of the αSMA+ myofibroblasts and COL1a1+ fibroblasts were Tbx4-derived cells, suggesting a role for this population of cells in lung fibrosis. This is further supported by data showing that lung fibrosis is significantly reduced by ablation of Tbx4-lineage cells. When Tbx4 was deleted in SMA- or COL1a2-expressing fibroblasts, lung fibrosis was also significantly reduced. These data support a non-redundant role for TBX4 in regulating the pathobiology of lung fibrosis and show TBX4 mediated fibroblast invasiveness and HA production by transcriptional regulation of HAS2.

These data also show that virtually all αSMA-expressing myofibroblasts as well as COL1a1-expressing fibroblasts were derived from TBX4-expressing cells. Without being bound by theory, these data suggest that within the lung, a local lineage of interstitial resident fibroblasts promotes fibrogenesis, which is consistent with recent studies in skin fibrosis (Dulauroy S, Di Carlo S E, Langa F, Eberl G, Peduto L. Lineage tracing and genetic ablation of ADAM12(+) perivascular cells identify a major source of profibrotic cells during acute tissue injury. Nat Med. 2012; 18(8):1262-1270; 38. Rinkevich Y, et al. Skin fibrosis. Identification and isolation of a dermal lineage with intrinsic fibrogenic potential. Science. 2015; 348(6232):aaa2151), lung fibrosis (Hung C, et al. Role of lung pericytes and resident fibroblasts in the pathogenesis of pulmonary fibrosis. *Am J Respir Crit Care Med.* 2013; 188(7):820-830), and liver fibrosis (Iwaisako K, et al. Origin of myofibroblasts in the fibrotic liver in mice. Proc *Natl Acad Sci USA.* 2014; 111(32):E3297-E3305). The demonstration that Tbx4-lineage cells were devoid of all epithelial cell markers also is in line with previous work (Rock J R, et al. Multiple stromal populations contribute to pulmonary fibrosis without evidence for epithelial to mesenchymal transition. Proc *Natl Acad Sci USA.* 2011; 108 (52):E1475-E1483) suggesting that cell lineage commitment does not cross between epithelial and stromal compartments in lung fibrosis. Epithelial-mesenchymal transition (EMT) has been suggested in the pathogenesis of cardiac fibrosis (Kalluri R, Neilson E G. Epithelial-mesenchymal transition and its implications for fibrosis. *J Clin Invest.* 2003; 112 (12):1776-1784), lung fibrosis (Kim K K, et al. Alveolar epithelial cell mesenchymal transition develops in vivo during pulmonary fibrosis and is regulated by the extracellular matrix. *Proc Natl Acad Sci USA.* 2006; 103(35):13180-13185; Tanjore H, et al. Contribution of epithelial-derived fibroblasts to bleomycin-induced lung fibrosis. Am J Respir Crit *Care Med.* 2009; 180(7):657-665; Chapman H A. Epithelial-mesenchymal interactions in pulmonary fibrosis. *Annu Rev Physiol.* 2011; 73:413-435; Willis B C, et al. Induction of epithelial-mesenchymal transition in alveolar epithelial cells by transforming growth factor-p1: potential role in idiopathic pulmonary fibrosis. *Am J Pathol.* 2005; 166(5):1321-1332), and kidney fibrosis (Zeisberg M, et al. BMP-7 counteracts TGF-beta1-induced epithelial-to-mesenchymal transition and reverses chronic renal injury. *Nat Med.* 2003; 9(7):964-968; Iwano M, Plieth D, Danoff T M, Xue C, Okada H, Neilson E G. Evidence that fibroblasts derive from epithelium during tissue fibrosis. J Clin Invest. 2002; 110(3):341-350.). Conversely, the data did not support a major role for EMT in lung fibrosis. In addition, extrapulmonary contribution of fibroblasts and myofibroblasts is not regulated by Tbx4-derived cells. Bone marrow-derived stromal progenitor cells such as fibrocytes (Bucala R, Spiegel L A, Chesney J, Hogan M, Cerami A. Circulating fibrocytes define a new leukocyte subpopulation that mediates tissue repair. Mol Med. 1994; 1(1):71-81) have been suggested in lung fibrosis (Hashimoto N, Jin H, Liu T, Chensue S W, Phan S H. Bone marrow-derived progenitor cells in pulmonary fibrosis. J Clin Invest. 2004; 113(2):243-252; Moore B B, et al. CCR2-mediated recruitment of fibrocytes to the alveolar space after fibrotic injury. Am J Pathol. 2005; 166(3):675-684). A very small fraction of Tbx4-derived cells were observed in the bone marrow. Collectively, these data indicate that the majority of myofibroblasts and fibroblasts that accumulate during fibrosis are Tbx4 lineage-derived mesenchymal intrapulmonary cells regardless of the particular cell surface expression marker.

Antibody staining data indicated that Tbx4-lineage cells constitutively labeled from the embryonic stage or inducibly labeled post-natally can differentiate into heterogeneous stromal cell types including αSMA+ and COL1a1+ cells. To confirm these antibody staining results, several transgenic reporter lines were used, including αSMA-GFP and COL1a1-GFP mice, to detect the co-localization of αSMA- and Col1a1-expressing cells within the Tbx4-lineage cells by means of confocal microscopy and FACS analysis. The data showed that αSMA-expressing cells are significantly increased in the fibrotic lung. Almost all of the αSMA-expressing cells (over 90%) were Tbx4-lineage cells. A large portion of Tbx4-lineage-only (TBX4+αSMA−) cells also were detected, indicating that not only αSMA+ cells but other non-αSMA mesenchymal cells accumulate during fibrosis. These data are in line with a previous study showing that multiple stromal populations contribute to pulmonary fibrosis, including αSMA, vimentin, desmin, PDGFRp, and NG2, by using antibody staining (Rock J R, et al. Multiple stromal populations contribute to pulmonary fibrosis without evidence for epithelial to mesenchymal transition. *Proc Natl Acad Sci USA.* 2011; 108(52):E1475-E1483.). In addition, the data showed that the vast majority of COL1a1+ cells are Tbx4-lineage cells. COL1a1+ cells are considered resident fibroblasts (Hung C, et al. Role of lung pericytes and resident fibroblasts in the pathogenesis of pulmonary fibrosis. *Am J Respir Crit Care Med.* 2013; 188(7):820-830; Kramann R, et al. Perivascular Gli1+ progenitors are key contributors to injury-induced organ fibrosis. Cell Stem Cell. 2015; 16(1):51-66; Iwaisako K, et al. Origin of myofibroblasts in the fibrotic liver in mice. Proc *Natl Acad Sci USA.* 2014; 111(32):E3297-E3305), while some data suggest that circulating fibrocytes can express COL1a1 (Bucala R, Spiegel L A, Chesney J, Hogan M, Cerami A. Circulating fibrocytes define a new leukocyte subpopulation that mediates tissue repair. Mol Med. 1994; 1(1):71-81; van Deventer H W, Palmieri D A, Wu Q P, McCook E C, Serody J S. Circulating fibrocytes prepare the lung for cancer metastasis by recruiting Ly-6C+ monocytes via CCL2. J Immunol. 2013; 190(9):4861-4867.). Without being bound by theory, the data presented in this study suggest that the majority of COL1a1+ cells are resident fibroblasts, although a small proportion of COL1a1 single-positive cells, the circulating fibrocytes, were observed.

Pericytes are defined as mesenchymal cells that share a common basement membrane with endothelial cells (Bergers G, Song S. The role of pericytes in blood-vessel formation and maintenance. *Neurooncology.* 2005; 7(4):452-464). They have been suggested as a source of fibroblasts during tissue fibrosis (Kramann R, et al. Perivascular Gli1+ progenitors are key contributors to injury-induced organ fibrosis. Cell Stem Cell. 2015; 16(1):51-66; Humphreys B D, et al. Fate tracing reveals the pericyte and not epithelial origin of myofibroblasts in kidney fibrosis. Am J *Pathol.* 2010; 176(1):85-97). The lineage labeling data demonstrated that a maximum of 20% of NG2+ cells are Tbx4-lineage cells. Considering that the majority of αSMA+ cells are Tbx4-lineage cells, our results indicate that NG2+ cells represent a minor population of αSMA+ cells. These data are consistent with a previous study using Ng2-CreER mice, which demonstrated that NG2+ pericytes do not express high levels of αSMA in fibrotic lungs (Rock J R, et al. Multiple stromal populations contribute to pulmonary fibrosis without evidence for epithelial to mesenchymal transition. *Proc Natl Acad Sci USA.* 2011; 108(52):E1475-E1483). These data also support recent reports that NG2 may not be a reliable marker for all pericytes (Hung C, et al. Role of lung pericytes and resident fibroblasts in the pathogenesis of pulmonary fibrosis. *Am J Respir Crit Care Med.* 2013; 188(7):820-830; LeBleu V S, et al. Origin and function of myofibroblasts in kidney fibrosis. Nat Med. 2013; 19(8): 1047-1053; Duffield J S. Cellular and molecular mechanisms in kidney fibrosis. J Clin Invest. 2014; 124(6):2299-2306). Antibody staining with another pericyte marker, PDGFRβ, showed much more co-localization with Tbx4-lineage cells than NG2 staining, which suggests that PDGFRβ may be a better marker for pericytes than NG2. Collectively, these data show that NG2+ pericytes are not the major contributor to myofibroblasts in lung fibrosis.

The antibody staining data also showed that Tbx4-lineage progenitor cells not only contain αSMA+, COL1a1+, and NG2+ cells, but also include endothelial cells. The data indicated that this population does not increase during fibrosis, consistent with a report that PECAM-1 co-stained with Tbx4-lineage cells in embryonic mouse lung (Zhang W, et al. Spatial-temporal targeting of lung-specific mesenchyme by a Tbx4 enhancer. *BMC Biol.* 2013; 11:111).

Mesenchyme-specific clonal analysis was used to examine expansion of TBX4-expressing cells during fibrosis. The data showed that TBX4-expressing cells expanded clonally. Within 3 weeks after bleomycin injury, clone size was at least 6 cells. These patches seemed to be monoclonal, indicating that regeneration foci are derived from a single Tbx4 progenitor. These data showed that the mesenchymal progenitors during fibrogenesis are similar to the embryonic-stage mesenchymal cells, which are highly proliferative and progressively expand (Kumar M E, Bogard P E, Espinoza F H, Menke D B, Kingsley D M, Krasnow M A. Mesenchymal cells. Defining a mesenchymal progenitor niche at single-cell resolution. *Science*. 2014; 346(6211):1258810). These findings indicate that mesenchymal progenitors proliferate and self-renew during lung fibrogenesis, which supports the previously suggested concept that during lung fibrosis, embryonic gene programs are reactivated (Selman M, Pardo A, Kaminski N. Idiopathic pulmonary fibrosis: aberrant recapitulation of developmental programs?. PLoS Med. 2008; 5(3):e62).

Without being bound by theory, TBX4, acting as a mesenchymal transcription factor, may control downstream gene expression and impact key fibroblast effector functions. In order to gain insights into possible target genes, Tbx4-lineage and non-Tbx4-lineage cell gene expression was analyzed and identified mesenchymal genes that could be regulated by TBX4. Among them, Has2 was upregulated in TBX4-expressing cells. Has2 is 1 of the 3 HA synthase genes that have been identified. αSMA-Has2 mice showed increased fibrosis after bleomycin injury, and mice with conditional deletion of Has2 in mesenchymal cells exhibited less fibrosis (Li Y, et al. Severe lung fibrosis requires an invasive fibroblast phenotype regulated by hyaluronan and CD44. *J Exp Med*. 2011; 208(7):1459-1471). TBX4 regulation of Has2 and its impact on the fibroblast invasive phenotype was analyzed. These data showed that TBX4 regulated both fibroblast invasiveness and HA production by binding to the Has2 promoter and triggering Has2 gene expression. These data establish TBX4 as a proximal regulator of Has2 expression, HA production, and fibroblast invasiveness.

Without being bound by theory, the array data suggested that TBX4 may regulate additional fibroblast and ECM remodeling genes, including Fgf Pdgfr, Mmp, and Adam family genes. It has been shown that TBX4 and TBX5 are linked to the activity of FGF, BMP, and WNT signaling pathways that are required for limb outgrowth and patterning (Rodriguez-Esteban C, Tsukui T, Yonei S, Magallon J, Tamura K, Izpisua Belmonte J C. The T-box genes Tbx4 and Tbx5 regulate limb outgrowth and identity. *Nature*. 1999; 398(6730):814-818). TBX4 and TBX5 are considered critical for expression of mesenchymal FGF10 in embryonic mouse lung (Cebra-Thomas J A, Bromer J, Gardner R, Lam G K, Sheipe H, Gilbert S F. T-box gene products are required for mesenchymal induction of epithelial branching in the embryonic mouse lung. Dev Dyn. 2003; 226(1):82-90). It has been reported that TBX4 and TBX5 trigger limb formation by the induction of both Wnt and Fgf (55. Takeuchi J K, Koshiba-Takeuchi K, Suzuki T, Kamimura M, Ogura K, Ogura T. Tbx5 and Tbx4 trigger limb initiation through activation of the Wnt/Fgf signaling cascade. *Development*. 2003; 130(12):2729-2739). There are no reports to date directly linking Tbx4 and Mmp gene expression, although inhibition of the T-box transcription factor Brachyury showed downregulation of Mmp2 and Mmp24 in the context of EMT in cancer (Fernando R I, Litzinger M, Trono P, Hamilton D H, Schlom J, Palena C. The T-box transcription factor Brachyury promotes epithelial-mesenchymal transition in human tumor cells. J Clin Invest. 2010; 120(2):533-544.). Moreover, T-BET, another T-box transcription factor, was found increased together with MMP3 when TGF-p was blocked in human gut (Di Sabatino A, et al. Blockade of transforming growth factor beta upregulates T-box transcription factor T-bet, and increases T helper cell type 1 cytokine and matrix metalloproteinase-3 production in the human gut mucosa. *Gut*. 2008; 57(5):605-612).

Without being bound by theory, the data suggest a hierarchical relationship of TBX4-lineage fibroblasts with other mesenchymal populations, such as FGF10+, GLI1+, ADAM12+, PDGFRa+, and FOXD1+ cells. TBX4 is a potential upstream regulator of these genes and is detected as early as E9.25 exclusively in lung mesenchyme without epithelial expression (Takeuchi J K, et al. Tbx5 and Tbx4 genes determine the wing/leg identity of limb buds. *Nature*. 1999; 398(6730):810-814; Arora R, Metzger R J, Papaioannou V E. Multiple roles and interactions of Tbx4 and Tbx5 in development of the respiratory system. PLoS *Genet*. 2012; 8(8):e1002866; Kumar M E, Bogard P E, Espinoza F H, Menke D B, Kingsley D M, Krasnow M A. Mesenchymal cells. Defining a mesenchymal progenitor niche at single-cell resolution. *Science*. 2014; 346(6211):1258810; Naiche L A, Arora R, Kania A, Lewandoski M, Papaioannou V E. Identity and fate of Tbx4-expressing cells reveal developmental cell fate decisions in the allantois, limb, and external genitalia. *DevDyn*. 2011; 240(10):2290-2300; Naiche L A, Papaioannou V E. Loss of Tbx4 blocks hindlimb development and affects vascularization and fusion of the allantois. Development. 2003; 130(12):2681-2693; Sakiyama J, Yamagishi A, Kuroiwa A. Tbx4-Fgf10 system controls lung bud formation during chicken embryonic development. *Development*. 2003; 130(7):1225-1234). TBX4 induces mesenchymal genes and the pluripotent stem cell-related transcription factors (Gata2 and Gata3; Smad1, Smad2, Smad3, and Smad5; and Snail) in adult mice, suggesting that TBX4 can be a critical driver of fibroblast differentiation.

Collectively, this study has demonstrated that Tbx4-lineage cells (i) represent most of the resident mesenchymal progenitors; (ii) expand during fibrosis; and (iii) form clonal patches. These data also demonstrate that TBX4 drives fibroblast matrix production and invasiveness through the regulation of Has2.

While the present invention has been described with reference to the specific embodiments thereof it should be understood by those skilled in the art that various changes may be made and equivalents may be substituted without departing from the true spirit and scope of the invention. In addition, many modifications may be made to adopt a particular situation, material, composition of matter, process, process step or steps, to the objective spirit and scope of the present invention. All such modifications are intended to be within the scope of the claims appended hereto.

What is claimed is:

1. A method for reducing progression of lung fibrosis after a lung injury in a subject, comprising administering locally to a lung of the subject a therapeutic amount of a therapeutic agent, wherein the therapeutic agent is a small interfering RNA (siRNA), wherein the therapeutic amount is effective: (a) to inhibit expression of a T-box transcription factor protein T-box protein 4 (Tbx4) in a population of cells in lung expressing Tbx4 and (b) to reduce proliferation of the population of cells in lung expressing Tbx4.

2. The method according to claim 1, wherein the nucleic acid inhibitor is a small interfering RNA (siRNA) of nucleic acid sequence 5'-rGrCrArCrUrGrCrCrArArGrArArAr-CrArUrGrGrArArGGT-3' (SEQ ID NO: 1).

3. The method according to claim 1, wherein the nucleic acid inhibitor is a small interfering RNA (siRNA) of nucleic acid sequence 5'-rUrGrCrArArUrUrArUrCrUrArArGrArA-rGrUrGrArCrUrUTG-3' (SEQ ID NO: 2).

4. The method according to claim 1, wherein the population of cells in lung in which Tbx4 is expressed is heterogeneous.

5. The method according to claim 4, wherein the population of cells in lung in which Tbx4 is expressed comprises one or more of a population of pericytes, a population of lipofibroblasts, a population of endothelial cells, or a population of myofibroblasts.

6. The method according to claim 5, wherein the population of cells in lung in which Tbx4 is expressed is further characterized by expression of one or more markers selected from α-smooth muscle actin (αSMA), Col1a1, desmin, vimentin, NG2, and PDGFRβ.

7. The method according to claim 5, wherein the population of myofibroblasts in lung is characterized by expression of Tbx4 and αSMA.

8. The method according to claim 5, wherein the population of cells in lung in which Tbx4 is expressed comprises a population of fibroblasts resident in the lung of the subject.

9. The method according to any one of claims 2 and 3, wherein knockdown of Tbx4 with the siRNA is effective to reduce invasiveness of myofibroblasts.

10. The method according to claim 1, wherein inhibition of expression of Tbx4 is effective to modulate expression of Has-2.

11. The method according to claim any one of claims 2 and 3, wherein the therapeutic amount of the Tbx4 siRNA is effective to decrease TGFβ-induced release of hyaluronic acid (HA).

12. The method according to claim 1, wherein the therapeutic amount of the therapeutic agent is effective to reduce symptoms of pulmonary fibrosis.

* * * * *

SEQUENCE LISTING

<160> NUMBER OF SEQ ID NOS: 11

<210> SEQ ID NO 1
<211> LENGTH: 25
<212> TYPE: DNA
<213> ORGANISM: Artificial Sequence

```
<220> FEATURE:
<223> OTHER INFORMATION: siRNA

<400> SEQUENCE: 1
gcacugccaa gaaacaugga aaggt                                              25

<210> SEQ ID NO 2
<211> LENGTH: 25
<212> TYPE: DNA
<213> ORGANISM: Artificial Sequence
<220> FEATURE:
<223> OTHER INFORMATION: siRNA

<400> SEQUENCE: 2
ugcaauuauc uaagaaguga cuutg                                              25

<210> SEQ ID NO 3
<211> LENGTH: 22
<212> TYPE: DNA
<213> ORGANISM: Artificial Sequence
<220> FEATURE:
<223> OTHER INFORMATION: Primer

<400> SEQUENCE: 3
acgacgacct ttacatgatg ga                                                 22

<210> SEQ ID NO 4
<211> LENGTH: 21
<212> TYPE: DNA
<213> ORGANISM: Artificial Sequence
<220> FEATURE:
<223> OTHER INFORMATION: Primer

<400> SEQUENCE: 4
gatgtacgtg gccgatttgc t                                                  21

<210> SEQ ID NO 5
<211> LENGTH: 25
<212> TYPE: DNA
<213> ORGANISM: Artificial Sequence
<220> FEATURE:
<223> OTHER INFORMATION: Primer

<400> SEQUENCE: 5
tcactggatg cggcagttgg tctct                                              25

<210> SEQ ID NO 6
<211> LENGTH: 25
<212> TYPE: DNA
<213> ORGANISM: Artificial Sequence
<220> FEATURE:
<223> OTHER INFORMATION: Primer

<400> SEQUENCE: 6
cacgtgggtg caaaaggctg tgttt                                              25

<210> SEQ ID NO 7
<211> LENGTH: 19
<212> TYPE: DNA
<213> ORGANISM: Artificial Sequence
<220> FEATURE:
<223> OTHER INFORMATION: Primer

<400> SEQUENCE: 7
atcatctccg cccccttctg                                                    19
```

```
<210> SEQ ID NO 8
<211> LENGTH: 21
<212> TYPE: DNA
<213> ORGANISM: Artificial Sequence
<220> FEATURE:
<223> OTHER INFORMATION: Primer

<400> SEQUENCE: 8
ggtcatgagc ccttccacaa c                                               21

<210> SEQ ID NO 9
<211> LENGTH: 25
<212> TYPE: DNA
<213> ORGANISM: Artificial Sequence
<220> FEATURE:
<223> OTHER INFORMATION: Primer

<400> SEQUENCE: 9
caagctcgag ggaatccttg taacg                                           25

<210> SEQ ID NO 10
<211> LENGTH: 25
<212> TYPE: DNA
<213> ORGANISM: Artificial Sequence
<220> FEATURE:
<223> OTHER INFORMATION: Primer

<400> SEQUENCE: 10
ccgcctcgag tcccgcccag tccct                                           25

<210> SEQ ID NO 11
<211> LENGTH: 33
<212> TYPE: DNA
<213> ORGANISM: Artificial Sequence
<220> FEATURE:
<223> OTHER INFORMATION: Primer

<400> SEQUENCE: 11
tgccaagctt cttgttcagc tcctgctcat aga                                  33
```